United States Patent

Tarasova et al.

(10) Patent No.: US 7,105,488 B1
(45) Date of Patent: Sep. 12, 2006

(54) G PROTEIN-COUPLED RECEPTOR ANTAGONISTS

(75) Inventors: Nadya I. Tarasova, Frederick, MD (US); Christopher J. Michejda, North Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/601,600

(22) PCT Filed: Feb. 26, 1999

(86) PCT No.: PCT/US99/04438

§ 371 (c)(1),
(2), (4) Date: Oct. 2, 2000

(87) PCT Pub. No.: WO99/43711

PCT Pub. Date: Sep. 2, 1999

Related U.S. Application Data

(60) Provisional application No. 60/076,105, filed on Feb. 27, 1998.

(51) Int. Cl.
*A61K 38/04* (2006.01)
*C07K 5/00* (2006.01)
*C07K 16/00* (2006.01)
*C07K 17/00* (2006.01)
*G01N 33/567* (2006.01)

(52) U.S. Cl. .............................. 514/16; 514/2; 514/17; 514/18; 514/19; 530/328; 530/29; 530/30; 536/23.5; 435/7.21; 436/501

(58) Field of Classification Search .................. 514/2, 514/12, 13, 14; 530/300, 324, 326, 327, 530/332, 345, 350; 435/7.21, 69.1, 69.2, 435/69.4; 436/501; 536/23.5
See application file for complete search history.

(56) References Cited

U.S. PATENT DOCUMENTS 5,508,384 A    4/1996 Murphy et al.

FOREIGN PATENT DOCUMENTS

| WO | WO 94/05695 | * 3/1994 |
| WO | WO 97/28258 | 8/1997 |
| WO | WO 97/35881 | 10/1997 |
| WO | WO 98/00538 | 1/1998 |

OTHER PUBLICATIONS

Ulrich et al., Biochem. Biophys. Res. Comm. 193(1)204-211, 1993.*
Bowie et al., 1990, Science 247:1306-1310.*
Guo-HH et al. PNAS 101(25)9205-9210, 2004.*
Anand-Srivastava et al. (1996) "Cytoplasmic Domain of Natiuretic Peptide Receptor-C Inhibits Adenylyl Cyclase", J. Biol.Chem. 271:19324-19329.
Gudermann et al. (1997) "Functional and structural complexity of signal transduction via G-protein-coupled receptors", Annu. Rev. Neurosci. 20:399-427.
Hebert et al. (1996) "A peptide derived from a beta2-adrenergic receptor transmembrane domain inhibits both receptor dimerization and activation", J. Biol. Chem. 71(27):16384-92.
Merkouris et al. (1996) "Identification of the critical domains of the delta-opioid receptor involved in G protein coupling using site-specific synthetic peptides", Mol. Pharmacol. 50(4):985-93.
Monnot et al. (1996) "Polar residues in the transmembrane domains of the type 1 angiotensin II receptor are required for binding and coupling. Reconstitution of the binding site by co-expression of two deficient mutants", J. Biol. Chem. 271(3):1507-13.
Moro et al. (1993) "Hydrophobic amino acid in the i2 loop plays a key role in receptor -G protein coupling", J. Biol. Chem. 268:22273-6.
Osuga et al. (1997) "Co-expression of defective luteinizing hormone receptor fragments partially reconstitutes ligand-induced signal generation", J. Biol. Chem. 272:25006-12.
Raport et al. (1996) "Molecular cloning and functional characterization of a novel human CC chemokine receptor (CCR5) for RANTES, MIP-1beta, and MIP-1alpha", J. Biol. Chem. 271:17171-17166.
Schoneberg et al. (1996) "Functional rescue of mutant V2 vasopressin receptors causing nephrogenic diabetes insipidus by a co-expressed receptor polypeptide", EMBO J. 15:1283-91.
Wong et al. (1990) "Chimeric muscarinic cholinergic: beta-adrenergic receptors that activate Gs in response to muscarinic agonists", J. Biol. Chem. 265:6219-6324.

* cited by examiner

*Primary Examiner*—Janet L. Andres
*Assistant Examiner*—Michael Brannock
(74) *Attorney, Agent, or Firm*—Townsend and Townsend and Crew LLP

(57) ABSTRACT

G-protein coupled receptors (GPCR) generally contain seven transmembrane helices. The present invention provides synthetic peptides derived from these transmembrane helices. The peptides inhibit GPCR function by disrupting GPCR structure. In certain embodiments, charged residues are added at one terminus to promote correct orientation of the peptide in the membrane.

7 Claims, 3 Drawing Sheets

SEQUENCE LISTING

```
<160> NUMBER OF SEQ ID NOS: 363

<210> SEQ ID NO 1
<211> LENGTH: 24
<212> TYPE: PRT
<213> ORGANISM: Artificial Sequence
<220> FEATURE:
<223> OTHER INFORMATION: F-2-2 GPCR CXCR4

<400> SEQUENCE: 1

Leu Leu Phe Val Ile Thr Leu Pro Phe Trp Ala Val Asp Ala Val Ala
1               5                   10                  15

Asn Trp Tyr Phe Gly Asn Asp Asp
            20

<210> SEQ ID NO 2
<211> LENGTH: 19
<212> TYPE: PRT
<213> ORGANISM: Artificial Sequence
<220> FEATURE:
<223> OTHER INFORMATION: F-2-5 GPCR CXCR4

<400> SEQUENCE: 2

Leu Leu Phe Val Ile Thr Leu Pro Phe Trp Ala Val Asp Ala Val Ala
1               5                   10                  15

Asn Asp Asp
```

<210> SEQ ID NO 3
<211> LENGTH: 23
<212> TYPE: PRT
<213> ORGANISM: Artificial Sequence
<220> FEATURE:
<223> OTHER INFORMATION: F-4-2 GPCR CXCR4

<400> SEQUENCE: 3

Val Tyr Val Gly Val Trp Ile Pro Ala Leu Leu Leu Thr Ile Pro Asp
 1               5                  10                  15

Phe Ile Phe Ala Asn Asp Asp
            20

<210> SEQ ID NO 4
<211> LENGTH: 21
<212> TYPE: PRT
<213> ORGANISM: Artificial Sequence
<220> FEATURE:
<223> OTHER INFORMATION: F-6-1 GPCR CXCR4

<400> SEQUENCE: 4

Val Ile Leu Ile Leu Ala Phe Phe Ala Cys Trp Leu Pro Tyr Tyr Ile
 1               5                  10                  15

Gly Ile Ser Ile Asp
            20

<210> SEQ ID NO 5
<211> LENGTH: 20
<212> TYPE: PRT
<213> ORGANISM: Artificial Sequence
<220> FEATURE:
<223> OTHER INFORMATION: F-7-3 GPCR CXCR4
<221> NAME/KEY: MOD_RES
<222> LOCATION: (20)...(20)
<223> OTHER INFORMATION: Xaa = leucinamide

<400> SEQUENCE: 5

Asp Asp Glu Ala Leu Ala Phe Phe His Cys Cys Leu Asn Pro Ile Leu
 1               5                  10                  15

Tyr Ala Phe Xaa
            20

<210> SEQ ID NO 6
<211> LENGTH: 23
<212> TYPE: PRT
<213> ORGANISM: Artificial Sequence
<220> FEATURE:
<223> OTHER INFORMATION: F-7-4 GPCR CXCR4
<221> NAME/KEY: MOD_RES
<222> LOCATION: (23)...(23)
<223> OTHER INFORMATION: Xaa = leucinamide

<400> SEQUENCE: 6

Asp Asp Ser Ile Thr Glu Ala Leu Ala Phe Phe His Cys Cys Leu Asn
 1               5                  10                  15

Pro Ile Leu Tyr Ala Phe Xaa
            20

<210> SEQ ID NO 7
<211> LENGTH: 23
<212> TYPE: PRT
<213> ORGANISM: Artificial Sequence
<220> FEATURE:
<223> OTHER INFORMATION: CCR5-TM-2-2 GPCR CCR5

-continued

```
<400> SEQUENCE: 7

Leu Phe Phe Leu Leu Thr Val Pro Phe Trp Ala His Tyr Ala Ala Ala
 1               5                  10                  15

Gln Trp Asp Phe Gly Asp Asp
             20

<210> SEQ ID NO 8
<211> LENGTH: 28
<212> TYPE: PRT
<213> ORGANISM: Artificial Sequence
<220> FEATURE:
<223> OTHER INFORMATION: CCR5-TM-4-1 GPCR CCR5

<400> SEQUENCE: 8

Phe Gly Val Val Thr Ser Val Ile Thr Trp Val Val Ala Val Phe Ala
 1               5                  10                  15

Ser Leu Pro Gly Ile Ile Phe Thr Ser Ser Asp Asp
             20                  25

<210> SEQ ID NO 9
<211> LENGTH: 28
<212> TYPE: PRT
<213> ORGANISM: Artificial Sequence
<220> FEATURE:
<223> OTHER INFORMATION: CCR5-TM-6-1 GPCR CCR5

<400> SEQUENCE: 9

Leu Ile Phe Thr Ile Met Ile Val Tyr Phe Leu Phe Trp Ala Pro Tyr
 1               5                  10                  15

Asn Ile Val Leu Leu Leu Asn Thr Phe Gln Glu Asp
             20                  25

<210> SEQ ID NO 10
<211> LENGTH: 26
<212> TYPE: PRT
<213> ORGANISM: Artificial Sequence
<220> FEATURE:
<223> OTHER INFORMATION: CCR5-TM-7-1 GPCR CCR5

<400> SEQUENCE: 10

Asp Asp Gln Ala Met Gln Val Thr Glu Thr Leu Gly Met Thr His Cys
 1               5                  10                  15

Cys Ile Asn Pro Ile Ile Tyr Ala Phe Val
             20                  25

<210> SEQ ID NO 11
<211> LENGTH: 23
<212> TYPE: PRT
<213> ORGANISM: Artificial Sequence
<220> FEATURE:
<223> OTHER INFORMATION: CCR2-TM-2-1 GPCR CCR2

<400> SEQUENCE: 11

Ile Tyr Leu Leu Asn Leu Ala Ile Ser Asp Leu Leu Phe Leu Ile Thr
 1               5                  10                  15

Leu Pro Leu Trp Ala Asp Asp
             20

<210> SEQ ID NO 12
<211> LENGTH: 24
<212> TYPE: PRT
<213> ORGANISM: Artificial Sequence
<220> FEATURE:
<223> OTHER INFORMATION: CCR2-TM-2-2 GPCR CCR2
```

```
<400> SEQUENCE: 12

Leu Leu Phe Leu Ile Thr Leu Pro Leu Trp Ala His Ser Ala Ala Asn
1               5                   10                  15

Glu Trp Val Phe Gly Asn Asp Asp
            20

<210> SEQ ID NO 13
<211> LENGTH: 26
<212> TYPE: PRT
<213> ORGANISM: Artificial Sequence
<220> FEATURE:
<223> OTHER INFORMATION: CCR2-TM-4-1 GPCR CCR2

<400> SEQUENCE: 13

Phe Gly Val Val Thr Ser Val Ile Thr Trp Leu Val Ala Val Phe Ala
1               5                   10                  15

Ser Val Pro Gly Ile Ile Phe Thr Asp Asp
            20                  25

<210> SEQ ID NO 14
<211> LENGTH: 28
<212> TYPE: PRT
<213> ORGANISM: Artificial Sequence
<220> FEATURE:
<223> OTHER INFORMATION: CCR2-TM-6-1 GPCR CCR2

<400> SEQUENCE: 14

Val Ile Phe Thr Ile Met Ile Val Tyr Phe Leu Phe Trp Thr Pro Tyr
1               5                   10                  15

Asn Ile Val Ile Leu Leu Asn Thr Phe Gln Glu Asp
            20                  25

<210> SEQ ID NO 15
<211> LENGTH: 25
<212> TYPE: PRT
<213> ORGANISM: Artificial Sequence
<220> FEATURE:
<223> OTHER INFORMATION: CCR2-TM-7-1 GPCR CCR2

<400> SEQUENCE: 15

Asp Asp Ala Thr Gln Val Thr Glu Thr Leu Gly Met Thr His Cys Cys
1               5                   10                  15

Ile Asn Pro Ile Ile Tyr Ala Phe Val
            20                  25

<210> SEQ ID NO 16
<211> LENGTH: 25
<212> TYPE: PRT
<213> ORGANISM: Artificial Sequence
<220> FEATURE:
<223> OTHER INFORMATION: CCR3-TM-2-1 GPCR CCR3

<400> SEQUENCE: 16

Leu Leu Phe Leu Val Thr Leu Pro Phe Trp Ile His Tyr Val Arg Gly
1               5                   10                  15

His Asn Trp Val Phe Gly Asp Asp Asp
            20                  25

<210> SEQ ID NO 17
<211> LENGTH: 28
<212> TYPE: PRT
<213> ORGANISM: Artificial Sequence
<220> FEATURE:
<223> OTHER INFORMATION: CCR3-TM-4-1 GPCR CCR3
```

-continued

```
<400> SEQUENCE: 17

Phe Gly Val Ile Thr Ser Ile Val Thr Trp Gly Leu Ala Val Leu Ala
1               5                   10                  15

Ala Leu Pro Glu Phe Ile Phe Tyr Glu Thr Glu Asp
            20                  25

<210> SEQ ID NO 18
<211> LENGTH: 28
<212> TYPE: PRT
<213> ORGANISM: Artificial Sequence
<220> FEATURE:
<223> OTHER INFORMATION: CCR3-TM-6-1 GPCR CCR3

<400> SEQUENCE: 18

Ile Phe Val Ile Met Ala Val Phe Phe Ile Phe Trp Thr Pro Tyr Asn
1               5                   10                  15

Val Ala Ile Leu Leu Ser Ser Tyr Gln Ser Asp Asp
            20                  25

<210> SEQ ID NO 19
<211> LENGTH: 26
<212> TYPE: PRT
<213> ORGANISM: Artificial Sequence
<220> FEATURE:
<223> OTHER INFORMATION: CCR3-TM-7-1 GPCR CCR3

<400> SEQUENCE: 19

Asp Asp Leu Val Met Leu Val Thr Glu Val Ile Ala Tyr Ser His Cys
1               5                   10                  15

Cys Met Asn Pro Val Ile Tyr Ala Phe Val
            20                  25

<210> SEQ ID NO 20
<211> LENGTH: 30
<212> TYPE: PRT
<213> ORGANISM: Artificial Sequence
<220> FEATURE:
<223> OTHER INFORMATION: CCKAR-TM-1-6 GPCR CCKAR

<400> SEQUENCE: 20

Asp Asp Glu Trp Gln Ser Ala Leu Gln Ile Leu Leu Tyr Ser Ile Ile
1               5                   10                  15

Phe Leu Leu Ser Val Leu Gly Asn Thr Leu Val Ile Thr Val
            20                  25                  30

<210> SEQ ID NO 21
<211> LENGTH: 22
<212> TYPE: PRT
<213> ORGANISM: Artificial Sequence
<220> FEATURE:
<223> OTHER INFORMATION: CCKAR-TM-2-1 GPCR CCKAR

<400> SEQUENCE: 21

Phe Leu Leu Ser Leu Ala Val Ser Asp Leu Met Leu Cys Leu Phe Cys
1               5                   10                  15

Met Pro Phe Asn Leu Pro
            20

<210> SEQ ID NO 22
<211> LENGTH: 24
<212> TYPE: PRT
<213> ORGANISM: Artificial Sequence
<220> FEATURE:
<223> OTHER INFORMATION: CCKAR-TM-2-2 GPCR CCKAR
```

```
<400> SEQUENCE: 22

Phe Leu Leu Ser Leu Ala Val Ser Asp Leu Met Leu Cys Leu Phe Cys
 1               5                  10                  15

Met Pro Phe Asn Leu Ile Asp Asp
            20

<210> SEQ ID NO 23
<211> LENGTH: 26
<212> TYPE: PRT
<213> ORGANISM: Artificial Sequence
<220> FEATURE:
<223> OTHER INFORMATION: CCKAR-TM-6-4 GPCR CCKAR

<400> SEQUENCE: 23

Ile Val Val Leu Phe Phe Leu Cys Trp Met Pro Ile Phe Ser Ala Asn
 1               5                  10                  15

Ala Trp Arg Ala Tyr Asp Thr Val Asp Asp
            20                  25

<210> SEQ ID NO 24
<211> LENGTH: 43
<212> TYPE: PRT
<213> ORGANISM: Artificial Sequence
<220> FEATURE:
<223> OTHER INFORMATION: GPCRAelegans GPCR TM1

<400> SEQUENCE: 24

His Pro Cys Glu Asp Ile Met Gly Tyr Val Trp Leu Thr Val Val Ser
 1               5                  10                  15

Phe Met Val Gly Ala Val Ala Leu Val Ala Asn Leu Val Val Ala Leu
            20                  25                  30

Val Leu Leu Thr Ser Gln Arg Arg Leu Asn Val
        35                  40

<210> SEQ ID NO 25
<211> LENGTH: 50
<212> TYPE: PRT
<213> ORGANISM: Artificial Sequence
<220> FEATURE:
<223> OTHER INFORMATION: GRH GPCR TM1

<400> SEQUENCE: 25

Asn Leu Pro Thr Leu Thr Leu Ser Gly Lys Ile Arg Val Thr Val Thr
 1               5                  10                  15

Phe Phe Leu Phe Leu Leu Ser Ala Thr Phe Asn Ala Ser Phe Leu Leu
            20                  25                  30

Lys Leu Gln Lys Trp Thr Gln Lys Lys Glu Lys Gly Lys Lys Leu Ser
        35                  40                  45

Arg Met
    50

<210> SEQ ID NO 26
<211> LENGTH: 43
<212> TYPE: PRT
<213> ORGANISM: Artificial Sequence
<220> FEATURE:
<223> OTHER INFORMATION: TRH GPCR TM1
```

-continued

```
<400> SEQUENCE: 26

Arg Ala Val Val Ala Leu Glu Tyr Gln Val Val Thr Ile Leu Leu Val
 1               5                  10                  15

Leu Ile Ile Cys Gly Leu Gly Ile Val Gly Asn Ile Met Val Val Leu
             20                  25                  30

Val Val Met Arg Thr Lys His Met Arg Thr Pro
         35                  40

<210> SEQ ID NO 27
<211> LENGTH: 43
<212> TYPE: PRT
<213> ORGANISM: Artificial Sequence
<220> FEATURE:
<223> OTHER INFORMATION: FSHprec GPCR TM1

<400> SEQUENCE: 27

Asn Pro Cys Glu Asp Ile Met Gly Tyr Asn Ile Leu Arg Val Leu Ile
 1               5                  10                  15

Trp Phe Ile Ser Ile Leu Ala Ile Thr Gly Asn Ile Ile Val Leu Val
             20                  25                  30

Ile Leu Thr Thr Ser Gln Tyr Lys Leu Thr Val
         35                  40

<210> SEQ ID NO 28
<211> LENGTH: 43
<212> TYPE: PRT
<213> ORGANISM: Artificial Sequence
<220> FEATURE:
<223> OTHER INFORMATION: TSHprec GPCR TM1

<400> SEQUENCE: 28

Asn Pro Cys Glu Asp Ile Met Gly Tyr Lys Phe Leu Arg Ile Val Val
 1               5                  10                  15

Trp Phe Val Ser Leu Leu Ala Leu Leu Gly Asn Val Phe Val Leu Leu
             20                  25                  30

Ile Leu Leu Thr Ser His Tyr Lys Leu Asn Val
         35                  40

<210> SEQ ID NO 29
<211> LENGTH: 43
<212> TYPE: PRT
<213> ORGANISM: Artificial Sequence
<220> FEATURE:
<223> OTHER INFORMATION: LH_CGprec GPCR TM1

<400> SEQUENCE: 29

Asn Pro Cys Glu Asp Ile Met Gly Tyr Asp Phe Leu Arg Val Leu Ile
 1               5                  10                  15

Trp Leu Ile Asn Ile Leu Ala Ile Met Gly Asn Met Thr Val Leu Phe
             20                  25                  30

Val Leu Leu Thr Ser Arg Tyr Lys Leu Thr Val
         35                  40

<210> SEQ ID NO 30
<211> LENGTH: 49
<212> TYPE: PRT
<213> ORGANISM: Artificial Sequence
<220> FEATURE:
<223> OTHER INFORMATION: PGE_EP1 GPCR TM1
```

-continued

```
<400> SEQUENCE: 30

Pro Asn Thr Ser Ala Val Pro Pro Ser Gly Ala Ser Pro Ala Leu Pro
1               5                   10                  15

Ile Phe Ser Met Thr Leu Gly Ala Val Ser Asn Leu Leu Ala Leu Ala
            20                  25                  30

Leu Leu Ala Gln Ala Ala Gly Arg Leu Arg Arg Arg Ser Ala Thr
        35                  40                  45

Thr

<210> SEQ ID NO 31
<211> LENGTH: 45
<212> TYPE: PRT
<213> ORGANISM: Artificial Sequence
<220> FEATURE:
<223> OTHER INFORMATION: PGE_EP2 GPCR TM1

<400> SEQUENCE: 31

Ser Ala Ser Leu Ser Pro Asp Arg Leu Asn Ser Pro Val Thr Ile Pro
1               5                   10                  15

Ala Val Met Phe Ile Phe Gly Val Val Gly Asn Leu Val Ala Ile Val
            20                  25                  30

Val Leu Cys Lys Ser Arg Lys Glu Gln Lys Glu Thr Thr
        35                  40                  45

<210> SEQ ID NO 32
<211> LENGTH: 45
<212> TYPE: PRT
<213> ORGANISM: Artificial Sequence
<220> FEATURE:
<223> OTHER INFORMATION: PGE_EP3 GPCR TM1

<400> SEQUENCE: 32

Gln Trp Leu Pro Pro Gly Glu Ser Pro Ala Ile Ser Ser Val Met Phe
1               5                   10                  15

Ser Ala Gly Val Leu Gly Asn Leu Ile Ala Leu Ala Leu Leu Ala Arg
            20                  25                  30

Arg Trp Arg Ser Ala Gly Arg Arg Ser Ser Leu Ser Leu
        35                  40                  45

<210> SEQ ID NO 33
<211> LENGTH: 48
<212> TYPE: PRT
<213> ORGANISM: Artificial Sequence
<220> FEATURE:
<223> OTHER INFORMATION: PGF GPCR TM1

<400> SEQUENCE: 33

Ser Asn Thr Thr Cys Gln Thr Glu Asn Arg Leu Ser Val Phe Phe Ser
1               5                   10                  15

Val Ile Phe Met Thr Val Gly Ile Leu Ser Asn Ser Leu Ala Ile Ala
            20                  25                  30

Ile Leu Met Lys Ala Tyr Gln Arg Phe Arg Gln Lys Ser Lys Ala Ser
        35                  40                  45

<210> SEQ ID NO 34
<211> LENGTH: 44
<212> TYPE: PRT
<213> ORGANISM: Artificial Sequence
<220> FEATURE:
<223> OTHER INFORMATION: PGI GPCR TM1
```

```
<400> SEQUENCE: 34

Cys Arg Asn Leu Thr Tyr Val Arg Gly Ser Val Gly Pro Ala Thr Ser
1               5                   10                  15

Thr Leu Met Phe Val Ala Gly Val Val Gly Asn Gly Leu Ala Leu Gly
            20                  25                  30

Ile Leu Ser Ala Arg Arg Pro Ala Arg Pro Ser Ala
        35                  40

<210> SEQ ID NO 35
<211> LENGTH: 47
<212> TYPE: PRT
<213> ORGANISM: Artificial Sequence
<220> FEATURE:
<223> OTHER INFORMATION: TXA2 GPCR TM1

<400> SEQUENCE: 35

Asn Ile Thr Leu Glu Glu Arg Arg Leu Ile Ala Ser Pro Trp Phe Ala
1               5                   10                  15

Ala Ser Phe Cys Val Val Gly Leu Ala Ser Asn Leu Leu Ala Leu Ser
            20                  25                  30

Val Leu Ala Gly Ala Arg Gln Gly Gly Ser His Thr Arg Ser Ser
        35                  40                  45

<210> SEQ ID NO 36
<211> LENGTH: 46
<212> TYPE: PRT
<213> ORGANISM: Artificial Sequence
<220> FEATURE:
<223> OTHER INFORMATION: PAF GPCR TM1

<400> SEQUENCE: 36

His Met Asp Ser Glu Phe Arg Tyr Thr Leu Phe Pro Ile Val Tyr Ser
1               5                   10                  15

Ile Ile Phe Val Leu Gly Val Ile Ala Asn Gly Tyr Val Leu Trp Val
            20                  25                  30

Phe Ala Arg Leu Tyr Pro Cys Lys Lys Phe Asn Glu Ile Lys
        35                  40                  45

<210> SEQ ID NO 37
<211> LENGTH: 40
<212> TYPE: PRT
<213> ORGANISM: Artificial Sequence
<220> FEATURE:
<223> OTHER INFORMATION: M2 GPCR TM1

<400> SEQUENCE: 37

Tyr Lys Thr Phe Glu Val Val Phe Ile Val Leu Val Ala Gly Ser Leu
1               5                   10                  15

Ser Leu Val Thr Ile Ile Gly Asn Ile Leu Val Met Val Ser Ile Lys
            20                  25                  30

Val Asn Arg His Leu Gln Thr Val
        35                  40

<210> SEQ ID NO 38
<211> LENGTH: 43
<212> TYPE: PRT
<213> ORGANISM: Artificial Sequence
<220> FEATURE:
<223> OTHER INFORMATION: M4 GPCR TM1
```

-continued

<400> SEQUENCE: 38

His Asn Arg Tyr Glu Thr Val Glu Met Val Phe Ile Ala Thr Val Thr
1               5                   10                  15

Gly Ser Leu Ser Leu Val Thr Val Val Gly Asn Ile Leu Val Met Leu
            20                  25                  30

Ser Ile Lys Val Asn Arg Gln Leu Gln Thr Val
        35                  40

<210> SEQ ID NO 39
<211> LENGTH: 41
<212> TYPE: PRT
<213> ORGANISM: Artificial Sequence
<220> FEATURE:
<223> OTHER INFORMATION: M1 GPCR TM1

<400> SEQUENCE: 39

Gly Lys Gly Pro Trp Gln Val Ala Phe Ile Gly Ile Thr Thr Gly Leu
1               5                   10                  15

Leu Ser Leu Ala Thr Val Thr Gly Asn Leu Leu Val Leu Ile Ser Phe
            20                  25                  30

Lys Val Asn Thr Glu Leu Lys Thr Val
        35                  40

<210> SEQ ID NO 40
<211> LENGTH: 43
<212> TYPE: PRT
<213> ORGANISM: Artificial Sequence
<220> FEATURE:
<223> OTHER INFORMATION: M3 GPCR TM1

<400> SEQUENCE: 40

Leu Gly Gly His Thr Val Trp Gln Val Val Phe Ile Ala Phe Leu Thr
1               5                   10                  15

Gly Ile Leu Ala Leu Val Thr Ile Ile Gly Asn Ile Leu Val Ile Val
            20                  25                  30

Ser Phe Lys Val Asn Lys Gln Leu Lys Thr Val
        35                  40

<210> SEQ ID NO 41
<211> LENGTH: 43
<212> TYPE: PRT
<213> ORGANISM: Artificial Sequence
<220> FEATURE:
<223> OTHER INFORMATION: M5 GPCR TM1

<400> SEQUENCE: 41

Leu Glu Arg His Arg Leu Trp Glu Val Ile Thr Ile Ala Ala Val Thr
1               5                   10                  15

Ala Val Val Ser Leu Ile Thr Ile Val Gly Asn Val Leu Val Met Ile
            20                  25                  30

Ser Phe Lys Val Asn Ser Gln Leu Lys Thr Val
        35                  40

<210> SEQ ID NO 42
<211> LENGTH: 43
<212> TYPE: PRT
<213> ORGANISM: Artificial Sequence
<220> FEATURE:
<223> OTHER INFORMATION: H1 GPCR TM1

-continued

```
<400> SEQUENCE: 42

Lys Thr Thr Met Ala Ser Pro Gln Leu Met Pro Leu Val Val Leu
 1               5                  10                  15

Ser Thr Ile Cys Leu Val Thr Val Gly Leu Asn Leu Leu Val Leu Tyr
            20                  25                  30

Ala Val Arg Ser Glu Arg Lys Leu His Thr Val
        35                  40

<210> SEQ ID NO 43
<211> LENGTH: 43
<212> TYPE: PRT
<213> ORGANISM: Artificial Sequence
<220> FEATURE:
<223> OTHER INFORMATION: H2 GPCR TM1

<400> SEQUENCE: 43

Phe Cys Leu Asp Ser Thr Ala Cys Lys Ile Thr Ile Thr Val Val Leu
 1               5                  10                  15

Ala Val Leu Ile Leu Ile Thr Val Ala Gly Asn Val Val Val Cys Leu
            20                  25                  30

Ala Val Gly Leu Asn Arg Arg Leu Arg Asn Leu
        35                  40

<210> SEQ ID NO 44
<211> LENGTH: 43
<212> TYPE: PRT
<213> ORGANISM: Artificial Sequence
<220> FEATURE:
<223> OTHER INFORMATION: 5HT1A GPCR TM1

<400> SEQUENCE: 44

Ile Ser Asp Val Thr Val Ser Tyr Gln Val Ile Thr Ser Leu Leu Leu
 1               5                  10                  15

Gly Thr Leu Ile Phe Cys Ala Val Leu Gly Asn Ala Cys Val Val Ala
            20                  25                  30

Ala Ile Ala Leu Glu Arg Ser Leu Gln Asn Val
        35                  40

<210> SEQ ID NO 45
<211> LENGTH: 43
<212> TYPE: PRT
<213> ORGANISM: Artificial Sequence
<220> FEATURE:
<223> OTHER INFORMATION: 5HT1B GPCR TM1

<400> SEQUENCE: 45

Gln Asp Ser Ile Ser Leu Pro Trp Lys Val Leu Leu Val Met Leu Leu
 1               5                  10                  15

Ala Leu Ile Thr Leu Ala Thr Thr Leu Ser Asn Ala Phe Val Ile Ala
            20                  25                  30

Thr Val Tyr Arg Thr Arg Lys Leu His Thr Pro
        35                  40

<210> SEQ ID NO 46
<211> LENGTH: 43
<212> TYPE: PRT
<213> ORGANISM: Artificial Sequence
<220> FEATURE:
<223> OTHER INFORMATION: 5HT1D GPCR TM1
```

-continued

```
<400> SEQUENCE: 46

Asp Pro Arg Thr Leu Gln Ala Leu Lys Ile Ser Leu Ala Val Val Leu
1               5                   10                  15

Ser Val Ile Thr Leu Ala Thr Val Leu Ser Asn Ala Phe Val Leu Thr
            20                  25                  30

Thr Ile Leu Leu Thr Arg Lys Leu His Thr Pro
        35                  40

<210> SEQ ID NO 47
<211> LENGTH: 43
<212> TYPE: PRT
<213> ORGANISM: Artificial Sequence
<220> FEATURE:
<223> OTHER INFORMATION: 5HT1E GPCR TM1

<400> SEQUENCE: 47

Ile Arg Pro Lys Thr Ile Thr Glu Lys Met Leu Ile Cys Met Thr Leu
1               5                   10                  15

Val Val Ile Thr Thr Leu Thr Thr Leu Leu Asn Leu Ala Val Ile Met
            20                  25                  30

Ala Ile Gly Thr Thr Lys Lys Leu His Gln Pro
        35                  40

<210> SEQ ID NO 48
<211> LENGTH: 43
<212> TYPE: PRT
<213> ORGANISM: Artificial Sequence
<220> FEATURE:
<223> OTHER INFORMATION: 5HT1F GPCR TM1

<400> SEQUENCE: 48

Glu Leu Leu Asn Arg Met Pro Ser Lys Ile Leu Val Ser Leu Thr Leu
1               5                   10                  15

Ser Gly Leu Ala Leu Met Thr Thr Thr Ile Asn Ser Leu Val Ile Ala
            20                  25                  30

Ala Ile Ile Val Thr Arg Lys Leu His His Pro
        35                  40

<210> SEQ ID NO 49
<211> LENGTH: 37
<212> TYPE: PRT
<213> ORGANISM: Artificial Sequence
<220> FEATURE:
<223> OTHER INFORMATION: 5HT2A GPCR TM1

<400> SEQUENCE: 49

Gln Glu Lys Asn Trp Ser Ala Leu Leu Thr Ala Val Val Ile Ile Leu
1               5                   10                  15

Thr Ile Ala Gly Asn Ile Leu Val Ile Met Ala Val Ser Leu Glu Lys
            20                  25                  30

Lys Leu Gln Asn Ala
        35

<210> SEQ ID NO 50
<211> LENGTH: 43
<212> TYPE: PRT
<213> ORGANISM: Artificial Sequence
<220> FEATURE:
<223> OTHER INFORMATION: 5HT2B GPCR TM1
```

-continued

```
<400> SEQUENCE: 50

Ile Val Glu Glu Gln Gly Asn Lys Leu His Trp Ala Ala Leu Leu Ile
1               5                   10                  15

Leu Met Val Ile Ile Pro Thr Ile Gly Gly Asn Thr Leu Val Ile Leu
            20                  25                  30

Ala Val Ser Leu Glu Lys Lys Leu Gln Tyr Ala
        35                  40

<210> SEQ ID NO 51
<211> LENGTH: 35
<212> TYPE: PRT
<213> ORGANISM: Artificial Sequence
<220> FEATURE:
<223> OTHER INFORMATION: 5HT2C GPCR TM1

<400> SEQUENCE: 51

Gln Asn Trp Pro Ala Leu Ser Ile Val Ile Ile Ile Met Thr Ile
1               5                   10                  15

Gly Gly Asn Ile Leu Val Ile Met Ala Val Ser Met Glu Lys Lys Leu
            20                  25                  30

His Asn Ala
        35

<210> SEQ ID NO 52
<211> LENGTH: 43
<212> TYPE: PRT
<213> ORGANISM: Artificial Sequence
<220> FEATURE:
<223> OTHER INFORMATION: 5HT5A GPCR TM1

<400> SEQUENCE: 52

Ser Ser Pro Leu Leu Ser Val Phe Gly Val Leu Ile Leu Thr Leu Leu
1               5                   10                  15

Gly Phe Leu Val Ala Ala Thr Phe Ala Trp Asn Leu Leu Val Leu Ala
            20                  25                  30

Thr Ile Leu Arg Val Arg Thr Phe His Arg Val
        35                  40

<210> SEQ ID NO 53
<211> LENGTH: 43
<212> TYPE: PRT
<213> ORGANISM: Artificial Sequence
<220> FEATURE:
<223> OTHER INFORMATION: 5HT5Brat GPCR TM1

<400> SEQUENCE: 53

Arg Glu Pro Pro Phe Ser Ala Phe Thr Val Leu Val Val Thr Leu Leu
1               5                   10                  15

Val Leu Leu Ile Ala Ala Thr Phe Leu Trp Asn Leu Leu Val Leu Val
            20                  25                  30

Thr Ile Leu Arg Val Arg Ala Phe His Arg Val
        35                  40

<210> SEQ ID NO 54
<211> LENGTH: 43
<212> TYPE: PRT
<213> ORGANISM: Artificial Sequence
<220> FEATURE:
<223> OTHER INFORMATION: 5HT6rat GPCR TM1
```

-continued

```
<400> SEQUENCE: 54

Gly Pro Pro Pro Ala Pro Gly Gly Ser Gly Trp Val Ala Ala Ala Leu
 1               5                  10                  15

Cys Val Val Ile Val Leu Thr Ala Ala Ala Asn Ser Leu Leu Ile Val
             20                  25                  30

Leu Ile Cys Thr Gln Pro Ala Val Arg Asn Thr
         35                  40

<210> SEQ ID NO 55
<211> LENGTH: 43
<212> TYPE: PRT
<213> ORGANISM: Artificial Sequence
<220> FEATURE:
<223> OTHER INFORMATION: 5HT7 GPCR TM1

<400> SEQUENCE: 55

Gln Ile Asn Tyr Gly Arg Val Glu Lys Val Val Ile Gly Ser Ile Leu
 1               5                  10                  15

Thr Leu Ile Thr Leu Leu Thr Ile Ala Gly Asn Cys Leu Val Val Ile
             20                  25                  30

Ser Val Cys Phe Val Lys Lys Leu Arg Gln Pro
         35                  40

<210> SEQ ID NO 56
<211> LENGTH: 43
<212> TYPE: PRT
<213> ORGANISM: Artificial Sequence
<220> FEATURE:
<223> OTHER INFORMATION: alpha1A GPCR TM1

<400> SEQUENCE: 56

Gly Gly Leu Val Val Ser Ala Gln Gly Val Gly Val Gly Val Phe Leu
 1               5                  10                  15

Ala Ala Phe Ile Leu Met Ala Val Ala Gly Asn Leu Leu Val Ile Leu
             20                  25                  30

Ser Val Ala Cys Asn Arg His Leu Gln Thr Val
         35                  40

<210> SEQ ID NO 57
<211> LENGTH: 41
<212> TYPE: PRT
<213> ORGANISM: Artificial Sequence
<220> FEATURE:
<223> OTHER INFORMATION: alpha1B GPCR TM1

<400> SEQUENCE: 57

Gln Leu Asp Ile Thr Arg Ala Ile Ser Val Gly Leu Val Leu Gly Ala
 1               5                  10                  15

Phe Ile Leu Phe Ala Ile Val Gly Asn Ile Leu Val Ile Leu Ser Val
             20                  25                  30

Ala Cys Asn Arg His Leu Arg Thr Pro
         35                  40

<210> SEQ ID NO 58
<211> LENGTH: 43
<212> TYPE: PRT
<213> ORGANISM: Artificial Sequence
<220> FEATURE:
<223> OTHER INFORMATION: alpha1C GPCR TM1
```

```
<400> SEQUENCE: 58

Pro Ala Pro Val Asn Ile Ser Lys Ala Ile Leu Leu Gly Val Ile Leu
 1               5                  10                  15

Gly Gly Leu Ile Leu Phe Gly Val Leu Cys Asn Ile Leu Val Ile Leu
            20                  25                  30

Ser Val Ala Cys His Arg His Leu His Ser Val
        35                  40

<210> SEQ ID NO 59
<211> LENGTH: 40
<212> TYPE: PRT
<213> ORGANISM: Artificial Sequence
<220> FEATURE:
<223> OTHER INFORMATION: alpha2A GPCR TM1

<400> SEQUENCE: 59

Tyr Ser Leu Gln Val Thr Leu Thr Leu Val Cys Leu Ala Gly Leu Leu
 1               5                  10                  15

Met Leu Leu Thr Val Phe Gly Asn Val Leu Val Ile Ile Ala Val Phe
            20                  25                  30

Thr Ser Arg Ala Leu Lys Ala Pro
        35                  40

<210> SEQ ID NO 60
<211> LENGTH: 43
<212> TYPE: PRT
<213> ORGANISM: Artificial Sequence
<220> FEATURE:
<223> OTHER INFORMATION: alpha2B GPCR TM1

<400> SEQUENCE: 60

Gln Asp Pro Tyr Ser Val Gln Ala Thr Ala Ala Ile Ala Ala Ala Ile
 1               5                  10                  15

Thr Phe Leu Ile Leu Phe Thr Ile Phe Gly Asn Ala Leu Val Ile Leu
            20                  25                  30

Ala Val Leu Thr Ser Arg Ser Leu Arg Ala Pro
        35                  40

<210> SEQ ID NO 61
<211> LENGTH: 43
<212> TYPE: PRT
<213> ORGANISM: Artificial Sequence
<220> FEATURE:
<223> OTHER INFORMATION: alpha2C1 and alpha2C2 GPCR TM1

<400> SEQUENCE: 61

Arg Gly Gln Tyr Ser Ala Gly Ala Val Ala Gly Leu Ala Ala Val Val
 1               5                  10                  15

Gly Phe Leu Ile Val Phe Thr Val Val Gly Asn Val Leu Val Val Ile
            20                  25                  30

Ala Val Leu Thr Ser Arg Ala Leu Arg Ala Pro
        35                  40

<210> SEQ ID NO 62
<211> LENGTH: 42
<212> TYPE: PRT
<213> ORGANISM: Artificial Sequence
<220> FEATURE:
<223> OTHER INFORMATION: beta1 GPCR TM1
```

-continued

```
<400> SEQUENCE: 62

Glu Pro Leu Ser Gln Gln Trp Thr Ala Gly Met Gly Leu Leu Met Ala
 1               5                  10                  15

Leu Ile Val Leu Leu Ile Val Ala Gly Asn Val Leu Val Ile Val Ala
            20                  25                  30

Ile Ala Lys Thr Pro Arg Leu Gln Thr Leu
            35                  40

<210> SEQ ID NO 63
<211> LENGTH: 42
<212> TYPE: PRT
<213> ORGANISM: Artificial Sequence
<220> FEATURE:
<223> OTHER INFORMATION: beta2 GPCR TM1

<400> SEQUENCE: 63

Gln Gln Arg Asp Glu Val Trp Val Val Gly Met Gly Ile Val Met Ser
 1               5                  10                  15

Leu Ile Val Leu Ala Ile Val Phe Gly Asn Val Leu Val Ile Thr Ala
            20                  25                  30

Ile Ala Lys Phe Glu Arg Leu Gln Thr Val
            35                  40

<210> SEQ ID NO 64
<211> LENGTH: 43
<212> TYPE: PRT
<213> ORGANISM: Artificial Sequence
<220> FEATURE:
<223> OTHER INFORMATION: beta3 GPCR TM1

<400> SEQUENCE: 64

Gly Leu Pro Gly Val Pro Trp Glu Ala Ala Leu Ala Gly Ala Leu Leu
 1               5                  10                  15

Ala Leu Ala Val Leu Ala Thr Val Gly Gly Asn Leu Leu Val Ile Val
            20                  25                  30

Ala Ile Ala Trp Thr Pro Arg Leu Gln Thr Met
            35                  40

<210> SEQ ID NO 65
<211> LENGTH: 43
<212> TYPE: PRT
<213> ORGANISM: Artificial Sequence
<220> FEATURE:
<223> OTHER INFORMATION: beta4turkey GPCR TM1

<400> SEQUENCE: 65

Ser Trp Ala Ala Val Leu Ser Arg Gln Trp Ala Val Gly Ala Ala Leu
 1               5                  10                  15

Ser Ile Thr Ile Leu Val Ile Val Ala Gly Asn Leu Leu Val Ile Val
            20                  25                  30

Ala Ile Ala Lys Thr Pro Arg Leu Gln Thr Met
            35                  40

<210> SEQ ID NO 66
<211> LENGTH: 44
<212> TYPE: PRT
<213> ORGANISM: Artificial Sequence
<220> FEATURE:
<223> OTHER INFORMATION: D1A GPCR TM1
```

-continued

```
<400> SEQUENCE: 66

Val Val Glu Arg Asp Phe Ser Val Arg Ile Leu Thr Ala Cys Phe Leu
1               5                   10                  15

Ser Leu Leu Ile Leu Ser Thr Leu Leu Gly Asn Thr Leu Val Cys Ala
            20                  25                  30

Ala Val Ile Arg Phe Arg His Leu Arg Ser Lys Val
        35                  40

<210> SEQ ID NO 67
<211> LENGTH: 43
<212> TYPE: PRT
<213> ORGANISM: Artificial Sequence
<220> FEATURE:
<223> OTHER INFORMATION: D2 GPCR TM1

<400> SEQUENCE: 67

Asp Gly Lys Ala Asp Arg Pro His Tyr Asn Tyr Tyr Ala Thr Leu Leu
1               5                   10                  15

Thr Leu Leu Ile Ala Val Ile Val Phe Gly Asn Val Leu Val Cys Met
            20                  25                  30

Ala Val Ser Arg Glu Lys Ala Leu Gln Thr Thr
        35                  40

<210> SEQ ID NO 68
<211> LENGTH: 43
<212> TYPE: PRT
<213> ORGANISM: Artificial Sequence
<220> FEATURE:
<223> OTHER INFORMATION: D3 GPCR TM1

<400> SEQUENCE: 68

Thr Gly Ala Ser Gln Ala Arg Pro His Ala Tyr Tyr Ala Leu Ser Tyr
1               5                   10                  15

Cys Ala Leu Ile Leu Ala Ile Val Phe Gly Asn Gly Leu Val Cys Met
            20                  25                  30

Ala Val Leu Lys Glu Arg Ala Leu Gln Thr Thr
        35                  40

<210> SEQ ID NO 69
<211> LENGTH: 43
<212> TYPE: PRT
<213> ORGANISM: Artificial Sequence
<220> FEATURE:
<223> OTHER INFORMATION: D4 GPCR TM1

<400> SEQUENCE: 69

Ala Ser Ala Gly Leu Ala Gly Gln Gly Ala Ala Ala Leu Val Gly Gly
1               5                   10                  15

Val Leu Leu Ile Gly Ala Val Leu Ala Gly Asn Ser Leu Val Cys Val
            20                  25                  30

Ser Val Ala Thr Glu Arg Ala Leu Gln Thr Pro
        35                  40

<210> SEQ ID NO 70
<211> LENGTH: 44
<212> TYPE: PRT
<213> ORGANISM: Artificial Sequence
<220> FEATURE:
<223> OTHER INFORMATION: D5 GPCR TM1
```

```
<400> SEQUENCE: 70

Gly Ala Pro Pro Leu Gly Pro Ser Gln Val Val Thr Ala Cys Leu Leu
 1               5                  10                  15

Thr Leu Leu Ile Ile Trp Thr Leu Leu Gly Asn Val Leu Val Cys Ala
            20                  25                  30

Ala Ile Val Arg Ser Arg His Leu Arg Ala Asn Met
        35                  40

<210> SEQ ID NO 71
<211> LENGTH: 43
<212> TYPE: PRT
<213> ORGANISM: Artificial Sequence
<220> FEATURE:
<223> OTHER INFORMATION: A1 GPCR TM1

<400> SEQUENCE: 71

Met Pro Pro Ser Ile Ser Ala Phe Gln Ala Ala Tyr Ile Gly Ile Glu
 1               5                  10                  15

Val Leu Ile Ala Leu Val Ser Val Pro Gly Asn Val Leu Val Ile Trp
            20                  25                  30

Ala Val Lys Val Asn Gln Ala Leu Arg Asp Ala
        35                  40

<210> SEQ ID NO 72
<211> LENGTH: 40
<212> TYPE: PRT
<213> ORGANISM: Artificial Sequence
<220> FEATURE:
<223> OTHER INFORMATION: A2a GPCR TM1

<400> SEQUENCE: 72

Met Pro Ile Met Gly Ser Ser Val Tyr Ile Thr Val Glu Leu Ala Ile
 1               5                  10                  15

Ala Val Leu Ala Ile Leu Gly Asn Val Leu Val Cys Trp Ala Val Trp
            20                  25                  30

Leu Asn Ser Asn Leu Gln Asn Val
        35                  40

<210> SEQ ID NO 73
<211> LENGTH: 41
<212> TYPE: PRT
<213> ORGANISM: Artificial Sequence
<220> FEATURE:
<223> OTHER INFORMATION: A2b GPCR TM1

<400> SEQUENCE: 73

Met Leu Leu Glu Thr Gln Asp Ala Leu Tyr Val Ala Leu Glu Leu Val
 1               5                  10                  15

Ile Ala Ala Leu Ser Val Ala Gly Asn Val Leu Val Cys Ala Ala Val
            20                  25                  30

Gly Thr Ala Asn Thr Leu Gln Thr Pro
        35                  40

<210> SEQ ID NO 74
<211> LENGTH: 43
<212> TYPE: PRT
<213> ORGANISM: Artificial Sequence
<220> FEATURE:
<223> OTHER INFORMATION: A3 GPCR TM1
```

-continued

```
<400> SEQUENCE: 74

Asn Ser Thr Thr Leu Ser Leu Ala Asn Val Thr Tyr Ile Thr Met Glu
1               5                   10                  15

Ile Phe Ile Gly Leu Cys Ala Ile Val Gly Asn Val Leu Val Ile Cys
            20                  25                  30

Val Val Lys Leu Asn Pro Ser Leu Gln Thr Thr
        35                  40

<210> SEQ ID NO 75
<211> LENGTH: 42
<212> TYPE: PRT
<213> ORGANISM: Artificial Sequence
<220> FEATURE:
<223> OTHER INFORMATION: OCdrome GPCR TM1

<400> SEQUENCE: 75

Leu Ala Val Pro Glu Trp Glu Ala Leu Leu Thr Ala Leu Val Leu Ser
1               5                   10                  15

Val Ile Ile Val Leu Thr Ile Ile Gly Asn Ile Leu Val Ile Leu Ser
            20                  25                  30

Val Phe Thr Tyr Lys Pro Leu Arg Ile Val
        35                  40

<210> SEQ ID NO 76
<211> LENGTH: 43
<212> TYPE: PRT
<213> ORGANISM: Artificial Sequence
<220> FEATURE:
<223> OTHER INFORMATION: ACTH GPCR TM1

<400> SEQUENCE: 76

Arg Asn Asn Ser Asp Cys Pro Arg Val Val Leu Pro Glu Glu Ile Phe
1               5                   10                  15

Phe Thr Ile Ser Ile Val Gly Val Leu Glu Asn Leu Ile Val Leu Leu
            20                  25                  30

Ala Val Phe Lys Asn Lys Asn Leu Gln Ala Pro
        35                  40

<210> SEQ ID NO 77
<211> LENGTH: 43
<212> TYPE: PRT
<213> ORGANISM: Artificial Sequence
<220> FEATURE:
<223> OTHER INFORMATION: MSH GPCR TM1

<400> SEQUENCE: 77

Gln Thr Gly Ala Arg Cys Leu Glu Val Ser Ile Ser Asp Gly Leu Phe
1               5                   10                  15

Leu Ser Leu Gly Leu Val Ser Leu Val Glu Asn Ala Leu Val Val Ala
            20                  25                  30

Thr Ile Ala Lys Asn Arg Asn Leu His Ser Pro
        35                  40

<210> SEQ ID NO 78
<211> LENGTH: 43
<212> TYPE: PRT
<213> ORGANISM: Artificial Sequence
<220> FEATURE:
<223> OTHER INFORMATION: MC3 GPCR TM1
```

-continued

```
<400> SEQUENCE: 78

Ser Ser Ser Ala Phe Cys Glu Gln Val Phe Ile Lys Pro Glu Ile Phe
1               5                   10                  15

Leu Ser Leu Gly Ile Val Ser Leu Leu Glu Asn Ile Leu Val Ile Leu
            20                  25                  30

Ala Val Val Arg Asn Gly Asn Leu His Ser Pro
        35                  40

<210> SEQ ID NO 79
<211> LENGTH: 43
<212> TYPE: PRT
<213> ORGANISM: Artificial Sequence
<220> FEATURE:
<223> OTHER INFORMATION: MC4 GPCR TM1

<400> SEQUENCE: 79

Ser Asp Gly Gly Cys Tyr Glu Gln Leu Phe Val Ser Pro Glu Val Phe
1               5                   10                  15

Val Thr Leu Gly Val Ile Ser Leu Leu Glu Asn Ile Leu Val Ile Val
            20                  25                  30

Ala Ile Ala Lys Asn Lys Asn Leu His Ser Pro
        35                  40

<210> SEQ ID NO 80
<211> LENGTH: 43
<212> TYPE: PRT
<213> ORGANISM: Artificial Sequence
<220> FEATURE:
<223> OTHER INFORMATION: MC5 GPCR TM1

<400> SEQUENCE: 80

Asn Lys Ser Ser Pro Cys Glu Asp Met Gly Ile Ala Val Glu Val Phe
1               5                   10                  15

Leu Thr Leu Gly Val Ile Ser Leu Leu Glu Asn Ile Leu Val Ile Gly
            20                  25                  30

Ala Ile Val Lys Asn Lys Asn Leu His Ser Pro
        35                  40

<210> SEQ ID NO 81
<211> LENGTH: 43
<212> TYPE: PRT
<213> ORGANISM: Artificial Sequence
<220> FEATURE:
<223> OTHER INFORMATION: melatonin GPCR TM1

<400> SEQUENCE: 81

Asp Gly Ala Arg Pro Ser Trp Leu Ala Ser Ala Leu Ala Cys Val Leu
1               5                   10                  15

Ile Phe Thr Ile Val Val Asp Ile Leu Gly Asn Leu Leu Val Ile Leu
            20                  25                  30

Ser Val Tyr Arg Asn Lys Lys Leu Arg Asn Ala
        35                  40

<210> SEQ ID NO 82
<211> LENGTH: 41
<212> TYPE: PRT
<213> ORGANISM: Artificial Sequence
<220> FEATURE:
<223> OTHER INFORMATION: oxytocin GPCR TM1
```

<400> SEQUENCE: 82

Arg Arg Asn Glu Ala Leu Ala Arg Val Glu Val Ala Val Leu Cys Leu
1               5                   10                  15

Ile Leu Leu Leu Ala Leu Ser Gly Asn Ala Cys Val Leu Leu Ala Leu
                20                  25                  30

Arg Thr Thr Arg Gln Lys His Ser Arg
            35                  40

<210> SEQ ID NO 83
<211> LENGTH: 43
<212> TYPE: PRT
<213> ORGANISM: Artificial Sequence
<220> FEATURE:
<223> OTHER INFORMATION: conopressinLs GPCR TM1

<400> SEQUENCE: 83

Phe His Gly Val Asp Glu Asp Leu Leu Lys Ile Glu Ile Ala Val Gln
1               5                   10                  15

Ala Thr Ile Leu Tyr Met Thr Leu Phe Gly Asn Gly Ile Val Leu Leu
                20                  25                  30

Val Leu Arg Leu Arg Arg Gln Lys Leu Thr Arg
            35                  40

<210> SEQ ID NO 84
<211> LENGTH: 43
<212> TYPE: PRT
<213> ORGANISM: Artificial Sequence
<220> FEATURE:
<223> OTHER INFORMATION: V1A GPCR TM1

<400> SEQUENCE: 84

Arg Asp Val Arg Asn Glu Glu Leu Ala Lys Leu Glu Ile Ala Val Leu
1               5                   10                  15

Ala Val Thr Phe Ala Val Ala Val Leu Gly Asn Ser Ser Val Leu Leu
                20                  25                  30

Ala Leu His Arg Thr Pro Arg Lys Thr Ser Arg
            35                  40

<210> SEQ ID NO 85
<211> LENGTH: 43
<212> TYPE: PRT
<213> ORGANISM: Artificial Sequence
<220> FEATURE:
<223> OTHER INFORMATION: V1B GPCR TM1

<400> SEQUENCE: 85

Trp Leu Gly Arg Asp Glu Glu Leu Ala Lys Val Glu Ile Gly Val Leu
1               5                   10                  15

Ala Thr Val Leu Val Leu Ala Thr Gly Gly Asn Leu Ala Val Leu Leu
                20                  25                  30

Thr Leu Gly Gln Leu Gly Arg Lys Arg Ser Arg
            35                  40

<210> SEQ ID NO 86
<211> LENGTH: 45
<212> TYPE: PRT
<213> ORGANISM: Artificial Sequence
<220> FEATURE:
<223> OTHER INFORMATION: V2 GPCR TM1

```
<400> SEQUENCE: 86

Leu Asp Thr Arg Asp Pro Leu Leu Ala Arg Ala Glu Leu Ala Leu Leu
  1               5                  10                  15

Ser Ile Val Phe Val Ala Val Ala Leu Ser Asn Gly Leu Val Leu Ala
             20                  25                  30

Ala Leu Ala Arg Arg Gly Arg Gly His Trp Ala Pro
         35                  40              45

<210> SEQ ID NO 87
<211> LENGTH: 43
<212> TYPE: PRT
<213> ORGANISM: Artificial Sequence
<220> FEATURE:
<223> OTHER INFORMATION: CCK_A GPCR TM1

<400> SEQUENCE: 87

Pro Arg Pro Ser Lys Glu Trp Gln Pro Ala Val Gln Ile Leu Leu Tyr
  1               5                  10                  15

Ser Leu Ile Phe Leu Leu Ser Val Leu Gly Asn Thr Leu Val Ile Thr
             20                  25                  30

Val Leu Ile Arg Asn Lys Arg Met Arg Thr Val
         35                  40

<210> SEQ ID NO 88
<211> LENGTH: 43
<212> TYPE: PRT
<213> ORGANISM: Artificial Sequence
<220> FEATURE:
<223> OTHER INFORMATION: CCK_B GPCR TM1

<400> SEQUENCE: 88

Gly Ala Gly Thr Arg Glu Leu Glu Leu Ala Ile Arg Ile Thr Leu Tyr
  1               5                  10                  15

Ala Val Ile Phe Leu Met Ser Val Gly Gly Asn Met Leu Ile Ile Val
             20                  25                  30

Val Leu Gly Leu Ser Arg Arg Leu Arg Thr Val
         35                  40

<210> SEQ ID NO 89
<211> LENGTH: 43
<212> TYPE: PRT
<213> ORGANISM: Artificial Sequence
<220> FEATURE:
<223> OTHER INFORMATION: NPY1 GPCR TM1

<400> SEQUENCE: 89

Asp Cys His Leu Pro Leu Ala Met Ile Phe Thr Leu Ala Leu Ala Tyr
  1               5                  10                  15

Gly Ala Val Ile Ile Leu Gly Val Ser Gly Asn Leu Ala Leu Ile Ile
             20                  25                  30

Ile Ile Leu Lys Gln Lys Glu Met Arg Asn Val
         35                  40

<210> SEQ ID NO 90
<211> LENGTH: 46
<212> TYPE: PRT
<213> ORGANISM: Artificial Sequence
<220> FEATURE:
<223> OTHER INFORMATION: NTR GPCR TM1
```

-continued

```
<400> SEQUENCE: 90

Asp Val Asn Thr Asp Ile Tyr Ser Lys Val Leu Val Thr Ala Val Tyr
1               5                   10                  15

Leu Ala Leu Phe Val Val Gly Thr Val Gly Asn Thr Val Thr Ala Phe
                20                  25                  30

Thr Leu Ala Arg Lys Lys Ser Leu Gln Ser Leu Gln Ser Thr
                35                  40                  45

<210> SEQ ID NO 91
<211> LENGTH: 43
<212> TYPE: PRT
<213> ORGANISM: Artificial Sequence
<220> FEATURE:
<223> OTHER INFORMATION: NK1 GPCR TM1

<400> SEQUENCE: 91

Gln Phe Val Gln Pro Ala Trp Gln Ile Val Leu Trp Ala Ala Ala Tyr
1               5                   10                  15

Thr Val Ile Val Val Thr Ser Val Val Gly Asn Val Val Val Met Trp
                20                  25                  30

Ile Ile Leu Ala His Lys Arg Met Arg Thr Val
                35                  40

<210> SEQ ID NO 92
<211> LENGTH: 43
<212> TYPE: PRT
<213> ORGANISM: Artificial Sequence
<220> FEATURE:
<223> OTHER INFORMATION: NK2 GPCR TM1

<400> SEQUENCE: 92

Ala Phe Ser Met Pro Ser Trp Gln Leu Ala Leu Trp Ala Pro Ala Tyr
1               5                   10                  15

Leu Ala Leu Val Leu Val Ala Val Thr Gly Asn Ala Ile Val Ile Trp
                20                  25                  30

Ile Ile Leu Ala His Arg Arg Met Arg Thr Val
                35                  40

<210> SEQ ID NO 93
<211> LENGTH: 43
<212> TYPE: PRT
<213> ORGANISM: Artificial Sequence
<220> FEATURE:
<223> OTHER INFORMATION: NK3 GPCR TM1

<400> SEQUENCE: 93

Gln Phe Val Gln Pro Ser Trp Arg Ile Ala Leu Trp Ser Leu Ala Tyr
1               5                   10                  15

Gly Val Val Val Ala Val Ala Val Leu Gly Asn Leu Ile Val Ile Trp
                20                  25                  30

Ile Ile Leu Ala His Lys Arg Met Arg Thr Val
                35                  40

<210> SEQ ID NO 94
<211> LENGTH: 43
<212> TYPE: PRT
<213> ORGANISM: Artificial Sequence
<220> FEATURE:
<223> OTHER INFORMATION: blueops GPCR TM1
```

```
<400> SEQUENCE: 94

Tyr His Ile Ala Pro Val Trp Ala Phe Tyr Leu Gln Ala Ala Phe Met
1               5                   10                  15

Gly Thr Val Phe Leu Ile Gly Phe Pro Leu Asn Ala Met Val Leu Val
            20                  25                  30

Ala Thr Leu Arg Tyr Lys Lys Leu Arg Gln Pro
        35                  40

<210> SEQ ID NO 95
<211> LENGTH: 43
<212> TYPE: PRT
<213> ORGANISM: Artificial Sequence
<220> FEATURE:
<223> OTHER INFORMATION: greenops GPCR TM1

<400> SEQUENCE: 95

Tyr His Ile Ala Pro Arg Trp Val Tyr His Leu Thr Ser Val Trp Met
1               5                   10                  15

Ile Phe Val Val Ile Ala Ser Val Phe Thr Asn Gly Leu Val Leu Ala
            20                  25                  30

Ala Thr Met Lys Phe Lys Lys Leu Arg His Pro
        35                  40

<210> SEQ ID NO 96
<211> LENGTH: 43
<212> TYPE: PRT
<213> ORGANISM: Artificial Sequence
<220> FEATURE:
<223> OTHER INFORMATION: redops GPCR TM1

<400> SEQUENCE: 96

Tyr His Ile Ala Pro Arg Trp Val Tyr His Leu Thr Ser Val Trp Met
1               5                   10                  15

Ile Phe Val Val Thr Ala Ser Val Phe Thr Asn Gly Leu Val Leu Ala
            20                  25                  30

Ala Thr Met Lys Phe Lys Lys Leu Arg His Pro
        35                  40

<210> SEQ ID NO 97
<211> LENGTH: 43
<212> TYPE: PRT
<213> ORGANISM: Artificial Sequence
<220> FEATURE:
<223> OTHER INFORMATION: rhodopsin GPCR TM1

<400> SEQUENCE: 97

Tyr Tyr Leu Ala Glu Pro Trp Gln Phe Ser Met Leu Ala Ala Tyr Met
1               5                   10                  15

Phe Leu Leu Ile Val Leu Gly Phe Pro Ile Asn Phe Leu Thr Leu Tyr
            20                  25                  30

Val Thr Val Gln His Lys Lys Leu Arg Thr Pro
        35                  40

<210> SEQ ID NO 98
<211> LENGTH: 43
<212> TYPE: PRT
<213> ORGANISM: Artificial Sequence
<220> FEATURE:
<223> OTHER INFORMATION: violetopsGg GPCR TM1
```

```
<400> SEQUENCE: 98

Tyr His Ile Ala Pro Pro Trp Ala Phe Tyr Leu Gln Thr Ala Phe Met
1               5                   10                  15

Gly Ile Val Phe Ala Val Gly Thr Pro Leu Asn Ala Val Val Leu Trp
            20                  25                  30

Val Thr Val Arg Tyr Lys Arg Leu Arg Gln Pro
        35                  40

<210> SEQ ID NO 99
<211> LENGTH: 43
<212> TYPE: PRT
<213> ORGANISM: Artificial Sequence
<220> FEATURE:
<223> OTHER INFORMATION: opsin_crab GPCR TM1

<400> SEQUENCE: 99

Phe Pro Pro Met Asn Pro Leu Trp Tyr Ser Ile Leu Gly Val Ala Met
1               5                   10                  15

Ile Ile Leu Gly Ile Ile Cys Val Leu Gly Asn Gly Met Val Ile Tyr
            20                  25                  30

Leu Met Met Thr Thr Lys Ser Leu Arg Thr Pro
        35                  40

<210> SEQ ID NO 100
<211> LENGTH: 43
<212> TYPE: PRT
<213> ORGANISM: Artificial Sequence
<220> FEATURE:
<223> OTHER INFORMATION: ET_Aprec GPCR TM1

<400> SEQUENCE: 100

Gln Thr Lys Ile Thr Ser Ala Phe Lys Tyr Ile Asn Thr Val Ile Ser
1               5                   10                  15

Cys Thr Ile Phe Ile Val Gly Met Val Gly Asn Ala Thr Leu Leu Arg
            20                  25                  30

Ile Ile Tyr Gln Asn Lys Cys Met Arg Asn Gly
        35                  40

<210> SEQ ID NO 101
<211> LENGTH: 43
<212> TYPE: PRT
<213> ORGANISM: Artificial Sequence
<220> FEATURE:
<223> OTHER INFORMATION: ET_Bprec GPCR TM1

<400> SEQUENCE: 101

Pro Ile Glu Ile Lys Glu Thr Phe Lys Tyr Ile Asn Thr Val Val Ser
1               5                   10                  15

Cys Leu Val Phe Val Leu Gly Ile Ile Gly Asn Ser Thr Leu Leu Arg
            20                  25                  30

Ile Ile Tyr Lys Asn Lys Cys Met Arg Asn Gly
        35                  40

<210> SEQ ID NO 102
<211> LENGTH: 43
<212> TYPE: PRT
<213> ORGANISM: Artificial Sequence
<220> FEATURE:
<223> OTHER INFORMATION: ET_Cfrog GPCR TM1
```

```
<400> SEQUENCE: 102

Arg Ala Lys Ile Arg His Ala Phe Lys Tyr Val Thr Thr Ile Leu Ser
  1               5                  10                  15

Cys Val Ile Phe Leu Val Gly Ile Val Gly Asn Ser Thr Leu Leu Arg
             20                  25                  30

Ile Ile Tyr Lys Asn Lys Cys Met Arg Asn Gly
         35                  40

<210> SEQ ID NO 103
<211> LENGTH: 45
<212> TYPE: PRT
<213> ORGANISM: Artificial Sequence
<220> FEATURE:
<223> OTHER INFORMATION: galanin GPCR TM1

<400> SEQUENCE: 103

Pro Leu Phe Gly Ile Gly Val Glu Asn Phe Val Thr Leu Val Val Phe
  1               5                  10                  15

Gly Leu Ile Phe Ala Leu Gly Val Leu Gly Asn Ser Leu Val Ile Thr
             20                  25                  30

Val Leu Ala Arg Ser Lys Pro Gly Lys Pro Arg Ser Thr
         35                  40                  45

<210> SEQ ID NO 104
<211> LENGTH: 43
<212> TYPE: PRT
<213> ORGANISM: Artificial Sequence
<220> FEATURE:
<223> OTHER INFORMATION: NMB GPCR TM1

<400> SEQUENCE: 104

Gly Thr Thr Thr Glu Leu Val Ile Arg Cys Val Ile Pro Ser Leu Tyr
  1               5                  10                  15

Leu Leu Ile Ile Thr Val Gly Leu Leu Gly Asn Ile Met Leu Val Lys
             20                  25                  30

Ile Phe Ile Thr Asn Ser Ala Met Arg Ser Val
         35                  40

<210> SEQ ID NO 105
<211> LENGTH: 43
<212> TYPE: PRT
<213> ORGANISM: Artificial Sequence
<220> FEATURE:
<223> OTHER INFORMATION: GRP GPCR TM1

<400> SEQUENCE: 105

Asp Asp Trp Ser His Pro Gly Ile Leu Tyr Val Ile Pro Ala Val Tyr
  1               5                  10                  15

Gly Val Ile Ile Leu Ile Gly Leu Ile Gly Asn Ile Thr Leu Ile Lys
             20                  25                  30

Ile Phe Cys Thr Val Lys Ser Met Arg Asn Val
         35                  40

<210> SEQ ID NO 106
<211> LENGTH: 43
<212> TYPE: PRT
<213> ORGANISM: Artificial Sequence
<220> FEATURE:
<223> OTHER INFORMATION: BRS3 GPCR TM1
```

-continued

```
<400> SEQUENCE: 106

Asp Asn Ser Pro Gly Ile Glu Ala Leu Cys Ala Ile Tyr Ile Thr Tyr
1               5                   10                  15

Ala Val Ile Ile Ser Val Gly Ile Leu Gly Asn Ala Ile Leu Ile Lys
            20                  25                  30

Val Phe Phe Lys Thr Lys Ser Met Gln Thr Val
        35                  40

<210> SEQ ID NO 107
<211> LENGTH: 43
<212> TYPE: PRT
<213> ORGANISM: Artificial Sequence
<220> FEATURE:
<223> OTHER INFORMATION: deltaOP GPCR TM1

<400> SEQUENCE: 107

Gly Ser Ala Ser Ser Leu Ala Leu Ala Ile Ala Ile Thr Ala Leu Tyr
1               5                   10                  15

Ser Ala Val Cys Ala Val Gly Leu Leu Gly Asn Val Leu Val Met Phe
            20                  25                  30

Gly Ile Val Arg Tyr Thr Lys Met Lys Thr Ala
        35                  40

<210> SEQ ID NO 108
<211> LENGTH: 43
<212> TYPE: PRT
<213> ORGANISM: Artificial Sequence
<220> FEATURE:
<223> OTHER INFORMATION: kappaOP GPCR TM1

<400> SEQUENCE: 108

Pro Ala His Ile Ser Pro Ala Ile Pro Val Ile Ile Thr Ala Val Tyr
1               5                   10                  15

Ser Val Val Phe Val Val Gly Leu Val Gly Asn Ser Leu Val Met Phe
            20                  25                  30

Val Ile Ile Arg Tyr Thr Lys Met Lys Thr Ala
        35                  40

<210> SEQ ID NO 109
<211> LENGTH: 42
<212> TYPE: PRT
<213> ORGANISM: Artificial Sequence
<220> FEATURE:
<223> OTHER INFORMATION: muOP GPCR TM1

<400> SEQUENCE: 109

Gly Ser Pro Ser Met Ile Thr Ala Ile Thr Ile Met Ala Leu Tyr Ser
1               5                   10                  15

Ile Val Cys Val Val Gly Leu Phe Gly Asn Phe Leu Val Met Tyr Val
            20                  25                  30

Ile Val Arg Tyr Thr Lys Met Lys Thr Ala
        35                  40

<210> SEQ ID NO 110
<211> LENGTH: 43
<212> TYPE: PRT
<213> ORGANISM: Artificial Sequence
<220> FEATURE:
<223> OTHER INFORMATION: OPRX GPCR TM1
```

-continued

```
<400> SEQUENCE: 110

Gly Ala Phe Leu Pro Leu Gly Leu Lys Val Thr Ile Val Gly Leu Tyr
  1               5                  10                  15

Leu Ala Val Cys Val Gly Gly Leu Leu Gly Asn Cys Leu Val Met Tyr
             20                  25                  30

Val Ile Leu Arg His Thr Lys Met Lys Thr Ala
         35                  40

<210> SEQ ID NO 111
<211> LENGTH: 44
<212> TYPE: PRT
<213> ORGANISM: Artificial Sequence
<220> FEATURE:
<223> OTHER INFORMATION: CB1 GPCR TM1

<400> SEQUENCE: 111

Phe Met Val Leu Asn Pro Ser Gln Gln Leu Ala Ile Ala Val Leu Ser
  1               5                  10                  15

Leu Thr Leu Gly Thr Phe Thr Val Leu Glu Asn Leu Leu Val Leu Cys
             20                  25                  30

Val Ile Leu His Ser Arg Ser Leu Arg Cys Arg Pro
         35                  40

<210> SEQ ID NO 112
<211> LENGTH: 44
<212> TYPE: PRT
<213> ORGANISM: Artificial Sequence
<220> FEATURE:
<223> OTHER INFORMATION: CB2 GPCR TM1

<400> SEQUENCE: 112

Tyr Met Ile Leu Ser Gly Pro Gln Lys Thr Ala Val Ala Val Leu Cys
  1               5                  10                  15

Thr Leu Leu Gly Leu Leu Ser Ala Leu Glu Asn Val Ala Val Leu Tyr
             20                  25                  30

Leu Ile Leu Ser Ser His Gln Leu Arg Arg Lys Pro
         35                  40

<210> SEQ ID NO 113
<211> LENGTH: 43
<212> TYPE: PRT
<213> ORGANISM: Artificial Sequence
<220> FEATURE:
<223> OTHER INFORMATION: SSTR1 GPCR TM1

<400> SEQUENCE: 113

Thr Leu Ser Glu Gly Gln Gly Ser Ala Ile Leu Ile Ser Phe Ile Tyr
  1               5                  10                  15

Ser Val Val Cys Leu Val Gly Leu Cys Gly Asn Ser Met Val Ile Tyr
             20                  25                  30

Val Ile Leu Arg Tyr Ala Lys Met Lys Thr Ala
         35                  40

<210> SEQ ID NO 114
<211> LENGTH: 43
<212> TYPE: PRT
<213> ORGANISM: Artificial Sequence
<220> FEATURE:
<223> OTHER INFORMATION: SSTR2 GPCR TM1
```

-continued

```
<400> SEQUENCE: 114

Glu Pro Tyr Tyr Asp Leu Thr Ser Asn Ala Val Leu Thr Phe Ile Tyr
 1               5                  10                  15

Phe Val Val Cys Ile Ile Gly Leu Cys Gly Asn Thr Leu Val Ile Tyr
                20                  25                  30

Val Ile Leu Arg Tyr Ala Lys Met Lys Thr Ile
            35                  40

<210> SEQ ID NO 115
<211> LENGTH: 43
<212> TYPE: PRT
<213> ORGANISM: Artificial Sequence
<220> FEATURE:
<223> OTHER INFORMATION: SSTR3 GPCR TM1

<400> SEQUENCE: 115

Ser Pro Ala Gly Leu Ala Val Ser Gly Val Leu Ile Pro Leu Val Tyr
 1               5                  10                  15

Leu Val Val Cys Val Val Gly Leu Leu Gly Asn Ser Leu Val Ile Tyr
                20                  25                  30

Val Val Leu Arg His Thr Ala Ser Pro Ser Val
            35                  40

<210> SEQ ID NO 116
<211> LENGTH: 42
<212> TYPE: PRT
<213> ORGANISM: Artificial Sequence
<220> FEATURE:
<223> OTHER INFORMATION: SSTR4 GPCR TM1

<400> SEQUENCE: 116

Gly Asp Ala Arg Ala Ala Gly Met Val Ala Ile Gln Cys Ile Tyr Ala
 1               5                  10                  15

Leu Val Cys Leu Val Gly Leu Val Gly Asn Ala Leu Val Ile Phe Val
                20                  25                  30

Ile Leu Arg Tyr Ala Lys Met Lys Thr Ala
            35                  40

<210> SEQ ID NO 117
<211> LENGTH: 43
<212> TYPE: PRT
<213> ORGANISM: Artificial Sequence
<220> FEATURE:
<223> OTHER INFORMATION: SSTR5 GPCR TM1

<400> SEQUENCE: 117

Pro Ala Pro Ser Ala Gly Ala Arg Ala Val Leu Val Pro Val Leu Tyr
 1               5                  10                  15

Leu Leu Val Cys Ala Ala Gly Leu Gly Gly Asn Thr Leu Val Ile Tyr
                20                  25                  30

Val Val Leu Arg Phe Ala Lys Met Lys Thr Val
            35                  40

<210> SEQ ID NO 118
<211> LENGTH: 43
<212> TYPE: PRT
<213> ORGANISM: Artificial Sequence
<220> FEATURE:
<223> OTHER INFORMATION: IL8A GPCR TM1
```

-continued

```
<400> SEQUENCE: 118

Met Leu Glu Thr Glu Thr Leu Asn Lys Tyr Val Val Ile Ile Ala Tyr
 1               5                   10                  15

Ala Leu Val Phe Leu Leu Ser Leu Leu Gly Asn Ser Leu Val Met Leu
            20                  25                  30

Val Ile Leu Tyr Ser Arg Val Gly Arg Ser Val
        35                  40

<210> SEQ ID NO 119
<211> LENGTH: 43
<212> TYPE: PRT
<213> ORGANISM: Artificial Sequence
<220> FEATURE:
<223> OTHER INFORMATION: IL8B GPCR TM1

<400> SEQUENCE: 119

Glu Pro Glu Ser Leu Glu Ile Asn Lys Tyr Phe Val Val Ile Ile Tyr
 1               5                   10                  15

Ala Leu Val Phe Leu Leu Ser Leu Leu Gly Asn Ser Leu Val Met Leu
            20                  25                  30

Val Ile Leu Tyr Ser Arg Val Gly Arg Ser Val
        35                  40

<210> SEQ ID NO 120
<211> LENGTH: 43
<212> TYPE: PRT
<213> ORGANISM: Artificial Sequence
<220> FEATURE:
<223> OTHER INFORMATION: AT1 AND AT1brat GPCR TM1

<400> SEQUENCE: 120

Lys Ala Gly Arg His Asn Tyr Ile Phe Val Met Ile Pro Thr Leu Tyr
 1               5                   10                  15

Ser Ile Ile Phe Val Val Gly Ile Phe Gly Asn Ser Leu Val Val Ile
            20                  25                  30

Val Ile Tyr Phe Tyr Met Lys Leu Lys Thr Val
        35                  40

<210> SEQ ID NO 121
<211> LENGTH: 42
<212> TYPE: PRT
<213> ORGANISM: Artificial Sequence
<220> FEATURE:
<223> OTHER INFORMATION: AT2 GPCR TM1

<400> SEQUENCE: 121

Gln Lys Pro Ser Asp Lys His Leu Asp Ala Ile Pro Ile Leu Tyr Tyr
 1               5                   10                  15

Ile Ile Phe Val Ile Gly Phe Leu Val Asn Ile Val Val Val Thr Leu
            20                  25                  30

Phe Cys Cys Gln Lys Gly Pro Lys Lys Val
        35                  40

<210> SEQ ID NO 122
<211> LENGTH: 43
<212> TYPE: PRT
<213> ORGANISM: Artificial Sequence
<220> FEATURE:
<223> OTHER INFORMATION: BK1 GPCR TM1
```

-continued

```
<400> SEQUENCE: 122

Ala Pro Glu Ala Trp Asp Leu Leu His Arg Val Leu Pro Thr Phe Ile
1               5                   10                  15

Ile Ser Ile Cys Phe Phe Gly Leu Leu Gly Asn Leu Phe Val Leu Leu
            20                  25                  30

Val Phe Leu Leu Pro Arg Arg Gln Leu Asn Val
        35                  40

<210> SEQ ID NO 123
<211> LENGTH: 43
<212> TYPE: PRT
<213> ORGANISM: Artificial Sequence
<220> FEATURE:
<223> OTHER INFORMATION: BK2 GPCR TM1

<400> SEQUENCE: 123

Gln Val Glu Trp Leu Gly Trp Leu Asn Thr Ile Gln Pro Pro Phe Leu
1               5                   10                  15

Trp Val Leu Phe Val Leu Ala Thr Leu Glu Asn Ile Phe Val Leu Ser
            20                  25                  30

Val Phe Cys Leu His Lys Ser Ser Cys Thr Val
        35                  40

<210> SEQ ID NO 124
<211> LENGTH: 43
<212> TYPE: PRT
<213> ORGANISM: Artificial Sequence
<220> FEATURE:
<223> OTHER INFORMATION: P2Y7 GPCR TM1

<400> SEQUENCE: 124

Pro Ser Leu Gly Val Glu Phe Ile Ser Leu Leu Ala Ile Ile Leu Leu
1               5                   10                  15

Ser Val Ala Leu Ala Val Gly Leu Pro Gly Asn Ser Phe Val Val Trp
            20                  25                  30

Ser Ile Leu Lys Arg Met Gln Lys Arg Ser Val
        35                  40

<210> SEQ ID NO 125
<211> LENGTH: 43
<212> TYPE: PRT
<213> ORGANISM: Artificial Sequence
<220> FEATURE:
<223> OTHER INFORMATION: P2Y6 GPCR TM1

<400> SEQUENCE: 125

Cys Val Tyr Arg Glu Asp Phe Lys Arg Leu Leu Leu Pro Pro Val Tyr
1               5                   10                  15

Ser Val Val Leu Val Val Gly Leu Pro Leu Asn Val Cys Val Ile Ala
            20                  25                  30

Gln Ile Cys Ala Ser Arg Arg Thr Leu Thr Arg
        35                  40

<210> SEQ ID NO 126
<211> LENGTH: 43
<212> TYPE: PRT
<213> ORGANISM: Artificial Sequence
<220> FEATURE:
<223> OTHER INFORMATION: P2Y5 GPCR TM1
```

```
<400> SEQUENCE: 126

Cys Ser Thr Glu Asp Ser Phe Lys Tyr Thr Leu Tyr Gly Cys Val Phe
 1               5                  10                  15

Ser Met Val Phe Val Leu Gly Leu Ile Ala Asn Cys Val Ala Ile Tyr
                20                  25                  30

Ile Phe Thr Phe Thr Leu Lys Val Arg Asn Glu
            35                  40

<210> SEQ ID NO 127
<211> LENGTH: 43
<212> TYPE: PRT
<213> ORGANISM: Artificial Sequence
<220> FEATURE:
<223> OTHER INFORMATION: P2Y4 GPCR TM1

<400> SEQUENCE: 127

Cys Trp Phe Asp Glu Asp Phe Lys Phe Ile Leu Leu Pro Val Ser Tyr
 1               5                  10                  15

Ala Val Val Phe Val Leu Gly Leu Gly Leu Asn Ala Pro Thr Leu Trp
                20                  25                  30

Leu Phe Ile Phe Arg Leu Arg Pro Trp Asp Ala
            35                  40

<210> SEQ ID NO 128
<211> LENGTH: 43
<212> TYPE: PRT
<213> ORGANISM: Artificial Sequence
<220> FEATURE:
<223> OTHER INFORMATION: P2Y3chick GPCR TM1

<400> SEQUENCE: 128

Cys Thr Phe His Glu Glu Phe Lys Gln Val Leu Leu Pro Leu Val Tyr
 1               5                  10                  15

Ser Val Val Phe Leu Leu Gly Leu Pro Leu Asn Ala Val Val Ile Gly
                20                  25                  30

Gln Ile Trp Leu Ala Arg Lys Ala Leu Thr Arg
            35                  40

<210> SEQ ID NO 129
<211> LENGTH: 43
<212> TYPE: PRT
<213> ORGANISM: Artificial Sequence
<220> FEATURE:
<223> OTHER INFORMATION: P2Y2 GPCR TM1

<400> SEQUENCE: 129

Cys Arg Phe Asn Glu Asp Phe Lys Tyr Val Leu Leu Pro Val Ser Tyr
 1               5                  10                  15

Gly Val Val Cys Val Leu Gly Leu Cys Leu Asn Ala Val Gly Leu Tyr
                20                  25                  30

Ile Phe Leu Cys Arg Leu Lys Thr Trp Asn Ala
            35                  40

<210> SEQ ID NO 130
<211> LENGTH: 43
<212> TYPE: PRT
<213> ORGANISM: Artificial Sequence
<220> FEATURE:
<223> OTHER INFORMATION: P2Y1 GPCR TM1
```

```
<400> SEQUENCE: 130

Ala Leu Thr Lys Thr Gly Phe Gln Phe Tyr Tyr Leu Pro Ala Val Tyr
 1               5                  10                  15

Ile Leu Val Phe Ile Ile Gly Phe Leu Gly Asn Ser Val Ala Ile Trp
             20                  25                  30

Met Phe Val Phe His Met Lys Pro Trp Ser Gly
             35                  40

<210> SEQ ID NO 131
<211> LENGTH: 43
<212> TYPE: PRT
<213> ORGANISM: Artificial Sequence
<220> FEATURE:
<223> OTHER INFORMATION: THRprec GPCR TM1

<400> SEQUENCE: 131

Gly Tyr Leu Thr Ser Ser Trp Leu Thr Leu Phe Val Pro Ser Val Tyr
 1               5                  10                  15

Thr Gly Val Phe Val Val Ser Leu Pro Leu Asn Ile Met Ala Ile Val
             20                  25                  30

Val Phe Ile Leu Lys Met Lys Val Lys Lys Pro
             35                  40

<210> SEQ ID NO 132
<211> LENGTH: 42
<212> TYPE: PRT
<213> ORGANISM: Artificial Sequence
<220> FEATURE:
<223> OTHER INFORMATION: C5a GPCR TM1

<400> SEQUENCE: 132

Thr Ser Asn Thr Leu Arg Val Pro Asp Ile Leu Ala Leu Val Ile Phe
 1               5                  10                  15

Ala Val Val Phe Leu Val Gly Val Leu Gly Asn Ala Leu Val Val Trp
             20                  25                  30

Val Thr Ala Phe Glu Ala Lys Arg Thr Ile
             35                  40

<210> SEQ ID NO 133
<211> LENGTH: 43
<212> TYPE: PRT
<213> ORGANISM: Artificial Sequence
<220> FEATURE:
<223> OTHER INFORMATION: GP01mouse GPCR TM1

<400> SEQUENCE: 133

Ala Glu Ser Glu Pro Glu Leu Val Val Asn Pro Trp Asp Ile Val Leu
 1               5                  10                  15

Cys Ser Ser Gly Thr Leu Ile Cys Cys Glu Asn Ala Val Val Val Leu
             20                  25                  30

Ile Ile Phe His Ser Pro Ser Leu Arg Ala Pro
             35                  40

<210> SEQ ID NO 134
<211> LENGTH: 43
<212> TYPE: PRT
<213> ORGANISM: Artificial Sequence
<220> FEATURE:
<223> OTHER INFORMATION: R334rat GPCR TM1
```

-continued

```
<400> SEQUENCE: 134

Val Glu Ser Glu Pro Glu Leu Val Val Asn Pro Trp Asp Ile Val Leu
1               5                   10                  15

Cys Ser Ser Gly Thr Leu Ile Cys Cys Glu Asn Ala Val Val Val Leu
            20                  25                  30

Ile Ile Phe His Ser Pro Ser Leu Arg Ala Pro
        35                  40

<210> SEQ ID NO 135
<211> LENGTH: 43
<212> TYPE: PRT
<213> ORGANISM: Artificial Sequence
<220> FEATURE:
<223> OTHER INFORMATION: GP21mouse GPCR TM1

<400> SEQUENCE: 135

Gly Pro Ala Thr Leu Leu Pro Ser Pro Arg Ala Trp Asp Val Val Leu
1               5                   10                  15

Cys Ile Ser Gly Thr Leu Val Ser Cys Glu Asn Ala Leu Val Val Ala
            20                  25                  30

Ile Ile Val Gly Thr Pro Ala Phe Arg Ala Pro
        35                  40

<210> SEQ ID NO 136
<211> LENGTH: 43
<212> TYPE: PRT
<213> ORGANISM: Artificial Sequence
<220> FEATURE:
<223> OTHER INFORMATION: GCRCmouse GPCR TM1

<400> SEQUENCE: 136

Ala Glu Ser Gln Asn Pro Thr Val Lys Ala Leu Leu Ile Val Ala Tyr
1               5                   10                  15

Ser Phe Thr Ile Val Phe Ser Leu Phe Gly Asn Val Leu Val Cys His
            20                  25                  30

Val Ile Phe Lys Asn Gln Arg Met His Ser Ala
        35                  40

<210> SEQ ID NO 137
<211> LENGTH: 40
<212> TYPE: PRT
<213> ORGANISM: Artificial Sequence
<220> FEATURE:
<223> OTHER INFORMATION: TXKR GPCR TM1

<400> SEQUENCE: 137

Gln Pro Pro Trp Ala Val Ala Leu Trp Ser Leu Ala Tyr Gly Ala Val
1               5                   10                  15

Val Ala Val Ala Val Leu Gly Asn Leu Val Val Ile Trp Ile Val Leu
            20                  25                  30

Ala His Lys Arg Met Arg Thr Val
        35                  40

<210> SEQ ID NO 138
<211> LENGTH: 43
<212> TYPE: PRT
<213> ORGANISM: Artificial Sequence
<220> FEATURE:
<223> OTHER INFORMATION: G10Drat GPCR TM1
```

-continued

```
<400> SEQUENCE: 138

Met Glu Leu Asn Glu Asn Thr Lys Gln Val Val Leu Phe Val Phe Tyr
1               5                   10                  15

Leu Ala Ile Phe Val Val Gly Leu Val Glu Asn Val Leu Val Ile Cys
            20                  25                  30

Val Asn Cys Arg Arg Ser Gly Arg Val Gly Met
        35                  40

<210> SEQ ID NO 139
<211> LENGTH: 44
<212> TYPE: PRT
<213> ORGANISM: Artificial Sequence
<220> FEATURE:
<223> OTHER INFORMATION: RDC1 GPCR TM1

<400> SEQUENCE: 139

Asn Met Pro Asn Lys Ser Val Leu Leu Tyr Thr Leu Ser Phe Ile Tyr
1               5                   10                  15

Ile Phe Ile Phe Val Ile Gly Met Ile Ala Asn Ser Val Val Val Trp
            20                  25                  30

Val Asn Ile Gln Ala Lys Thr Thr Gly Tyr Asp Thr
        35                  40

<210> SEQ ID NO 140
<211> LENGTH: 42
<212> TYPE: PRT
<213> ORGANISM: Artificial Sequence
<220> FEATURE:
<223> OTHER INFORMATION: BLR1 GPCR TM1

<400> SEQUENCE: 140

Met Ala Ser Phe Lys Ala Val Phe Val Pro Val Ala Tyr Ser Leu Ile
1               5                   10                  15

Phe Leu Leu Gly Val Ile Gly Asn Val Leu Val Leu Val Ile Leu Glu
            20                  25                  30

Arg His Arg Gln Thr Arg Ser Ser Thr Glu
        35                  40

<210> SEQ ID NO 141
<211> LENGTH: 48
<212> TYPE: PRT
<213> ORGANISM: Artificial Sequence
<220> FEATURE:
<223> OTHER INFORMATION: CL5 AND LCR1 GPCR TM1

<400> SEQUENCE: 141

Arg Glu Glu Asn Ala Asn Phe Asn Lys Ile Phe Leu Pro Thr Ile Tyr
1               5                   10                  15

Ser Ile Ile Phe Leu Thr Gly Ile Val Gly Asn Gly Leu Val Ile Leu
            20                  25                  30

Val Met Gly Tyr Gln Lys Lys Leu Arg Ser Met Thr Asp Lys Tyr Arg
        35                  40                  45

<210> SEQ ID NO 142
<211> LENGTH: 47
<212> TYPE: PRT
<213> ORGANISM: Artificial Sequence
<220> FEATURE:
<223> OTHER INFORMATION: EBI1 GPCR TM1
```

```
<400> SEQUENCE: 142

Lys Lys Asp Val Arg Asn Phe Lys Ala Trp Phe Leu Pro Ile Met Tyr
 1               5                  10                  15

Ser Ile Ile Cys Phe Val Gly Leu Leu Gly Asn Gly Leu Val Val Leu
            20                  25                  30

Thr Tyr Ile Tyr Phe Lys Arg Leu Lys Thr Met Thr Asp Thr Tyr
        35                  40                  45

<210> SEQ ID NO 143
<211> LENGTH: 47
<212> TYPE: PRT
<213> ORGANISM: Artificial Sequence
<220> FEATURE:
<223> OTHER INFORMATION: RBS1rat GPCR TM1

<400> SEQUENCE: 143

Leu Gly Asp Ile Val Ala Phe Gly Thr Ile Phe Leu Ser Ile Phe Tyr
 1               5                  10                  15

Ser Leu Val Phe Thr Phe Gly Leu Val Gly Asn Leu Leu Val Val Leu
            20                  25                  30

Ala Leu Thr Asn Ser Arg Lys Ser Lys Ser Ile Thr Asp Ile Tyr
        35                  40                  45

<210> SEQ ID NO 144
<211> LENGTH: 47
<212> TYPE: PRT
<213> ORGANISM: Artificial Sequence
<220> FEATURE:
<223> OTHER INFORMATION: EBI2 GPCR TM1

<400> SEQUENCE: 144

Leu Tyr Ala His His Ser Thr Ala Arg Ile Val Met Pro Leu His Tyr
 1               5                  10                  15

Ser Leu Val Phe Ile Ile Gly Leu Val Gly Asn Leu Leu Ala Leu Val
            20                  25                  30

Val Ile Val Gln Asn Arg Lys Lys Ile Asn Ser Thr Thr Leu Tyr
        35                  40                  45

<210> SEQ ID NO 145
<211> LENGTH: 47
<212> TYPE: PRT
<213> ORGANISM: Artificial Sequence
<220> FEATURE:
<223> OTHER INFORMATION: GCRTchick GPCR TM1

<400> SEQUENCE: 145

Cys Ser Thr Glu Asp Ser Phe Lys Tyr Thr Leu Tyr Gly Cys Val Phe
 1               5                  10                  15

Ser Met Val Phe Val Leu Gly Leu Ile Ala Asn Cys Val Ala Ile Tyr
            20                  25                  30

Ile Phe Thr Phe Thr Leu Lys Val Arg Asn Glu Thr Thr Thr Tyr
        35                  40                  45

<210> SEQ ID NO 146
<211> LENGTH: 46
<212> TYPE: PRT
<213> ORGANISM: Artificial Sequence
<220> FEATURE:
<223> OTHER INFORMATION: APJ GPCR TM1
```

```
<400> SEQUENCE: 146

Glu Tyr Thr Asp Trp Lys Ser Ser Gly Ala Leu Ile Pro Ala Ile Tyr
 1               5                  10                  15

Met Leu Val Phe Leu Leu Gly Thr Thr Gly Asn Gly Leu Val Leu Trp
             20                  25                  30

Thr Val Phe Arg Ser Ser Arg Glu Lys Arg Arg Ser Ala Asp
         35                  40                  45

<210> SEQ ID NO 147
<211> LENGTH: 42
<212> TYPE: PRT
<213> ORGANISM: Artificial Sequence
<220> FEATURE:
<223> OTHER INFORMATION: RTArat GPCR TM1

<400> SEQUENCE: 147

Glu Gln Ile Ala Thr Leu Pro Pro Pro Ala Val Thr Asn Tyr Ile Phe
 1               5                  10                  15

Leu Leu Leu Cys Leu Cys Gly Leu Val Gly Asn Gly Leu Val Leu Trp
             20                  25                  30

Phe Phe Gly Phe Ser Ile Lys Arg Thr Pro
         35                  40

<210> SEQ ID NO 148
<211> LENGTH: 43
<212> TYPE: PRT
<213> ORGANISM: Artificial Sequence
<220> FEATURE:
<223> OTHER INFORMATION: UHRrat GPCR TM1

<400> SEQUENCE: 148

Ser Leu Gln Leu Val His Gln Leu Lys Gly Leu Ile Val Met Leu Tyr
 1               5                  10                  15

Ser Ile Val Val Val Gly Leu Val Gly Asn Cys Leu Leu Val Leu
             20                  25                  30

Val Ile Ala Arg Val Arg Arg Leu His Asn Val
         35                  40

<210> SEQ ID NO 149
<211> LENGTH: 42
<212> TYPE: PRT
<213> ORGANISM: Artificial Sequence
<220> FEATURE:
<223> OTHER INFORMATION: FMRL1N GPCR TM1

<400> SEQUENCE: 149

Glu Pro Ala Gly His Thr Val Leu Trp Ile Phe Ser Leu Leu Val His
 1               5                  10                  15

Gly Val Thr Phe Val Phe Gly Val Leu Gly Asn Gly Leu Val Ile Trp
             20                  25                  30

Val Ala Gly Phe Arg Met Thr Arg Thr Val
         35                  40

<210> SEQ ID NO 150
<211> LENGTH: 42
<212> TYPE: PRT
<213> ORGANISM: Artificial Sequence
<220> FEATURE:
<223> OTHER INFORMATION: FMRL2 GPCR TM1
```

-continued

```
<400> SEQUENCE: 150

Glu Ser Ala Gly Tyr Thr Val Leu Arg Ile Leu Pro Leu Val Val Leu
1               5                   10                  15

Gly Val Thr Phe Val Leu Gly Val Leu Gly Asn Gly Leu Val Ile Trp
            20                  25                  30

Val Ala Gly Phe Arg Met Thr Arg Thr Val
        35                  40

<210> SEQ ID NO 151
<211> LENGTH: 42
<212> TYPE: PRT
<213> ORGANISM: Artificial Sequence
<220> FEATURE:
<223> OTHER INFORMATION: fMLP GPCR TM1

<400> SEQUENCE: 151

Val Ser Ala Gly Tyr Leu Phe Leu Asp Ile Ile Thr Tyr Leu Val Phe
1               5                   10                  15

Ala Val Thr Phe Val Leu Gly Val Leu Gly Asn Gly Leu Val Ile Trp
            20                  25                  30

Val Ala Gly Phe Arg Met Thr His Thr Val
        35                  40

<210> SEQ ID NO 152
<211> LENGTH: 43
<212> TYPE: PRT
<213> ORGANISM: Artificial Sequence
<220> FEATURE:
<223> OTHER INFORMATION: OLF1catfish GPCR TM1

<400> SEQUENCE: 152

Asn Gly Phe Tyr Asn Ile Pro His Thr Lys Tyr Tyr Tyr Ala Phe Leu
1               5                   10                  15

Cys Ile Ala Tyr Ala Val Thr Val Leu Gly Asn Ser Phe Ile Met Cys
            20                  25                  30

Thr Ile Tyr Leu Ala Arg Ser Leu His Thr Ala
        35                  40

<210> SEQ ID NO 153
<211> LENGTH: 43
<212> TYPE: PRT
<213> ORGANISM: Artificial Sequence
<220> FEATURE:
<223> OTHER INFORMATION: OLF3catfish GPCR TM1

<400> SEQUENCE: 153

Thr Gly Leu Tyr Asn Ile Pro His Ala Lys Tyr Tyr Tyr Leu Phe Leu
1               5                   10                  15

Cys Phe Val Tyr Thr Val Thr Phe Leu Gly Asn Ser Phe Ile Met Gly
            20                  25                  30

Thr Ile Tyr Leu Ala Arg Ser Leu His Thr Ala
        35                  40

<210> SEQ ID NO 154
<211> LENGTH: 43
<212> TYPE: PRT
<213> ORGANISM: Artificial Sequence
<220> FEATURE:
<223> OTHER INFORMATION: OLF8catfish GPCR TM1
```

-continued

```
<400> SEQUENCE: 154

Gly Phe His Asp Leu Gly Glu Trp Gly Pro Ile Leu Ser Ile Pro Tyr
1               5                   10                  15

Leu Leu Met Phe Leu Leu Ser Ser Thr Ser Asn Leu Thr Leu Ile Tyr
            20                  25                  30

Leu Ile Ile Ser Gln Arg Ala Leu His Ser Pro
        35                  40

<210> SEQ ID NO 155
<211> LENGTH: 43
<212> TYPE: PRT
<213> ORGANISM: Artificial Sequence
<220> FEATURE:
<223> OTHER INFORMATION: OLF32Acatfish GPCR TM1

<400> SEQUENCE: 155

Ser Gly Phe Ser Gly Ile Pro Phe Ser Gln Tyr Tyr Phe Ala Phe Leu
1               5                   10                  15

Ile Phe Ile Tyr Ile Ile Ser Leu Cys Gly Asn Ser Ile Val Leu Phe
            20                  25                  30

Met Ile Leu Val Asp Arg Thr Leu His Ile Pro
        35                  40

<210> SEQ ID NO 156
<211> LENGTH: 43
<212> TYPE: PRT
<213> ORGANISM: Artificial Sequence
<220> FEATURE:
<223> OTHER INFORMATION: OLF32Bcatfish, OLF32Ccatfish AND OLF32Dcatfish
      GPCR TM1

<400> SEQUENCE: 156

Ser Gly Phe Ser Gly Ile Pro Phe Ser Gln Tyr Tyr Phe Val Phe Leu
1               5                   10                  15

Ile Phe Ile Tyr Ile Ile Ser Leu Cys Gly Asn Ser Ile Val Leu Phe
            20                  25                  30

Met Ile Leu Val Asp Arg Thr Leu His Ile Pro
        35                  40

<210> SEQ ID NO 157
<211> LENGTH: 43
<212> TYPE: PRT
<213> ORGANISM: Artificial Sequence
<220> FEATURE:
<223> OTHER INFORMATION: OLF47catfish GPCR TM1

<400> SEQUENCE: 157

Ile Ala Tyr Asn Ser Leu Gly Asn Lys Asn Tyr Leu Ile Leu Ala Leu
1               5                   10                  15

Gly Ile Ile Tyr Leu Ile Thr Leu Leu Cys Asn Phe Thr Leu Leu Ala
            20                  25                  30

Ile Ile Leu Met Asn Ser Ser Leu Gln Asn Pro
        35                  40

<210> SEQ ID NO 158
<211> LENGTH: 43
<212> TYPE: PRT
<213> ORGANISM: Artificial Sequence
<220> FEATURE:
<223> OTHER INFORMATION: OLF202catfish GPCR TM1
```

<400> SEQUENCE: 158

Phe Pro Gly Leu Pro Pro Asn Tyr Tyr Gly Leu Val Ser Val Val Met
1               5                   10                  15

Phe Phe Val Tyr Val Cys Thr Leu Ile Gly Asn Cys Thr Phe Phe Thr
            20                  25                  30

Leu Phe Leu Arg Glu Lys Ser Leu Gln Lys Pro
        35                  40

<210> SEQ ID NO 159
<211> LENGTH: 42
<212> TYPE: PRT
<213> ORGANISM: Artificial Sequence
<220> FEATURE:
<223> OTHER INFORMATION: OLFCOR1chicken GPCR TM1

<400> SEQUENCE: 159

Leu Thr Asp Asn Pro Gly Leu Gln Met Pro Leu Phe Met Val Phe Leu
1               5                   10                  15

Ala Ile Tyr Thr Ile Thr Leu Leu Thr Asn Leu Gly Leu Ile Ala Leu
            20                  25                  30

Ile Ser Val Asp Leu His Leu Gln Thr Pro
        35                  40

<210> SEQ ID NO 160
<211> LENGTH: 42
<212> TYPE: PRT
<213> ORGANISM: Artificial Sequence
<220> FEATURE:
<223> OTHER INFORMATION: OLFCOR2chicken GPCR TM1

<400> SEQUENCE: 160

Leu Thr Asp Asn Pro Arg Leu Gln Met Pro Leu Phe Met Val Phe Leu
1               5                   10                  15

Val Ile Tyr Thr Thr Thr Leu Leu Thr Asn Leu Gly Leu Ile Ala Leu
            20                  25                  30

Ile Gly Met Asp Leu His Leu Gln Thr Pro
        35                  40

<210> SEQ ID NO 161
<211> LENGTH: 42
<212> TYPE: PRT
<213> ORGANISM: Artificial Sequence
<220> FEATURE:
<223> OTHER INFORMATION: OLFCOR3chicken AND OLFCOR4chicken GPCR TM1

<400> SEQUENCE: 161

Leu Thr Asp Asn Pro Gly Leu Gln Met Pro Leu Phe Met Val Phe Leu
1               5                   10                  15

Ala Ile Tyr Thr Ile Thr Leu Leu Thr Asn Leu Gly Leu Ile Arg Leu
            20                  25                  30

Ile Ser Val Asp Leu His Leu Gln Thr Pro
        35                  40

<210> SEQ ID NO 162
<211> LENGTH: 42
<212> TYPE: PRT
<213> ORGANISM: Artificial Sequence
<220> FEATURE:
<223> OTHER INFORMATION: OLFCOR5chicken GPCR TM1

-continued

```
<400> SEQUENCE: 162

Leu Thr Asp Asn Pro Arg Leu Gln Met Pro Leu Phe Met Val Phe Leu
1               5                   10                  15

Ala Ile Tyr Thr Ile Thr Leu Leu Ala Asn Leu Gly Leu Ile Ala Leu
            20                  25                  30

Ile Ser Val Asp Phe His Leu Gln Thr Pro
        35                  40

<210> SEQ ID NO 163
<211> LENGTH: 42
<212> TYPE: PRT
<213> ORGANISM: Artificial Sequence
<220> FEATURE:
<223> OTHER INFORMATION: OLFCOR6chicken GPCR TM1

<400> SEQUENCE: 163

Leu Thr Asp Asn Pro Gly Leu Gln Met Pro Leu Phe Met Val Phe Leu
1               5                   10                  15

Ala Ile Tyr Thr Ile Thr Leu Leu Thr Asn Leu Gly Leu Ile Ala Leu
            20                  25                  30

Ile Arg Ile Asp Leu Gln Leu Gln Thr Pro
        35                  40

<210> SEQ ID NO 164
<211> LENGTH: 42
<212> TYPE: PRT
<213> ORGANISM: Artificial Sequence
<220> FEATURE:
<223> OTHER INFORMATION: OLFdog GPCR TM1

<400> SEQUENCE: 164

Leu Pro Ile Asp Pro Asp Gln Arg Asp Leu Phe Tyr Ala Leu Phe Leu
1               5                   10                  15

Ala Met Tyr Val Thr Thr Ile Leu Gly Asn Leu Leu Ile Ile Val Leu
            20                  25                  30

Ile Gln Leu Asp Ser His Leu His Thr Pro
        35                  40

<210> SEQ ID NO 165
<211> LENGTH: 42
<212> TYPE: PRT
<213> ORGANISM: Artificial Sequence
<220> FEATURE:
<223> OTHER INFORMATION: OLF07E GPCR TM1

<400> SEQUENCE: 165

Met Ser Glu Ser Pro Glu Gln Gln Ile Leu Phe Trp Met Phe Leu
1               5                   10                  15

Ser Met Tyr Leu Val Thr Val Val Gly Asn Val Leu Ile Ile Leu Ala
            20                  25                  30

Ile Ser Ser Asp Ser Arg Leu His Thr Pro
        35                  40

<210> SEQ ID NO 166
<211> LENGTH: 42
<212> TYPE: PRT
<213> ORGANISM: Artificial Sequence
<220> FEATURE:
<223> OTHER INFORMATION: OLF07I GPCR TM1
```

```
<400> SEQUENCE: 166

Leu Pro Ile Gln Pro Glu Gln Gln Asn Leu Cys Tyr Ala Leu Phe Leu
 1               5                  10                  15

Ala Met Tyr Leu Thr Thr Leu Leu Gly Asn Leu Leu Ile Ile Val Leu
             20                  25                  30

Ile Arg Leu Asp Ser His Leu His Thr Pro
         35                  40

<210> SEQ ID NO 167
<211> LENGTH: 42
<212> TYPE: PRT
<213> ORGANISM: Artificial Sequence
<220> FEATURE:
<223> OTHER INFORMATION: OLF07J GPCR TM1

<400> SEQUENCE: 167

Phe Ser Ser Phe His Glu Gln Gln Ile Thr Leu Phe Gly Val Phe Leu
 1               5                  10                  15

Ala Leu Tyr Ile Leu Thr Leu Ala Gly Asn Ile Ile Ile Val Thr Ile
             20                  25                  30

Ile Arg Ile Asp Leu His Leu His Thr Pro
         35                  40

<210> SEQ ID NO 168
<211> LENGTH: 42
<212> TYPE: PRT
<213> ORGANISM: Artificial Sequence
<220> FEATURE:
<223> OTHER INFORMATION: OLFOR3mouse GPCR TM1

<400> SEQUENCE: 168

Val Ser Asp His Pro His Leu Glu Ile Ile Phe Phe Ala Val Ile Leu
 1               5                  10                  15

Ala Ser Tyr Leu Leu Thr Leu Val Gly Asn Leu Thr Ile Ile Leu Leu
             20                  25                  30

Ser Arg Leu Asp Ala Arg Leu His Thr Pro
         35                  40

<210> SEQ ID NO 169
<211> LENGTH: 42
<212> TYPE: PRT
<213> ORGANISM: Artificial Sequence
<220> FEATURE:
<223> OTHER INFORMATION: OLFrat GPCR TM1

<400> SEQUENCE: 169

Leu Thr Lys Gln Pro Glu Leu Leu Pro Leu Phe Phe Leu Phe Leu
 1               5                  10                  15

Val Ile Tyr Val Leu Thr Val Val Gly Asn Leu Gly Met Ile Leu Leu
             20                  25                  30

Ile Ile Val Ser Pro Leu Leu His Thr Pro
         35                  40

<210> SEQ ID NO 170
<211> LENGTH: 42
<212> TYPE: PRT
<213> ORGANISM: Artificial Sequence
<220> FEATURE:
<223> OTHER INFORMATION: OLFF3rat GPCR TM1
```

-continued

<400> SEQUENCE: 170

Phe Val Glu Asn Lys Asp Leu Gln Pro Leu Ile Tyr Gly Leu Phe Leu
1               5                   10                  15

Ser Met Tyr Leu Val Thr Val Ile Gly Asn Ile Ser Ile Ile Val Ala
            20                  25                  30

Ile Ile Ser Asp Pro Cys Leu His Thr Pro
        35                  40

<210> SEQ ID NO 171
<211> LENGTH: 42
<212> TYPE: PRT
<213> ORGANISM: Artificial Sequence
<220> FEATURE:
<223> OTHER INFORMATION: OLFF5rat GPCR TM1

<400> SEQUENCE: 171

Leu Ser Arg Gln Pro Gln Gln Gln Leu Leu Phe Leu Leu Phe Leu
1               5                   10                  15

Ile Met Tyr Leu Ala Thr Val Leu Gly Asn Leu Leu Ile Ile Leu Ala
            20                  25                  30

Ile Gly Thr Asp Ser Arg Leu His Thr Pro
        35                  40

<210> SEQ ID NO 172
<211> LENGTH: 42
<212> TYPE: PRT
<213> ORGANISM: Artificial Sequence
<220> FEATURE:
<223> OTHER INFORMATION: OLFF6rat GPCR TM1

<400> SEQUENCE: 172

Phe Pro Gly Pro Arg Ser Met Arg Ile Gly Leu Phe Leu Phe Leu
1               5                   10                  15

Val Met Tyr Leu Leu Thr Val Val Gly Asn Leu Ala Ile Ile Ser Leu
            20                  25                  30

Val Gly Ala His Arg Cys Leu Gln Thr Pro
        35                  40

<210> SEQ ID NO 173
<211> LENGTH: 42
<212> TYPE: PRT
<213> ORGANISM: Artificial Sequence
<220> FEATURE:
<223> OTHER INFORMATION: OLFF12rat GPCR TM1

<400> SEQUENCE: 173

Phe Thr Glu Asn Pro Gln Leu His Phe Leu Ile Phe Ala Leu Phe Leu
1               5                   10                  15

Ser Met Tyr Leu Val Thr Val Leu Gly Asn Leu Leu Ile Ile Met Ala
            20                  25                  30

Ile Ile Thr Gln Ser His Leu His Thr Pro
        35                  40

<210> SEQ ID NO 174
<211> LENGTH: 42
<212> TYPE: PRT
<213> ORGANISM: Artificial Sequence
<220> FEATURE:
<223> OTHER INFORMATION: OLFI3rat GPCR TM1

```
<400> SEQUENCE: 174

Leu Pro Ile Pro Glu His Gln His Leu Phe Tyr Ala Leu Phe Leu
  1               5                  10                  15

Val Met Tyr Leu Thr Thr Ile Leu Gly Asn Leu Leu Ile Ile Val Leu
             20                  25                  30

Val Gln Leu Asp Ser Gln Leu His Thr Pro
         35                  40

<210> SEQ ID NO 175
<211> LENGTH: 42
<212> TYPE: PRT
<213> ORGANISM: Artificial Sequence
<220> FEATURE:
<223> OTHER INFORMATION: OLFI7rat GPCR TM1
<221> NAME/KEY: MOD_RES
<222> LOCATION: (18)...(18)
<223> OTHER INFORMATION: Xaa = unknown amino acid

<400> SEQUENCE: 175

Phe Pro Ala Pro Ala Pro Leu Arg Val Leu Phe Phe Leu Ser Leu
  1               5                  10                  15

Leu Xaa Tyr Val Leu Val Leu Thr Glu Asn Met Leu Ile Ile Ile Ala
             20                  25                  30

Ile Arg Asn His Pro Thr Leu His Lys Pro
         35                  40

<210> SEQ ID NO 176
<211> LENGTH: 42
<212> TYPE: PRT
<213> ORGANISM: Artificial Sequence
<220> FEATURE:
<223> OTHER INFORMATION: OLFI8rat GPCR TM1

<400> SEQUENCE: 176

Leu Pro Ile Pro Pro Glu His Gln Gln Leu Phe Phe Ala Leu Phe Leu
  1               5                  10                  15

Ile Met Tyr Leu Thr Thr Phe Leu Gly Asn Leu Leu Ile Val Val Leu
             20                  25                  30

Val Gln Leu Asp Ser His Leu His Thr Pro
         35                  40

<210> SEQ ID NO 177
<211> LENGTH: 42
<212> TYPE: PRT
<213> ORGANISM: Artificial Sequence
<220> FEATURE:
<223> OTHER INFORMATION: OLFI9rat GPCR TM1

<400> SEQUENCE: 177

Leu Pro Phe Pro Pro Glu Tyr Gln His Leu Phe Tyr Ala Leu Phe Leu
  1               5                  10                  15

Ala Met Tyr Leu Thr Thr Leu Leu Gly Asn Leu Ile Ile Ile Ile Leu
             20                  25                  30

Ile Leu Leu Asp Ser His Leu His Thr Pro
         35                  40

<210> SEQ ID NO 178
<211> LENGTH: 42
<212> TYPE: PRT
<213> ORGANISM: Artificial Sequence
<220> FEATURE:
<223> OTHER INFORMATION: OLFI14rat GPCR TM1
```

-continued

```
<400> SEQUENCE: 178

Leu Pro Ile Pro Ser Glu Tyr His Leu Leu Phe Tyr Ala Leu Phe Leu
  1               5                  10                  15

Ala Met Tyr Leu Thr Ile Ile Leu Gly Asn Leu Leu Ile Ile Val Leu
             20                  25                  30

Val Arg Leu Asp Ser His Leu His Met Pro
         35                  40

<210> SEQ ID NO 179
<211> LENGTH: 42
<212> TYPE: PRT
<213> ORGANISM: Artificial Sequence
<220> FEATURE:
<223> OTHER INFORMATION: OLFI15rat GPCR TM1

<400> SEQUENCE: 179

Leu Pro Ile Pro Ser Glu His Gln His Val Phe Tyr Ala Leu Phe Leu
  1               5                  10                  15

Ser Met Tyr Leu Thr Thr Val Leu Gly Asn Leu Ile Ile Ile Ile Leu
             20                  25                  30

Ile His Leu Asp Ser His Leu His Thr Pro
         35                  40

<210> SEQ ID NO 180
<211> LENGTH: 42
<212> TYPE: PRT
<213> ORGANISM: Artificial Sequence
<220> FEATURE:
<223> OTHER INFORMATION: OLFOR17_40 GPCR TM1

<400> SEQUENCE: 180

Leu Leu Glu Ala Pro Gly Leu Gln Pro Val Val Phe Val Leu Phe Leu
  1               5                  10                  15

Phe Ala Tyr Leu Val Thr Val Arg Gly Asn Leu Ser Ile Leu Ala Ala
             20                  25                  30

Val Leu Val Glu Pro Lys Leu His Thr Pro
         35                  40

<210> SEQ ID NO 181
<211> LENGTH: 39
<212> TYPE: PRT
<213> ORGANISM: Artificial Sequence
<220> FEATURE:
<223> OTHER INFORMATION: GUST27rat GPCR TM1

<400> SEQUENCE: 181

Met Ile Leu Asn Cys Asn Pro Phe Ser Gly Leu Phe Leu Ser Met Tyr
  1               5                  10                  15

Leu Val Thr Val Leu Gly Asn Leu Leu Ile Ile Leu Ala Val Ser Ser
             20                  25                  30

Asn Ser His Leu His Asn Leu
         35

<210> SEQ ID NO 182
<211> LENGTH: 43
<212> TYPE: PRT
<213> ORGANISM: Artificial Sequence
<220> FEATURE:
<223> OTHER INFORMATION: RPE GPCR TM1
```

-continued

```
<400> SEQUENCE: 182

Pro Thr Gly Phe Gly Glu Leu Glu Val Leu Ala Val Gly Met Val Leu
 1               5                  10                  15

Leu Val Glu Ala Leu Ser Gly Leu Ser Leu Asn Thr Leu Thr Ile Phe
            20                  25                  30

Ser Phe Cys Lys Thr Pro Glu Leu Arg Thr Pro
         35                  40

<210> SEQ ID NO 183
<211> LENGTH: 43
<212> TYPE: PRT
<213> ORGANISM: Artificial Sequence
<220> FEATURE:
<223> OTHER INFORMATION: HHRF1 GPCR TM1

<400> SEQUENCE: 183

Phe Thr Asp Val Leu Asn Gln Ser Lys Pro Val Thr Leu Phe Leu Tyr
 1               5                  10                  15

Gly Val Val Phe Leu Phe Gly Ser Ile Gly Asn Phe Leu Val Ile Phe
            20                  25                  30

Thr Ile Thr Trp Arg Arg Arg Ile Gln Cys Ser
         35                  40

<210> SEQ ID NO 184
<211> LENGTH: 44
<212> TYPE: PRT
<213> ORGANISM: Artificial Sequence
<220> FEATURE:
<223> OTHER INFORMATION: HHRF2 GPCR TM1

<400> SEQUENCE: 184

Asn Ser Thr Glu Ile Tyr Gln Leu Phe Glu Tyr Thr Arg Leu Gly Val
 1               5                  10                  15

Trp Leu Met Cys Ile Val Gly Thr Phe Leu Asn Val Leu Val Ile Thr
            20                  25                  30

Thr Ile Leu Tyr Tyr Arg Arg Lys Lys Lys Ser Pro
         35                  40

<210> SEQ ID NO 185
<211> LENGTH: 45
<212> TYPE: PRT
<213> ORGANISM: Artificial Sequence
<220> FEATURE:
<223> OTHER INFORMATION: HHRF3 GPCR TM1

<400> SEQUENCE: 185

Met Thr Gly Pro Leu Phe Ala Ile Arg Thr Thr Glu Ala Val Leu Asn
 1               5                  10                  15

Thr Phe Ile Ile Phe Val Gly Gly Pro Leu Asn Ala Ile Val Leu Ile
            20                  25                  30

Thr Gln Leu Leu Thr Asn Arg Val Leu Gly Tyr Ser Thr
         35                  40                  45

<210> SEQ ID NO 186
<211> LENGTH: 41
<212> TYPE: PRT
<213> ORGANISM: Artificial Sequence
<220> FEATURE:
<223> OTHER INFORMATION: MCP-1A AND MCP-1B GPCR TM1
```

-continued

```
<400> SEQUENCE: 186

Asp Val Lys Gln Ile Gly Ala Gln Leu Leu Pro Pro Leu Tyr Ser Leu
1               5                   10                  15

Val Phe Ile Phe Gly Phe Val Gly Asn Met Leu Val Val Leu Ile Leu
            20                  25                  30

Ile Asn Cys Lys Lys Leu Lys Cys Leu
        35                  40

<210> SEQ ID NO 187
<211> LENGTH: 41
<212> TYPE: PRT
<213> ORGANISM: Artificial Sequence
<220> FEATURE:
<223> OTHER INFORMATION: PPR1bovine GPCR TM1

<400> SEQUENCE: 187

Glu Val Arg Lys Phe Ala Lys Val Phe Leu Pro Ala Phe Phe Thr Ile
1               5                   10                  15

Ala Phe Ile Ile Gly Leu Ala Gly Asn Ser Thr Val Val Ala Ile Tyr
            20                  25                  30

Ala Tyr Tyr Lys Lys Arg Arg Thr Lys
        35                  40

<210> SEQ ID NO 188
<211> LENGTH: 50
<212> TYPE: PRT
<213> ORGANISM: Artificial Sequence
<220> FEATURE:
<223> OTHER INFORMATION: GPCRAelegans GPCR TM2

<400> SEQUENCE: 188

Thr Arg Phe Leu Met Cys Asn Leu Ala Phe Ala Asp Phe Ile Leu Gly
1               5                   10                  15

Leu Tyr Ile Phe Ile Leu Thr Ser Val Ser Ala Val Thr Arg Gly Asp
            20                  25                  30

Tyr His Asn Tyr Val Gln Gln Trp Gln Asn Gly Ala Gly Cys Lys Ile
        35                  40                  45

Leu Gly
    50

<210> SEQ ID NO 189
<211> LENGTH: 42
<212> TYPE: PRT
<213> ORGANISM: Artificial Sequence
<220> FEATURE:
<223> OTHER INFORMATION: GRH GPCR TM2

<400> SEQUENCE: 189

Lys Leu Leu Leu Lys His Leu Thr Leu Ala Asn Leu Leu Glu Thr Leu
1               5                   10                  15

Ile Val Met Pro Leu Asp Gly Met Trp Asn Ile Thr Val Gln Trp Tyr
            20                  25                  30

Ala Gly Glu Leu Leu Cys Lys Val Leu Ser
        35                  40

<210> SEQ ID NO 190
<211> LENGTH: 43
<212> TYPE: PRT
<213> ORGANISM: Artificial Sequence
<220> FEATURE:
<223> OTHER INFORMATION: TRH GPCR TM2
```

-continued

```
<400> SEQUENCE: 190

Thr Asn Cys Tyr Leu Val Ser Leu Ala Val Ala Asp Leu Met Val Leu
1               5                   10                  15

Val Ala Ala Gly Leu Pro Asn Ile Thr Asp Ser Ile Tyr Gly Ser Trp
            20                  25                  30

Val Tyr Gly Tyr Val Gly Cys Leu Cys Ile Thr
        35                  40

<210> SEQ ID NO 191
<211> LENGTH: 50
<212> TYPE: PRT
<213> ORGANISM: Artificial Sequence
<220> FEATURE:
<223> OTHER INFORMATION: FSHprec GPCR TM2

<400> SEQUENCE: 191

Pro Arg Phe Leu Met Cys Asn Leu Ala Phe Ala Asp Leu Cys Ile Gly
1               5                   10                  15

Ile Tyr Leu Leu Leu Ile Ala Ser Val Asp Ile His Thr Lys Ser Gln
            20                  25                  30

Tyr His Asn Tyr Ala Ile Asp Trp Gln Thr Gly Ala Gly Cys Asp Ala
        35                  40                  45

Ala Gly
    50

<210> SEQ ID NO 192
<211> LENGTH: 50
<212> TYPE: PRT
<213> ORGANISM: Artificial Sequence
<220> FEATURE:
<223> OTHER INFORMATION: TSHprec GPCR TM2

<400> SEQUENCE: 192

Pro Arg Phe Leu Met Cys Asn Leu Ala Phe Ala Asp Phe Cys Met Gly
1               5                   10                  15

Met Tyr Leu Leu Leu Ile Ala Ser Val Asp Leu Tyr Thr His Ser Glu
            20                  25                  30

Tyr Tyr Asn His Ala Ile Asp Trp Gln Thr Gly Pro Gly Cys Asn Thr
        35                  40                  45

Ala Gly
    50

<210> SEQ ID NO 193
<211> LENGTH: 50
<212> TYPE: PRT
<213> ORGANISM: Artificial Sequence
<220> FEATURE:
<223> OTHER INFORMATION: LH_CGprec GPCR TM2

<400> SEQUENCE: 193

Pro Arg Phe Leu Met Cys Asn Leu Ser Phe Ala Asp Phe Cys Met Gly
1               5                   10                  15

Leu Tyr Leu Leu Leu Ile Ala Ser Val Asp Ser Gln Thr Lys Gly Gln
            20                  25                  30

Tyr Tyr Asn His Ala Ile Asp Trp Gln Thr Gly Ser Gly Cys Ser Thr
        35                  40                  45

Ala Gly
    50
```

```
<210> SEQ ID NO 194
<211> LENGTH: 42
<212> TYPE: PRT
<213> ORGANISM: Artificial Sequence
<220> FEATURE:
<223> OTHER INFORMATION: PGE_EP1 GPCR TM2

<400> SEQUENCE: 194

Phe Leu Leu Phe Val Ala Ser Leu Leu Ala Thr Asp Leu Ala Gly His
  1               5                  10                  15

Val Ile Pro Gly Ala Leu Val Leu Arg Leu Tyr Thr Ala Gly Arg Ala
             20                  25                  30

Pro Ala Gly Gly Ala Cys His Phe Leu Gly
         35                  40

<210> SEQ ID NO 195
<211> LENGTH: 43
<212> TYPE: PRT
<213> ORGANISM: Artificial Sequence
<220> FEATURE:
<223> OTHER INFORMATION: PGE_EP2 GPCR TM2

<400> SEQUENCE: 195

Phe Tyr Thr Leu Val Cys Gly Leu Ala Val Thr Asp Leu Leu Gly Thr
  1               5                  10                  15

Leu Leu Val Ser Pro Val Thr Ile Ala Thr Tyr Met Lys Gly Gln Trp
             20                  25                  30

Pro Gly Gly Gln Pro Leu Cys Glu Tyr Ser Thr
         35                  40

<210> SEQ ID NO 196
<211> LENGTH: 47
<212> TYPE: PRT
<213> ORGANISM: Artificial Sequence
<220> FEATURE:
<223> OTHER INFORMATION: PGE_EP3 GPCR TM2

<400> SEQUENCE: 196

Phe His Val Leu Val Thr Glu Leu Val Phe Thr Asp Leu Leu Gly Thr
  1               5                  10                  15

Cys Leu Ile Ser Pro Val Val Leu Ala Ser Tyr Ala Arg Asn Gln Thr
             20                  25                  30

Leu Val Ala Leu Ala Pro Glu Ser Arg Ala Cys Thr Tyr Phe Ala
         35                  40                  45

<210> SEQ ID NO 197
<211> LENGTH: 47
<212> TYPE: PRT
<213> ORGANISM: Artificial Sequence
<220> FEATURE:
<223> OTHER INFORMATION: PGF GPCR TM2

<400> SEQUENCE: 197

Phe Leu Leu Leu Ala Ser Gly Leu Val Ile Thr Asp Phe Phe Gly His
  1               5                  10                  15

Leu Ile Asn Gly Ala Ile Ala Val Phe Val Tyr Ala Ser Asp Lys Glu
             20                  25                  30

Trp Ile Arg Phe Asp Gln Ser Asn Val Leu Cys Ser Ile Phe Gly
         35                  40                  45
```

<210> SEQ ID NO 198
<211> LENGTH: 48
<212> TYPE: PRT
<213> ORGANISM: Artificial Sequence
<220> FEATURE:
<223> OTHER INFORMATION: PGI GPCR TM2

<400> SEQUENCE: 198

```
Phe Ala Val Leu Val Thr Gly Leu Ala Ala Thr Asp Leu Leu Gly Thr
 1               5                  10                  15
Ser Phe Leu Ser Pro Ala Val Phe Val Ala Tyr Ala Arg Asn Ser Ser
            20                  25                  30
Leu Leu Gly Leu Ala Arg Gly Gly Pro Ala Leu Cys Asp Ala Phe Ala
        35                  40                  45
```

<210> SEQ ID NO 199
<211> LENGTH: 47
<212> TYPE: PRT
<213> ORGANISM: Artificial Sequence
<220> FEATURE:
<223> OTHER INFORMATION: TXA2 GPCR TM2

<400> SEQUENCE: 199

```
Phe Leu Thr Phe Leu Cys Gly Leu Val Leu Thr Asp Phe Leu Gly Leu
 1               5                  10                  15
Leu Val Thr Gly Thr Ile Val Val Ser Gln His Ala Ala Leu Phe Glu
            20                  25                  30
Trp His Ala Val Asp Pro Gly Cys Arg Leu Cys Arg Phe Met Gly
        35                  40                  45
```

<210> SEQ ID NO 200
<211> LENGTH: 41
<212> TYPE: PRT
<213> ORGANISM: Artificial Sequence
<220> FEATURE:
<223> OTHER INFORMATION: PAF GPCR TM2

<400> SEQUENCE: 200

```
Ile Phe Met Val Asn Leu Thr Met Ala Asp Met Leu Phe Leu Ile Thr
 1               5                  10                  15
Leu Pro Leu Trp Ile Val Tyr Tyr Gln Asn Gln Gly Asn Trp Ile Leu
            20                  25                  30
Pro Lys Phe Leu Cys Asn Val Ala Gly
        35                  40
```

<210> SEQ ID NO 201
<211> LENGTH: 43
<212> TYPE: PRT
<213> ORGANISM: Artificial Sequence
<220> FEATURE:
<223> OTHER INFORMATION: M2 GPCR TM2

<400> SEQUENCE: 201

```
Asn Asn Tyr Phe Leu Phe Ser Leu Ala Cys Ala Asp Leu Ile Ile Gly
 1               5                  10                  15
Val Phe Ser Met Asn Leu Tyr Thr Leu Tyr Thr Val Ile Gly Tyr Trp
            20                  25                  30
Pro Leu Gly Pro Val Val Cys Asp Leu Trp Leu
        35                  40
```

```
<210> SEQ ID NO 202
<211> LENGTH: 43
<212> TYPE: PRT
<213> ORGANISM: Artificial Sequence
<220> FEATURE:
<223> OTHER INFORMATION: M4 GPCR TM2

<400> SEQUENCE: 202

Asn Asn Tyr Phe Leu Phe Ser Leu Ala Cys Ala Asp Leu Ile Ile Gly
 1               5                  10                  15

Ala Phe Ser Met Asn Leu Tyr Thr Val Tyr Ile Ile Lys Gly Tyr Trp
             20                  25                  30

Pro Leu Gly Ala Val Val Cys Asp Leu Trp Leu
         35                  40

<210> SEQ ID NO 203
<211> LENGTH: 43
<212> TYPE: PRT
<213> ORGANISM: Artificial Sequence
<220> FEATURE:
<223> OTHER INFORMATION: M1 GPCR TM2

<400> SEQUENCE: 203

Asn Asn Tyr Phe Leu Leu Ser Leu Ala Cys Ala Asp Leu Ile Ile Gly
 1               5                  10                  15

Thr Phe Ser Met Asn Leu Tyr Thr Thr Tyr Leu Leu Met Gly His Trp
             20                  25                  30

Ala Leu Gly Thr Leu Ala Cys Asp Leu Trp Leu
         35                  40

<210> SEQ ID NO 204
<211> LENGTH: 43
<212> TYPE: PRT
<213> ORGANISM: Artificial Sequence
<220> FEATURE:
<223> OTHER INFORMATION: M3 GPCR TM2

<400> SEQUENCE: 204

Asn Asn Tyr Phe Leu Leu Ser Leu Ala Cys Ala Asp Leu Ile Ile Gly
 1               5                  10                  15

Val Ile Ser Met Asn Leu Phe Thr Thr Tyr Ile Ile Met Asn Arg Trp
             20                  25                  30

Ala Leu Gly Asn Leu Ala Cys Asp Leu Trp Leu
         35                  40

<210> SEQ ID NO 205
<211> LENGTH: 43
<212> TYPE: PRT
<213> ORGANISM: Artificial Sequence
<220> FEATURE:
<223> OTHER INFORMATION: M5 GPCR TM2

<400> SEQUENCE: 205

Asn Asn Tyr Tyr Leu Leu Ser Leu Ala Cys Ala Asp Leu Ile Ile Gly
 1               5                  10                  15

Ile Phe Ser Met Asn Leu Tyr Thr Thr Tyr Ile Leu Met Gly Arg Trp
             20                  25                  30

Ala Leu Gly Ser Leu Ala Cys Asp Leu Trp Leu
         35                  40
```

<210> SEQ ID NO 206
<211> LENGTH: 43
<212> TYPE: PRT
<213> ORGANISM: Artificial Sequence
<220> FEATURE:
<223> OTHER INFORMATION: H1 GPCR TM2

<400> SEQUENCE: 206

Gly Asn Leu Tyr Ile Val Ser Leu Ser Val Ala Asp Leu Ile Val Gly
1               5                   10                  15

Ala Val Val Met Pro Met Asn Ile Leu Tyr Leu Leu Met Ser Lys Trp
            20                  25                  30

Ser Leu Gly Arg Pro Leu Cys Leu Phe Trp Leu
        35                  40

<210> SEQ ID NO 207
<211> LENGTH: 43
<212> TYPE: PRT
<213> ORGANISM: Artificial Sequence
<220> FEATURE:
<223> OTHER INFORMATION: H2 GPCR TM2

<400> SEQUENCE: 207

Thr Asn Cys Phe Ile Val Ser Leu Ala Ile Thr Asp Leu Leu Leu Gly
1               5                   10                  15

Leu Leu Val Leu Pro Phe Ser Ala Ile Tyr Gln Leu Ser Cys Lys Trp
            20                  25                  30

Ser Phe Gly Lys Val Phe Cys Asn Ile Tyr Thr
        35                  40

<210> SEQ ID NO 208
<211> LENGTH: 43
<212> TYPE: PRT
<213> ORGANISM: Artificial Sequence
<220> FEATURE:
<223> OTHER INFORMATION: 5HT1A GPCR TM2

<400> SEQUENCE: 208

Ala Asn Tyr Leu Ile Gly Ser Leu Ala Val Thr Asp Leu Met Val Ser
1               5                   10                  15

Val Leu Val Leu Pro Met Ala Ala Leu Tyr Gln Val Leu Asn Lys Trp
            20                  25                  30

Thr Leu Gly Gln Val Thr Cys Asp Leu Phe Ile
        35                  40

<210> SEQ ID NO 209
<211> LENGTH: 43
<212> TYPE: PRT
<213> ORGANISM: Artificial Sequence
<220> FEATURE:
<223> OTHER INFORMATION: 5HT1B GPCR TM2

<400> SEQUENCE: 209

Ala Asn Tyr Leu Ile Ala Ser Leu Ala Val Thr Asp Leu Leu Val Ser
1               5                   10                  15

Ile Leu Val Met Pro Ile Ser Thr Met Tyr Thr Val Thr Gly Arg Trp
            20                  25                  30

Thr Leu Gly Gln Val Val Cys Asp Phe Trp Leu
        35                  40

```
<210> SEQ ID NO 210
<211> LENGTH: 43
<212> TYPE: PRT
<213> ORGANISM: Artificial Sequence
<220> FEATURE:
<223> OTHER INFORMATION: 5HT1D GPCR TM2

<400> SEQUENCE: 210

Ala Asn Tyr Leu Ile Gly Ser Leu Ala Thr Thr Asp Leu Leu Val Ser
  1               5                  10                  15

Ile Leu Val Met Pro Ile Ser Ile Ala Tyr Thr Ile Thr His Thr Trp
             20                  25                  30

Asn Phe Gly Gln Ile Leu Cys Asp Ile Trp Leu
         35                  40

<210> SEQ ID NO 211
<211> LENGTH: 43
<212> TYPE: PRT
<213> ORGANISM: Artificial Sequence
<220> FEATURE:
<223> OTHER INFORMATION: 5HT1E GPCR TM2

<400> SEQUENCE: 211

Ala Asn Tyr Leu Ile Cys Ser Leu Ala Val Thr Asp Leu Leu Val Ala
  1               5                  10                  15

Val Leu Val Met Pro Leu Ser Ile Ile Tyr Ile Val Met Asp Arg Trp
             20                  25                  30

Lys Leu Gly Tyr Phe Leu Cys Glu Val Trp Leu
         35                  40

<210> SEQ ID NO 212
<211> LENGTH: 43
<212> TYPE: PRT
<213> ORGANISM: Artificial Sequence
<220> FEATURE:
<223> OTHER INFORMATION: 5HT1F GPCR TM2

<400> SEQUENCE: 212

Ala Asn Tyr Leu Ile Cys Ser Leu Ala Val Thr Asp Phe Leu Val Ala
  1               5                  10                  15

Val Leu Val Met Pro Phe Ser Ile Val Tyr Ile Val Arg Glu Ser Trp
             20                  25                  30

Ile Met Gly Gln Val Val Cys Asp Ile Trp Leu
         35                  40

<210> SEQ ID NO 213
<211> LENGTH: 44
<212> TYPE: PRT
<213> ORGANISM: Artificial Sequence
<220> FEATURE:
<223> OTHER INFORMATION: 5HT2A GPCR TM2

<400> SEQUENCE: 213

Thr Asn Tyr Phe Leu Met Ser Leu Ala Ile Ala Asp Met Leu Leu Gly
  1               5                  10                  15

Phe Leu Val Met Pro Val Ser Met Leu Thr Ile Leu Tyr Gly Tyr Arg
             20                  25                  30

Trp Pro Leu Pro Ser Lys Leu Cys Ala Val Trp Ile
         35                  40
```

```
<210> SEQ ID NO 214
<211> LENGTH: 44
<212> TYPE: PRT
<213> ORGANISM: Artificial Sequence
<220> FEATURE:
<223> OTHER INFORMATION: 5HT2B GPCR TM2

<400> SEQUENCE: 214

Thr Asn Tyr Phe Leu Met Ser Leu Ala Val Ala Asp Leu Leu Val Gly
1               5                   10                  15

Leu Phe Val Met Pro Ile Ala Leu Leu Thr Ile Met Phe Glu Ala Met
            20                  25                  30

Trp Pro Leu Pro Leu Val Leu Cys Pro Ala Trp Leu
        35                  40

<210> SEQ ID NO 215
<211> LENGTH: 44
<212> TYPE: PRT
<213> ORGANISM: Artificial Sequence
<220> FEATURE:
<223> OTHER INFORMATION: 5HT2C GPCR TM2

<400> SEQUENCE: 215

Thr Asn Tyr Phe Leu Met Ser Leu Ala Ile Ala Asp Met Leu Val Gly
1               5                   10                  15

Leu Leu Val Met Pro Leu Ser Leu Leu Ala Ile Leu Tyr Asp Tyr Val
            20                  25                  30

Trp Pro Leu Pro Arg Tyr Leu Cys Pro Val Trp Ile
        35                  40

<210> SEQ ID NO 216
<211> LENGTH: 44
<212> TYPE: PRT
<213> ORGANISM: Artificial Sequence
<220> FEATURE:
<223> OTHER INFORMATION: 5HT5A GPCR TM2

<400> SEQUENCE: 216

Pro His Asn Leu Val Ala Ser Met Ala Val Ser Asp Val Leu Val Ala
1               5                   10                  15

Ala Leu Val Met Pro Leu Ser Leu Val His Glu Leu Ser Gly Arg Arg
            20                  25                  30

Trp Gln Leu Gly Arg Arg Leu Cys Gln Leu Trp Ile
        35                  40

<210> SEQ ID NO 217
<211> LENGTH: 45
<212> TYPE: PRT
<213> ORGANISM: Artificial Sequence
<220> FEATURE:
<223> OTHER INFORMATION: 5HT5Brat GPCR TM2

<400> SEQUENCE: 217

Pro His Asn Leu Val Ala Ser Thr Ala Val Ser Asp Val Leu Val Ala
1               5                   10                  15

Ala Leu Val Met Pro Leu Ser Leu Val Ser Glu Leu Ser Ala Gly Arg
            20                  25                  30

Arg Trp Gln Leu Gly Arg Ser Leu Cys His Val Trp Ile
        35                  40                  45
```

```
<210> SEQ ID NO 218
<211> LENGTH: 43
<212> TYPE: PRT
<213> ORGANISM: Artificial Sequence
<220> FEATURE:
<223> OTHER INFORMATION: 5HT6rat GPCR TM2

<400> SEQUENCE: 218

Ser Asn Phe Phe Leu Val Ser Leu Phe Thr Ser Asp Leu Met Val Gly
 1               5                  10                  15

Leu Val Val Met Pro Pro Ala Met Leu Asn Ala Leu Tyr Gly Arg Trp
            20                  25                  30

Val Leu Ala Arg Gly Leu Cys Leu Leu Trp Thr
        35                  40

<210> SEQ ID NO 219
<211> LENGTH: 44
<212> TYPE: PRT
<213> ORGANISM: Artificial Sequence
<220> FEATURE:
<223> OTHER INFORMATION: 5HT7 GPCR TM2

<400> SEQUENCE: 219

Ser Asn Tyr Leu Ile Val Ser Leu Ala Leu Ala Asp Leu Ser Val Ala
 1               5                  10                  15

Val Ala Val Met Pro Phe Val Ser Val Thr Asp Leu Ile Gly Gly Lys
            20                  25                  30

Trp Ile Phe Gly His Phe Phe Cys Asn Val Phe Ile
        35                  40

<210> SEQ ID NO 220
<211> LENGTH: 43
<212> TYPE: PRT
<213> ORGANISM: Artificial Sequence
<220> FEATURE:
<223> OTHER INFORMATION: alpha1A GPCR TM2

<400> SEQUENCE: 220

Thr Asn Tyr Phe Ile Val Asn Leu Ala Val Ala Asp Leu Leu Leu Ser
 1               5                  10                  15

Ala Thr Val Leu Pro Phe Ser Ala Thr Met Glu Val Leu Gly Phe Trp
            20                  25                  30

Ala Phe Gly Arg Ala Phe Cys Asp Val Trp Ala
        35                  40

<210> SEQ ID NO 221
<211> LENGTH: 43
<212> TYPE: PRT
<213> ORGANISM: Artificial Sequence
<220> FEATURE:
<223> OTHER INFORMATION: alpha1B GPCR TM2

<400> SEQUENCE: 221

Thr Asn Tyr Phe Ile Val Asn Leu Ala Met Ala Asp Leu Leu Leu Ser
 1               5                  10                  15

Phe Thr Val Leu Pro Phe Ser Ala Ala Leu Glu Val Leu Gly Tyr Trp
            20                  25                  30

Val Leu Gly Arg Ile Phe Cys Asp Ile Trp Ala
        35                  40
```

```
<210> SEQ ID NO 222
<211> LENGTH: 43
<212> TYPE: PRT
<213> ORGANISM: Artificial Sequence
<220> FEATURE:
<223> OTHER INFORMATION: alpha1C GPCR TM2

<400> SEQUENCE: 222

Thr His Tyr Tyr Ile Val Asn Leu Ala Val Ala Asp Leu Leu Thr
1               5                   10                  15

Ser Thr Val Leu Pro Phe Ser Ala Ile Phe Glu Val Leu Gly Tyr Trp
            20                  25                  30

Ala Phe Gly Arg Val Phe Cys Asn Ile Trp Ala
            35                  40

<210> SEQ ID NO 223
<211> LENGTH: 43
<212> TYPE: PRT
<213> ORGANISM: Artificial Sequence
<220> FEATURE:
<223> OTHER INFORMATION: alpha2A GPCR TM2

<400> SEQUENCE: 223

Gln Asn Leu Phe Leu Val Ser Leu Ala Ser Ala Asp Ile Leu Val Ala
1               5                   10                  15

Thr Leu Val Ile Pro Phe Ser Leu Ala Asn Glu Val Met Gly Tyr Trp
            20                  25                  30

Tyr Phe Gly Lys Ala Trp Cys Glu Ile Tyr Leu
            35                  40

<210> SEQ ID NO 224
<211> LENGTH: 43
<212> TYPE: PRT
<213> ORGANISM: Artificial Sequence
<220> FEATURE:
<223> OTHER INFORMATION: alpha2B GPCR TM2

<400> SEQUENCE: 224

Gln Asn Leu Phe Leu Val Ser Leu Ala Ala Ala Asp Ile Leu Val Ala
1               5                   10                  15

Thr Leu Ile Ile Pro Phe Ser Leu Ala Asn Glu Leu Leu Gly Tyr Trp
            20                  25                  30

Tyr Phe Arg Arg Thr Trp Cys Glu Val Tyr Leu
            35                  40

<210> SEQ ID NO 225
<211> LENGTH: 43
<212> TYPE: PRT
<213> ORGANISM: Artificial Sequence
<220> FEATURE:
<223> OTHER INFORMATION: alpha2C1 AND alpha2C2 GPCR TM2

<400> SEQUENCE: 225

Gln Asn Leu Phe Leu Val Ser Leu Ala Ser Ala Asp Ile Leu Val Ala
1               5                   10                  15

Thr Leu Val Met Pro Phe Ser Leu Ala Asn Glu Leu Met Ala Tyr Trp
            20                  25                  30

Tyr Phe Gly Gln Val Trp Cys Gly Val Tyr Leu
            35                  40
```

<210> SEQ ID NO 226
<211> LENGTH: 43
<212> TYPE: PRT
<213> ORGANISM: Artificial Sequence
<220> FEATURE:
<223> OTHER INFORMATION: beta1 GPCR TM2

<400> SEQUENCE: 226

Thr Asn Leu Phe Ile Met Ser Leu Ala Ser Ala Asp Leu Val Met Gly
1               5                   10                  15

Leu Leu Val Val Pro Phe Gly Ala Thr Ile Val Val Trp Gly Arg Trp
            20                  25                  30

Glu Tyr Gly Ser Phe Phe Cys Glu Leu Trp Thr
        35                  40

<210> SEQ ID NO 227
<211> LENGTH: 43
<212> TYPE: PRT
<213> ORGANISM: Artificial Sequence
<220> FEATURE:
<223> OTHER INFORMATION: beta2 GPCR TM2

<400> SEQUENCE: 227

Thr Asn Tyr Phe Ile Thr Ser Leu Ala Cys Ala Asp Leu Val Met Gly
1               5                   10                  15

Leu Ala Val Val Pro Phe Gly Ala Ala His Ile Leu Met Lys Met Trp
            20                  25                  30

Thr Phe Gly Asn Phe Trp Cys Glu Phe Trp Thr
        35                  40

<210> SEQ ID NO 228
<211> LENGTH: 43
<212> TYPE: PRT
<213> ORGANISM: Artificial Sequence
<220> FEATURE:
<223> OTHER INFORMATION: beta3 GPCR TM2

<400> SEQUENCE: 228

Thr Asn Val Phe Val Thr Ser Leu Ala Ala Ala Asp Leu Val Met Gly
1               5                   10                  15

Leu Leu Val Val Pro Pro Ala Ala Thr Leu Ala Leu Thr Gly His Trp
            20                  25                  30

Pro Leu Gly Ala Thr Gly Cys Glu Leu Trp Thr
        35                  40

<210> SEQ ID NO 229
<211> LENGTH: 43
<212> TYPE: PRT
<213> ORGANISM: Artificial Sequence
<220> FEATURE:
<223> OTHER INFORMATION: beta4turkey GPCR TM2

<400> SEQUENCE: 229

Thr Asn Val Phe Val Thr Ser Leu Ala Cys Ala Asp Leu Val Met Gly
1               5                   10                  15

Leu Leu Val Val Pro Pro Gly Ala Thr Ile Leu Leu Ser Gly His Trp
            20                  25                  30

Pro Tyr Gly Thr Val Val Cys Glu Leu Trp Thr
        35                  40

-continued

<210> SEQ ID NO 230
<211> LENGTH: 42
<212> TYPE: PRT
<213> ORGANISM: Artificial Sequence
<220> FEATURE:
<223> OTHER INFORMATION: D1A GPCR TM2

<400> SEQUENCE: 230

Thr Asn Phe Phe Val Ile Ser Leu Ala Val Ser Asp Leu Leu Val Ala
1               5                   10                  15

Val Leu Val Met Pro Trp Lys Ala Val Ala Glu Ile Ala Gly Phe Trp
            20                  25                  30

Pro Phe Gly Ser Phe Cys Asn Ile Trp Val
        35                  40

<210> SEQ ID NO 231
<211> LENGTH: 43
<212> TYPE: PRT
<213> ORGANISM: Artificial Sequence
<220> FEATURE:
<223> OTHER INFORMATION: D2 GPCR TM2

<400> SEQUENCE: 231

Thr Asn Tyr Leu Ile Val Ser Leu Ala Val Ala Asp Leu Leu Val Ala
1               5                   10                  15

Thr Leu Val Met Pro Trp Val Val Tyr Leu Glu Val Val Gly Glu Trp
            20                  25                  30

Lys Phe Ser Arg Ile His Cys Asp Ile Phe Val
        35                  40

<210> SEQ ID NO 232
<211> LENGTH: 44
<212> TYPE: PRT
<213> ORGANISM: Artificial Sequence
<220> FEATURE:
<223> OTHER INFORMATION: D3 GPCR TM2

<400> SEQUENCE: 232

Thr Asn Tyr Leu Val Val Ser Leu Ala Val Ala Asp Leu Leu Val Ala
1               5                   10                  15

Thr Leu Val Met Pro Trp Val Val Tyr Leu Glu Val Thr Gly Gly Val
            20                  25                  30

Trp Asn Phe Ser Arg Ile Cys Cys Asp Val Phe Val
        35                  40

<210> SEQ ID NO 233
<211> LENGTH: 44
<212> TYPE: PRT
<213> ORGANISM: Artificial Sequence
<220> FEATURE:
<223> OTHER INFORMATION: D4 GPCR TM2

<400> SEQUENCE: 233

Thr Asn Ser Phe Ile Val Ser Leu Ala Ala Ala Asp Leu Leu Leu Ala
1               5                   10                  15

Leu Leu Val Leu Pro Leu Phe Val Tyr Ser Glu Val Gln Gly Gly Ala
            20                  25                  30

Trp Leu Leu Ser Pro Arg Leu Cys Asp Ala Leu Met
        35                  40

```
<210> SEQ ID NO 234
<211> LENGTH: 42
<212> TYPE: PRT
<213> ORGANISM: Artificial Sequence
<220> FEATURE:
<223> OTHER INFORMATION: D5 GPCR TM2

<400> SEQUENCE: 234

Thr Asn Val Phe Ile Val Ser Leu Ala Val Ser Asp Leu Phe Val Ala
 1               5                  10                  15

Leu Leu Val Met Pro Trp Lys Ala Val Ala Glu Val Ala Gly Tyr Trp
            20                  25                  30

Pro Phe Gly Ala Phe Cys Asp Val Trp Val
            35                  40

<210> SEQ ID NO 235
<211> LENGTH: 41
<212> TYPE: PRT
<213> ORGANISM: Artificial Sequence
<220> FEATURE:
<223> OTHER INFORMATION: A1 GPCR TM2

<400> SEQUENCE: 235

Thr Phe Cys Phe Ile Val Ser Leu Ala Val Ala Asp Val Ala Val Gly
 1               5                  10                  15

Ala Leu Val Ile Pro Leu Ala Ile Leu Ile Asn Ile Gly Pro Gln Thr
            20                  25                  30

Tyr Phe His Thr Cys Leu Met Val Ala
            35                  40

<210> SEQ ID NO 236
<211> LENGTH: 41
<212> TYPE: PRT
<213> ORGANISM: Artificial Sequence
<220> FEATURE:
<223> OTHER INFORMATION: A2a GPCR TM2

<400> SEQUENCE: 236

Thr Asn Tyr Phe Val Val Ser Leu Ala Ala Ala Asp Ile Ala Val Gly
 1               5                  10                  15

Val Leu Ala Ile Pro Phe Ala Ile Thr Ile Ser Thr Gly Phe Cys Ala
            20                  25                  30

Ala Cys His Gly Cys Leu Phe Ile Ala
            35                  40

<210> SEQ ID NO 237
<211> LENGTH: 41
<212> TYPE: PRT
<213> ORGANISM: Artificial Sequence
<220> FEATURE:
<223> OTHER INFORMATION: A2b GPCR TM2

<400> SEQUENCE: 237

Thr Asn Tyr Phe Leu Val Ser Leu Ala Ala Ala Asp Val Ala Val Gly
 1               5                  10                  15

Leu Phe Ala Ile Pro Phe Ala Ile Thr Ile Ser Leu Gly Phe Cys Thr
            20                  25                  30

Asp Phe Tyr Gly Cys Leu Phe Leu Ala
            35                  40
```

<210> SEQ ID NO 238
<211> LENGTH: 41
<212> TYPE: PRT
<213> ORGANISM: Artificial Sequence
<220> FEATURE:
<223> OTHER INFORMATION: A3 GPCR TM2

<400> SEQUENCE: 238

Thr Phe Tyr Phe Ile Val Ser Leu Ala Leu Ala Asp Ile Ala Val Gly
1               5                   10                  15

Val Leu Val Met Pro Leu Ala Ile Val Val Ser Leu Gly Ile Thr Ile
            20                  25                  30

His Phe Tyr Ser Cys Leu Phe Met Thr
        35                  40

<210> SEQ ID NO 239
<211> LENGTH: 43
<212> TYPE: PRT
<213> ORGANISM: Artificial Sequence
<220> FEATURE:
<223> OTHER INFORMATION: OCdrome GPCR TM2

<400> SEQUENCE: 239

Gln Asn Phe Phe Ile Val Ser Leu Ala Val Ala Asp Leu Thr Val Ala
1               5                   10                  15

Leu Leu Val Leu Pro Phe Asn Val Ala Tyr Ser Ile Leu Gly Arg Trp
            20                  25                  30

Glu Phe Gly Ile His Leu Cys Lys Leu Trp Leu
        35                  40

<210> SEQ ID NO 240
<211> LENGTH: 49
<212> TYPE: PRT
<213> ORGANISM: Artificial Sequence
<220> FEATURE:
<223> OTHER INFORMATION: ACTH GPCR TM2

<400> SEQUENCE: 240

Met Tyr Phe Phe Ile Cys Ser Leu Ala Ile Ser Asp Met Leu Gly Ser
1               5                   10                  15

Leu Tyr Lys Ile Leu Glu Asn Ile Leu Ile Ile Leu Arg Asn Met Gly
            20                  25                  30

Tyr Leu Lys Pro Arg Gly Ser Phe Glu Thr Thr Ala Asp Ile Ile
        35                  40                  45

Asp

<210> SEQ ID NO 241
<211> LENGTH: 49
<212> TYPE: PRT
<213> ORGANISM: Artificial Sequence
<220> FEATURE:
<223> OTHER INFORMATION: MSH GPCR TM2

<400> SEQUENCE: 241

Met Tyr Cys Phe Ile Cys Cys Leu Ala Leu Ser Asp Leu Leu Val Ser
1               5                   10                  15

Gly Thr Asn Val Leu Glu Thr Ala Val Ile Leu Leu Glu Ala Gly
            20                  25                  30

Ala Leu Val Ala Arg Ala Ala Val Leu Gln Gln Leu Asp Asn Val Ile
        35                  40                  45

Asp

-continued

<210> SEQ ID NO 242
<211> LENGTH: 49
<212> TYPE: PRT
<213> ORGANISM: Artificial Sequence
<220> FEATURE:
<223> OTHER INFORMATION: MC3 GPCR TM2

<400> SEQUENCE: 242

Met Tyr Phe Phe Leu Cys Ser Leu Ala Val Ala Asp Met Leu Val Ser
1               5                   10                  15

Val Ser Asn Ala Leu Glu Thr Ile Met Ile Ala Ile Val His Ser Asp
            20                  25                  30

Asp Tyr Thr Phe Glu Asp Gln Phe Ile Gln His Met Asp Asn Ile Phe
        35                  40                  45

Asp

<210> SEQ ID NO 243
<211> LENGTH: 48
<212> TYPE: PRT
<213> ORGANISM: Artificial Sequence
<220> FEATURE:
<223> OTHER INFORMATION: MC4 GPCR TM2

<400> SEQUENCE: 243

Met Tyr Phe Phe Ile Cys Ser Leu Ala Val Ala Asp Met Leu Val Ser
1               5                   10                  15

Val Ser Asn Gly Ser Glu Thr Ile Ile Ile Thr Leu Leu Asn Ser Thr
            20                  25                  30

Asp Thr Asp Ala Gln Ser Phe Thr Val Asn Ile Asp Asn Val Ile Asp
        35                  40                  45

<210> SEQ ID NO 244
<211> LENGTH: 49
<212> TYPE: PRT
<213> ORGANISM: Artificial Sequence
<220> FEATURE:
<223> OTHER INFORMATION: MC5 GPCR TM2

<400> SEQUENCE: 244

Met Tyr Phe Phe Val Cys Ser Leu Ala Val Ala Asp Met Leu Val Ser
1               5                   10                  15

Met Ser Ser Ala Trp Glu Thr Ile Thr Ile Tyr Leu Leu Asn Asn Lys
            20                  25                  30

His Leu Val Ile Ala Asp Ala Phe Val Arg His Ile Asp Asn Val Phe
        35                  40                  45

Asp

<210> SEQ ID NO 245
<211> LENGTH: 43
<212> TYPE: PRT
<213> ORGANISM: Artificial Sequence
<220> FEATURE:
<223> OTHER INFORMATION: melatonin GPCR TM2

<400> SEQUENCE: 245

Gly Asn Ile Phe Val Val Ser Leu Ala Val Ala Asp Leu Val Val Ala
1               5                   10                  15

Ile Tyr Pro Tyr Pro Leu Val Leu Met Ser Ile Phe Asn Asn Gly Trp
            20                  25                  30

Asn Leu Gly Tyr Leu His Cys Gln Val Ser Gly
        35                  40

<210> SEQ ID NO 246
<211> LENGTH: 43
<212> TYPE: PRT
<213> ORGANISM: Artificial Sequence
<220> FEATURE:
<223> OTHER INFORMATION: oxytocin GPCR TM2

<400> SEQUENCE: 246

Leu Phe Phe Phe Met Lys His Leu Ser Ile Ala Asp Leu Val Val Ala
 1               5                  10                  15

Val Phe Gln Val Leu Pro Gln Leu Leu Trp Asp Ile Thr Phe Arg Phe
                20                  25                  30

Tyr Gly Pro Asp Leu Leu Cys Arg Leu Val Lys
            35                  40

<210> SEQ ID NO 247
<211> LENGTH: 43
<212> TYPE: PRT
<213> ORGANISM: Artificial Sequence
<220> FEATURE:
<223> OTHER INFORMATION: conopressinLs GPCR TM2

<400> SEQUENCE: 247

Met Gln Trp Phe Ile Ala His Leu Ala Phe Ala Asp Ile Phe Val Gly
 1               5                  10                  15

Phe Phe Asn Ile Leu Pro Gln Leu Ile Ser Asp Val Thr Ile Val Phe
                20                  25                  30

His Gly Asp Asp Phe Thr Cys Arg Phe Ile Lys
            35                  40

<210> SEQ ID NO 248
<211> LENGTH: 43
<212> TYPE: PRT
<213> ORGANISM: Artificial Sequence
<220> FEATURE:
<223> OTHER INFORMATION: V1A GPCR TM2

<400> SEQUENCE: 248

Met His Leu Phe Ile Arg His Leu Ser Leu Ala Asp Leu Ala Val Ala
 1               5                  10                  15

Phe Phe Gln Val Leu Pro Gln Met Cys Trp Asp Ile Thr Tyr Arg Phe
                20                  25                  30

Arg Gly Pro Asp Trp Leu Cys Arg Val Val Lys
            35                  40

<210> SEQ ID NO 249
<211> LENGTH: 43
<212> TYPE: PRT
<213> ORGANISM: Artificial Sequence
<220> FEATURE:
<223> OTHER INFORMATION: V1B GPCR TM2

<400> SEQUENCE: 249

Met His Leu Phe Val Leu His Leu Ala Leu Thr Asp Leu Ala Val Ala
 1               5                  10                  15

Leu Phe Gln Val Leu Pro Gln Leu Leu Trp Asp Ile Thr Tyr Arg Phe
                20                  25                  30

Gln Gly Pro Asp Leu Leu Cys Arg Ala Val Lys
            35                  40

<210> SEQ ID NO 250
<211> LENGTH: 43
<212> TYPE: PRT
<213> ORGANISM: Artificial Sequence
<220> FEATURE:
<223> OTHER INFORMATION: V2 GPCR TM2

<400> SEQUENCE: 250

Ile His Val Phe Ile Gly His Leu Cys Leu Ala Asp Leu Ala Val Ala
1               5                   10                  15

Leu Phe Gln Val Leu Pro Gln Leu Ala Trp Lys Ala Thr Asp Arg Phe
            20                  25                  30

Arg Gly Pro Asp Ala Leu Cys Arg Ala Val Lys
        35                  40

<210> SEQ ID NO 251
<211> LENGTH: 43
<212> TYPE: PRT
<213> ORGANISM: Artificial Sequence
<220> FEATURE:
<223> OTHER INFORMATION: CCK_A GPCR TM2

<400> SEQUENCE: 251

Thr Asn Ile Phe Leu Leu Ser Leu Ala Val Ser Asp Leu Met Leu Cys
1               5                   10                  15

Leu Phe Cys Met Pro Phe Asn Leu Ile Pro Asn Leu Leu Lys Asp Phe
            20                  25                  30

Ile Phe Gly Ser Ala Val Cys Lys Thr Thr Thr
        35                  40

<210> SEQ ID NO 252
<211> LENGTH: 43
<212> TYPE: PRT
<213> ORGANISM: Artificial Sequence
<220> FEATURE:
<223> OTHER INFORMATION: CCK_B GPCR TM2

<400> SEQUENCE: 252

Thr Asn Ala Phe Leu Leu Ser Leu Ala Val Ser Asp Leu Leu Leu Ala
1               5                   10                  15

Val Ala Cys Met Pro Phe Thr Leu Leu Pro Asn Leu Met Gly Thr Phe
            20                  25                  30

Ile Phe Gly Thr Val Ile Cys Lys Ala Val Ser
        35                  40

<210> SEQ ID NO 253
<211> LENGTH: 43
<212> TYPE: PRT
<213> ORGANISM: Artificial Sequence
<220> FEATURE:
<223> OTHER INFORMATION: NPY1 GPCR TM2

<400> SEQUENCE: 253

Thr Asn Ile Leu Ile Val Asn Leu Ser Phe Ser Asp Leu Leu Val Ala
1               5                   10                  15

Ile Met Cys Leu Pro Phe Thr Phe Val Tyr Thr Leu Met Asp His Trp
            20                  25                  30

Val Phe Gly Glu Ala Met Cys Lys Leu Asn Pro
        35                  40

-continued

```
<210> SEQ ID NO 254
<211> LENGTH: 45
<212> TYPE: PRT
<213> ORGANISM: Artificial Sequence
<220> FEATURE:
<223> OTHER INFORMATION: NTR GPCR TM2

<400> SEQUENCE: 254

Val His Tyr His Leu Gly Ser Leu Ala Leu Ser Asp Leu Leu Thr Leu
1               5                   10                  15

Leu Leu Ala Met Pro Val Glu Leu Tyr Asn Phe Ile Trp Val His His
            20                  25                  30

Pro Trp Ala Phe Gly Asp Ala Gly Cys Arg Gly Tyr Tyr
        35                  40                  45

<210> SEQ ID NO 255
<211> LENGTH: 43
<212> TYPE: PRT
<213> ORGANISM: Artificial Sequence
<220> FEATURE:
<223> OTHER INFORMATION: NK1 GPCR TM2

<400> SEQUENCE: 255

Thr Asn Tyr Phe Leu Val Asn Leu Ala Phe Ala Glu Ala Ser Met Ala
1               5                   10                  15

Ala Phe Asn Thr Val Val Asn Phe Thr Tyr Ala Val His Asn Glu Trp
            20                  25                  30

Tyr Tyr Gly Leu Phe Tyr Cys Lys Phe His Asn
        35                  40

<210> SEQ ID NO 256
<211> LENGTH: 43
<212> TYPE: PRT
<213> ORGANISM: Artificial Sequence
<220> FEATURE:
<223> OTHER INFORMATION: NK2 GPCR TM2

<400> SEQUENCE: 256

Thr Asn Tyr Phe Ile Val Asn Leu Ala Leu Ala Asp Leu Cys Met Ala
1               5                   10                  15

Ala Phe Asn Ala Ala Phe Asn Phe Val Tyr Ala Ser His Asn Ile Trp
            20                  25                  30

Tyr Phe Gly Arg Ala Phe Cys Tyr Phe Gln Asn
        35                  40

<210> SEQ ID NO 257
<211> LENGTH: 43
<212> TYPE: PRT
<213> ORGANISM: Artificial Sequence
<220> FEATURE:
<223> OTHER INFORMATION: NK3 GPCR TM2

<400> SEQUENCE: 257

Thr Asn Tyr Phe Leu Val Asn Leu Ala Phe Ser Asp Ala Ser Met Ala
1               5                   10                  15

Ala Phe Asn Thr Leu Val Asn Phe Ile Tyr Ala Leu His Ser Glu Trp
            20                  25                  30

Tyr Phe Gly Ala Asn Tyr Cys Arg Phe Gln Asn
        35                  40
```

<210> SEQ ID NO 258
<211> LENGTH: 43
<212> TYPE: PRT
<213> ORGANISM: Artificial Sequence
<220> FEATURE:
<223> OTHER INFORMATION: blueops GPCR TM2

<400> SEQUENCE: 258

Leu Asn Tyr Ile Leu Val Asn Val Ser Phe Gly Gly Phe Leu Leu Cys
1               5                   10                  15

Ile Phe Ser Val Phe Pro Val Phe Val Ala Ser Cys Asn Gly Tyr Phe
            20                  25                  30

Val Phe Gly Arg His Val Cys Ala Leu Glu Gly
        35                  40

<210> SEQ ID NO 259
<211> LENGTH: 43
<212> TYPE: PRT
<213> ORGANISM: Artificial Sequence
<220> FEATURE:
<223> OTHER INFORMATION: greenops GPCR TM2

<400> SEQUENCE: 259

Leu Asn Trp Ile Leu Val Asn Leu Ala Val Ala Asp Leu Ala Glu Thr
1               5                   10                  15

Val Ile Ala Ser Thr Ile Ser Val Val Asn Gln Val Tyr Gly Tyr Phe
            20                  25                  30

Val Leu Gly His Pro Met Cys Val Leu Glu Gly
        35                  40

<210> SEQ ID NO 260
<211> LENGTH: 43
<212> TYPE: PRT
<213> ORGANISM: Artificial Sequence
<220> FEATURE:
<223> OTHER INFORMATION: redops GPCR TM2

<400> SEQUENCE: 260

Leu Asn Trp Ile Leu Val Asn Leu Ala Val Ala Asp Leu Ala Glu Thr
1               5                   10                  15

Val Ile Ala Ser Thr Ile Ser Ile Val Asn Gln Val Ser Gly Tyr Phe
            20                  25                  30

Val Leu Gly His Pro Met Cys Val Leu Glu Gly
        35                  40

<210> SEQ ID NO 261
<211> LENGTH: 43
<212> TYPE: PRT
<213> ORGANISM: Artificial Sequence
<220> FEATURE:
<223> OTHER INFORMATION: rhodopsin GPCR TM2

<400> SEQUENCE: 261

Leu Asn Tyr Ile Leu Leu Asn Leu Ala Val Ala Asp Leu Phe Met Val
1               5                   10                  15

Leu Gly Gly Phe Thr Ser Thr Leu Tyr Thr Ser Leu His Gly Tyr Phe
            20                  25                  30

Val Phe Gly Pro Thr Gly Cys Asn Leu Glu Gly
        35                  40

-continued

```
<210> SEQ ID NO 262
<211> LENGTH: 43
<212> TYPE: PRT
<213> ORGANISM: Artificial Sequence
<220> FEATURE:
<223> OTHER INFORMATION: violetopsGg GPCR TM2

<400> SEQUENCE: 262

Leu Asn Tyr Ile Leu Val Asn Ile Ser Ala Ser Gly Phe Val Ser Cys
1               5                   10                  15

Val Leu Ser Val Phe Val Val Phe Val Ala Ser Ala Arg Gly Tyr Phe
            20                  25                  30

Val Phe Gly Lys Arg Val Cys Glu Leu Glu Ala
        35                  40

<210> SEQ ID NO 263
<211> LENGTH: 43
<212> TYPE: PRT
<213> ORGANISM: Artificial Sequence
<220> FEATURE:
<223> OTHER INFORMATION: opsin_crab GPCR TM2

<400> SEQUENCE: 263

Thr Asn Leu Leu Val Val Asn Leu Ala Phe Ser Asp Phe Cys Met Met
1               5                   10                  15

Ala Phe Met Met Pro Thr Met Thr Ser Asn Cys Phe Ala Glu Thr Trp
            20                  25                  30

Ile Leu Gly Pro Phe Met Cys Glu Val Tyr Gly
        35                  40

<210> SEQ ID NO 264
<211> LENGTH: 48
<212> TYPE: PRT
<213> ORGANISM: Artificial Sequence
<220> FEATURE:
<223> OTHER INFORMATION: ET_Aprec GPCR TM2

<400> SEQUENCE: 264

Pro Asn Ala Leu Ile Ala Ser Leu Ala Leu Gly Asp Leu Ile Tyr Val
1               5                   10                  15

Val Ile Asp Leu Pro Ile Asn Val Phe Lys Leu Leu Ala Gly Arg Trp
            20                  25                  30

Pro Phe Asp His Asn Asp Phe Gly Val Phe Leu Cys Lys Leu Phe Pro
        35                  40                  45

<210> SEQ ID NO 265
<211> LENGTH: 43
<212> TYPE: PRT
<213> ORGANISM: Artificial Sequence
<220> FEATURE:
<223> OTHER INFORMATION: ET_Bprec GPCR TM2

<400> SEQUENCE: 265

Pro Asn Ile Leu Ile Ala Ser Leu Ala Leu Gly Asp Leu Leu His Ile
1               5                   10                  15

Val Ile Asp Ile Pro Ile Asn Val Tyr Lys Leu Leu Ala Glu Asp Trp
            20                  25                  30

Pro Phe Gly Ala Glu Met Cys Lys Leu Val Pro
        35                  40
```

```
<210> SEQ ID NO 266
<211> LENGTH: 39
<212> TYPE: PRT
<213> ORGANISM: Artificial Sequence
<220> FEATURE:
<223> OTHER INFORMATION: ET_Cfrog GPCR TM2

<400> SEQUENCE: 266

Pro Asn Val Leu Ile Ala Ser Leu Ala Leu Gly Asp Leu Phe Tyr Ile
1               5                   10                  15

Leu Ile Ala Ile Pro Ile Ile Ser Ile Ser Phe Trp Leu Ser Thr Gly
            20                  25                  30

His Ser Glu Tyr Ile Tyr Gln
        35

<210> SEQ ID NO 267
<211> LENGTH: 43
<212> TYPE: PRT
<213> ORGANISM: Artificial Sequence
<220> FEATURE:
<223> OTHER INFORMATION: galatin GPCR TM2

<400> SEQUENCE: 267

Thr Asn Leu Phe Ile Leu Asn Leu Ser Ile Ala Asp Leu Ala Tyr Leu
1               5                   10                  15

Leu Phe Cys Ile Pro Phe Gln Ala Thr Val Tyr Ala Leu Pro Thr Trp
            20                  25                  30

Val Leu Gly Ala Phe Ile Cys Lys Phe Ile His
        35                  40

<210> SEQ ID NO 268
<211> LENGTH: 43
<212> TYPE: PRT
<213> ORGANISM: Artificial Sequence
<220> FEATURE:
<223> OTHER INFORMATION: NMBGPCR TM2

<400> SEQUENCE: 268

Pro Asn Ile Phe Ile Ser Asn Leu Ala Ala Gly Asp Leu Leu Leu Leu
1               5                   10                  15

Leu Thr Cys Val Pro Val Asp Ala Ser Arg Tyr Phe Phe Asp Glu Trp
            20                  25                  30

Met Phe Gly Lys Val Gly Cys Lys Leu Ile Pro
        35                  40

<210> SEQ ID NO 269
<211> LENGTH: 43
<212> TYPE: PRT
<213> ORGANISM: Artificial Sequence
<220> FEATURE:
<223> OTHER INFORMATION: GRP GPCR TM2

<400> SEQUENCE: 269

Pro Asn Leu Phe Ile Ser Ser Leu Ala Leu Gly Asp Leu Leu Leu Leu
1               5                   10                  15

Ile Thr Cys Ala Pro Val Asp Ala Ser Arg Tyr Leu Ala Asp Arg Trp
            20                  25                  30

Leu Phe Gly Arg Ile Gly Cys Lys Leu Ile Pro
        35                  40
```

<210> SEQ ID NO 270
<211> LENGTH: 43
<212> TYPE: PRT
<213> ORGANISM: Artificial Sequence
<220> FEATURE:
<223> OTHER INFORMATION: BRS3 GPCR TM2

<400> SEQUENCE: 270

Pro Asn Ile Phe Ile Thr Ser Leu Ala Phe Gly Asp Leu Leu Leu Leu
1               5                   10                  15

Leu Thr Cys Val Pro Val Asp Ala Thr His Tyr Leu Ala Glu Gly Trp
            20                  25                  30

Leu Phe Gly Arg Ile Gly Cys Lys Val Leu Ser
        35                  40

<210> SEQ ID NO 271
<211> LENGTH: 42
<212> TYPE: PRT
<213> ORGANISM: Artificial Sequence
<220> FEATURE:
<223> OTHER INFORMATION: deltaOP GPCR TM2

<400> SEQUENCE: 271

Thr Asn Ile Tyr Ile Phe Asn Leu Ala Leu Ala Asp Ala Leu Ala Thr
1               5                   10                  15

Ser Thr Leu Pro Phe Gln Ser Ala Lys Tyr Leu Met Glu Thr Trp Pro
            20                  25                  30

Phe Gly Glu Leu Leu Cys Lys Ala Val Leu
        35                  40

<210> SEQ ID NO 272
<211> LENGTH: 42
<212> TYPE: PRT
<213> ORGANISM: Artificial Sequence
<220> FEATURE:
<223> OTHER INFORMATION: kappaOP GPCR TM2

<400> SEQUENCE: 272

Thr Asn Ile Tyr Ile Phe Asn Leu Ala Leu Ala Asp Ala Leu Val Thr
1               5                   10                  15

Thr Thr Met Pro Phe Gln Ser Thr Val Tyr Leu Met Asn Ser Trp Pro
            20                  25                  30

Phe Gly Asp Val Leu Cys Lys Ile Val Ile
        35                  40

<210> SEQ ID NO 273
<211> LENGTH: 42
<212> TYPE: PRT
<213> ORGANISM: Artificial Sequence
<220> FEATURE:
<223> OTHER INFORMATION: muOP GPCR TM2

<400> SEQUENCE: 273

Thr Asn Ile Tyr Ile Phe Asn Leu Ala Leu Ala Asp Ala Leu Ala Thr
1               5                   10                  15

Ser Thr Leu Pro Phe Gln Ser Val Asn Tyr Leu Met Gly Thr Trp Pro
            20                  25                  30

Phe Gly Thr Ile Leu Cys Lys Ile Val Ile
        35                  40

-continued

<210> SEQ ID NO 274
<211> LENGTH: 42
<212> TYPE: PRT
<213> ORGANISM: Artificial Sequence
<220> FEATURE:
<223> OTHER INFORMATION: OPRX GPCR TM2

<400> SEQUENCE: 274

Thr Asn Ile Tyr Ile Phe Asn Leu Ala Leu Ala Asp Thr Leu Val Leu
 1               5                  10                  15

Leu Thr Leu Pro Phe Gln Gly Thr Asp Ile Leu Leu Gly Phe Trp Pro
            20                  25                  30

Phe Gly Asn Ala Leu Cys Lys Thr Val Ile
        35                  40

<210> SEQ ID NO 275
<211> LENGTH: 42
<212> TYPE: PRT
<213> ORGANISM: Artificial Sequence
<220> FEATURE:
<223> OTHER INFORMATION: CB1 GPCR TM2

<400> SEQUENCE: 275

Ser Tyr His Phe Ile Gly Ser Leu Ala Val Ala Asp Leu Leu Gly Ser
 1               5                  10                  15

Val Ile Phe Val Tyr Ser Phe Ile Asp Phe His Val Phe His Arg Lys
            20                  25                  30

Asp Ser Arg Asn Val Phe Leu Phe Lys Leu
        35                  40

<210> SEQ ID NO 276
<211> LENGTH: 42
<212> TYPE: PRT
<213> ORGANISM: Artificial Sequence
<220> FEATURE:
<223> OTHER INFORMATION: CB2 GPCR TM2

<400> SEQUENCE: 276

Ser Tyr Leu Phe Ile Gly Ser Leu Ala Gly Ala Asp Phe Leu Ala Ser
 1               5                  10                  15

Val Val Phe Ala Cys Ser Phe Val Asn Phe His Val Phe His Gly Val
            20                  25                  30

Asp Ser Lys Ala Val Phe Leu Leu Lys Ile
        35                  40

<210> SEQ ID NO 277
<211> LENGTH: 42
<212> TYPE: PRT
<213> ORGANISM: Artificial Sequence
<220> FEATURE:
<223> OTHER INFORMATION: SSTR1 GPCR TM2

<400> SEQUENCE: 277

Thr Asn Ile Tyr Ile Leu Asn Leu Ala Ile Ala Asp Glu Leu Leu Met
 1               5                  10                  15

Leu Ser Val Pro Phe Leu Val Thr Ser Thr Leu Leu Arg His Trp Pro
            20                  25                  30

Phe Gly Ala Leu Leu Cys Arg Leu Val Leu
        35                  40

<210> SEQ ID NO 278
<211> LENGTH: 42
<212> TYPE: PRT
<213> ORGANISM: Artificial Sequence
<220> FEATURE:
<223> OTHER INFORMATION: SSTR2 GPCR TM2

<400> SEQUENCE: 278

Thr Asn Ile Tyr Ile Leu Asn Leu Ala Ile Ala Asp Glu Leu Phe Met
1               5                   10                  15

Leu Gly Leu Pro Phe Leu Ala Met Gln Val Ala Leu Val His Trp Pro
            20                  25                  30

Phe Gly Lys Ala Ile Cys Arg Val Val Met
        35                  40

<210> SEQ ID NO 279
<211> LENGTH: 42
<212> TYPE: PRT
<213> ORGANISM: Artificial Sequence
<220> FEATURE:
<223> OTHER INFORMATION: SSTR3 GPCR TM2

<400> SEQUENCE: 279

Thr Asn Val Tyr Ile Leu Asn Leu Ala Leu Ala Asp Glu Leu Phe Met
1               5                   10                  15

Leu Gly Leu Pro Phe Leu Ala Ala Gln Asn Ala Leu Ser Tyr Trp Pro
            20                  25                  30

Phe Gly Ser Leu Met Cys Arg Leu Val Met
        35                  40

<210> SEQ ID NO 280
<211> LENGTH: 42
<212> TYPE: PRT
<213> ORGANISM: Artificial Sequence
<220> FEATURE:
<223> OTHER INFORMATION: SSTR4 GPCR TM2

<400> SEQUENCE: 280

Thr Asn Ile Tyr Leu Leu Asn Leu Ala Val Ala Asp Glu Leu Phe Met
1               5                   10                  15

Leu Ser Val Pro Phe Val Ala Ser Ser Ala Ala Leu Arg His Trp Pro
            20                  25                  30

Phe Gly Ser Val Leu Cys Arg Ala Val Leu
        35                  40

<210> SEQ ID NO 281
<211> LENGTH: 42
<212> TYPE: PRT
<213> ORGANISM: Artificial Sequence
<220> FEATURE:
<223> OTHER INFORMATION: SSTR5 GPCR TM2

<400> SEQUENCE: 281

Thr Asn Ile Tyr Ile Leu Asn Leu Ala Val Ala Asp Val Leu Tyr Met
1               5                   10                  15

Leu Gly Leu Pro Phe Leu Ala Thr Gln Asn Ala Ala Ser Phe Trp Pro
            20                  25                  30

Phe Gly Pro Val Leu Cys Arg Leu Val Met
        35                  40

```
<210> SEQ ID NO 282
<211> LENGTH: 41
<212> TYPE: PRT
<213> ORGANISM: Artificial Sequence
<220> FEATURE:
<223> OTHER INFORMATION: IL8A and IL8B GPCR TM2

<400> SEQUENCE: 282
```

Thr Asp Val Tyr Leu Leu Asn Leu Ala Leu Ala Asp Leu Leu Phe Ala
1               5                   10                  15

Leu Thr Leu Pro Ile Trp Ala Ala Ser Lys Val Asn Gly Trp Ile Phe
            20                  25                  30

Gly Thr Phe Leu Cys Lys Val Val Ser
        35                  40

```
<210> SEQ ID NO 283
<211> LENGTH: 43
<212> TYPE: PRT
<213> ORGANISM: Artificial Sequence
<220> FEATURE:
<223> OTHER INFORMATION: AT1a GPCR TM2

<400> SEQUENCE: 283
```

Ala Ser Val Phe Leu Leu Asn Leu Ala Leu Ala Asp Leu Cys Phe Leu
1               5                   10                  15

Leu Thr Leu Pro Leu Trp Ala Val Tyr Thr Ala Met Glu Tyr Arg Trp
            20                  25                  30

Pro Phe Gly Asn Tyr Leu Cys Lys Ile Ala Ser
        35                  40

```
<210> SEQ ID NO 284
<211> LENGTH: 43
<212> TYPE: PRT
<213> ORGANISM: Artificial Sequence
<220> FEATURE:
<223> OTHER INFORMATION: AT1brat GPCR TM2

<400> SEQUENCE: 284
```

Ala Ser Val Phe Leu Leu Asn Leu Ala Leu Ala Asp Leu Cys Phe Leu
1               5                   10                  15

Leu Thr Leu Pro Leu Trp Ala Val Tyr Thr Ala Met Glu Tyr Arg Trp
            20                  25                  30

Pro Phe Gly Asn His Leu Cys Lys Ile Ala Ser
        35                  40

```
<210> SEQ ID NO 285
<211> LENGTH: 43
<212> TYPE: PRT
<213> ORGANISM: Artificial Sequence
<220> FEATURE:
<223> OTHER INFORMATION: AT2 GPCR TM2

<400> SEQUENCE: 285
```

Ser Ser Ile Tyr Ile Phe Asn Leu Ala Val Ala Asp Leu Leu Leu Leu
1               5                   10                  15

Ala Thr Leu Pro Leu Trp Ala Thr Tyr Tyr Ser Tyr Arg Tyr Asp Trp
            20                  25                  30

Leu Phe Gly Pro Val Met Cys Lys Val Phe Gly
        35                  40

<210> SEQ ID NO 286
<211> LENGTH: 43
<212> TYPE: PRT
<213> ORGANISM: Artificial Sequence
<220> FEATURE:
<223> OTHER INFORMATION: BK1 GPCR TM2

<400> SEQUENCE: 286

```
Ala Glu Ile Tyr Leu Ala Asn Leu Ala Ala Ser Asp Leu Val Phe Val
 1               5                  10                  15

Leu Gly Leu Pro Phe Trp Ala Glu Asn Ile Trp Asn Gln Phe Asn Trp
             20                  25                  30

Pro Phe Gly Ala Leu Leu Cys Arg Val Ile Asn
         35                  40
```

<210> SEQ ID NO 287
<211> LENGTH: 43
<212> TYPE: PRT
<213> ORGANISM: Artificial Sequence
<220> FEATURE:
<223> OTHER INFORMATION: BK2 GPCR TM2

<400> SEQUENCE: 287

```
Ala Glu Ile Tyr Leu Gly Asn Leu Ala Ala Asp Leu Ile Leu Ala
 1               5                  10                  15

Cys Gly Leu Pro Phe Trp Ala Ile Thr Ile Ser Asn Asn Phe Asp Trp
             20                  25                  30

Leu Phe Gly Glu Thr Leu Cys Arg Val Val Asn
         35                  40
```

<210> SEQ ID NO 288
<211> LENGTH: 42
<212> TYPE: PRT
<213> ORGANISM: Artificial Sequence
<220> FEATURE:
<223> OTHER INFORMATION: P2Y7 GPCR TM2

<400> SEQUENCE: 288

```
Thr Ala Leu Met Val Leu Asn Leu Ala Leu Ala Asp Leu Ala Val Leu
 1               5                  10                  15

Leu Thr Ala Pro Phe Phe Leu His Phe Leu Ala Gln Gly Thr Trp Ser
             20                  25                  30

Phe Gly Leu Ala Gly Cys Arg Leu Cys His
         35                  40
```

<210> SEQ ID NO 289
<211> LENGTH: 43
<212> TYPE: PRT
<213> ORGANISM: Artificial Sequence
<220> FEATURE:
<223> OTHER INFORMATION: P2Y6 GPCR TM2

<400> SEQUENCE: 289

```
Ser Ala Val Tyr Thr Leu Asn Leu Ala Leu Ala Asp Leu Leu Tyr Ala
 1               5                  10                  15

Cys Ser Leu Pro Leu Leu Ile Tyr Asn Tyr Ala Arg Gly Asp His Trp
             20                  25                  30

Pro Phe Gly Asp Leu Ala Cys Arg Leu Val Arg
         35                  40
```

```
<210> SEQ ID NO 290
<211> LENGTH: 42
<212> TYPE: PRT
<213> ORGANISM: Artificial Sequence
<220> FEATURE:
<223> OTHER INFORMATION: P2Y5 GPCR TM2

<400> SEQUENCE: 290

Thr Thr Thr Tyr Met Leu Asn Leu Ala Ile Ser Asp Leu Leu Phe Val
1               5                   10                  15

Phe Thr Leu Pro Phe Arg Ile Tyr Tyr Phe Val Val Arg Asn Trp Pro
            20                  25                  30

Phe Gly Asp Val Leu Cys Lys Ile Ser Val
        35                  40

<210> SEQ ID NO 291
<211> LENGTH: 43
<212> TYPE: PRT
<213> ORGANISM: Artificial Sequence
<220> FEATURE:
<223> OTHER INFORMATION: P2Y4 GPCR TM2

<400> SEQUENCE: 291

Thr Ala Thr Tyr Met Phe His Leu Ala Leu Ser Asp Thr Leu Tyr Val
1               5                   10                  15

Val Ser Leu Pro Thr Leu Ile Tyr Tyr Ala Ala His Asn His Trp
            20                  25                  30

Pro Phe Gly Thr Glu Ile Cys Lys Phe Val Arg
        35                  40

<210> SEQ ID NO 292
<211> LENGTH: 43
<212> TYPE: PRT
<213> ORGANISM: Artificial Sequence
<220> FEATURE:
<223> OTHER INFORMATION: P2Y3chick GPCR TM2

<400> SEQUENCE: 292

Thr Thr Ile Tyr Met Leu Asn Leu Ala Met Ala Asp Leu Leu Tyr Val
1               5                   10                  15

Cys Ser Leu Pro Leu Leu Ile Tyr Asn Tyr Thr Gln Lys Asp Tyr Trp
            20                  25                  30

Pro Phe Gly Asp Phe Thr Cys Lys Phe Val Arg
        35                  40

<210> SEQ ID NO 293
<211> LENGTH: 43
<212> TYPE: PRT
<213> ORGANISM: Artificial Sequence
<220> FEATURE:
<223> OTHER INFORMATION: P2Y2 GPCR TM2

<400> SEQUENCE: 293

Ser Thr Thr Tyr Met Phe His Leu Ala Val Ser Asp Ala Leu Tyr Ala
1               5                   10                  15

Ala Ser Leu Pro Leu Leu Val Tyr Tyr Ala Arg Gly Asp His Trp
            20                  25                  30

Pro Phe Ser Thr Val Leu Cys Lys Leu Val Arg
        35                  40
```

<210> SEQ ID NO 294
<211> LENGTH: 43
<212> TYPE: PRT
<213> ORGANISM: Artificial Sequence
<220> FEATURE:
<223> OTHER INFORMATION: P2Y1 GPCR TM2

<400> SEQUENCE: 294

Ile Ser Val Tyr Met Phe Asn Leu Ala Leu Ala Asp Phe Leu Tyr Val
1               5                   10                  15

Leu Thr Leu Pro Ala Leu Ile Phe Tyr Tyr Phe Asn Lys Thr Asp Trp
            20                  25                  30

Ile Phe Gly Asp Ala Met Cys Lys Leu Gln Arg
        35                  40

<210> SEQ ID NO 295
<211> LENGTH: 43
<212> TYPE: PRT
<213> ORGANISM: Artificial Sequence
<220> FEATURE:
<223> OTHER INFORMATION: THRprec GPCR TM2

<400> SEQUENCE: 295

Ala Val Val Tyr Met Leu His Leu Ala Thr Ala Asp Val Leu Phe Val
1               5                   10                  15

Ser Val Leu Pro Phe Lys Ile Ser Tyr Tyr Phe Ser Gly Ser Asp Trp
            20                  25                  30

Gln Phe Gly Ser Glu Leu Cys Arg Phe Val Thr
        35                  40

<210> SEQ ID NO 296
<211> LENGTH: 42
<212> TYPE: PRT
<213> ORGANISM: Artificial Sequence
<220> FEATURE:
<223> OTHER INFORMATION: C5a GPCR TM2

<400> SEQUENCE: 296

Asn Ala Ile Trp Phe Leu Asn Leu Ala Val Ala Asp Phe Leu Ser Cys
1               5                   10                  15

Leu Ala Leu Pro Ile Leu Phe Thr Ser Ile Val Gln His His Trp Pro
            20                  25                  30

Phe Gly Gly Ala Ala Cys Ser Ile Leu Pro
        35                  40

<210> SEQ ID NO 297
<211> LENGTH: 39
<212> TYPE: PRT
<213> ORGANISM: Artificial Sequence
<220> FEATURE:
<223> OTHER INFORMATION: GP01mouse AND R334rat GPCR TM2

<400> SEQUENCE: 297

Met Phe Leu Leu Ile Gly Ser Leu Ala Leu Ala Asp Leu Leu Ala Gly
1               5                   10                  15

Leu Gly Leu Ile Ile Asn Phe Val Phe Ala Tyr Leu Leu Gln Ser Glu
            20                  25                  30

Ala Thr Lys Leu Val Thr Ile
        35

<210> SEQ ID NO 298
<211> LENGTH: 39
<212> TYPE: PRT
<213> ORGANISM: Artificial Sequence
<220> FEATURE:
<223> OTHER INFORMATION: GP21mouse GPCR TM2

<400> SEQUENCE: 298

Met Phe Leu Leu Val Gly Ser Leu Ala Val Ala Asp Leu Leu Ala Gly
1               5                   10                  15

Leu Gly Leu Val Leu His Phe Ala Ala Asp Phe Cys Ile Gly Ser Pro
            20                  25                  30

Glu Met Ser Leu Met Leu Val
        35

<210> SEQ ID NO 299
<211> LENGTH: 43
<212> TYPE: PRT
<213> ORGANISM: Artificial Sequence
<220> FEATURE:
<223> OTHER INFORMATION: GCRCmouse GPCR TM2

<400> SEQUENCE: 299

Thr Ser Leu Phe Ile Val Asn Leu Ala Val Ala Asp Ile Met Ile Thr
1               5                   10                  15

Leu Leu Asn Thr Pro Phe Thr Leu Val Arg Phe Val Asn Ser Thr Trp
            20                  25                  30

Val Phe Gly Lys Gly Met Cys His Val Ser Arg
        35                  40

<210> SEQ ID NO 300
<211> LENGTH: 43
<212> TYPE: PRT
<213> ORGANISM: Artificial Sequence
<220> FEATURE:
<223> OTHER INFORMATION: TXKR GPCR TM2

<400> SEQUENCE: 300

Thr Asn Ser Phe Leu Val Asn Leu Ala Phe Ala Asp Ala Ala Met Ala
1               5                   10                  15

Ala Leu Asn Ala Leu Val Asn Phe Ile Tyr Ala Leu His Gly Glu Trp
            20                  25                  30

Tyr Phe Gly Ala Asn Tyr Cys Arg Phe Gln Asn
        35                  40

<210> SEQ ID NO 301
<211> LENGTH: 43
<212> TYPE: PRT
<213> ORGANISM: Artificial Sequence
<220> FEATURE:
<223> OTHER INFORMATION: G10Drat GPCR TM2

<400> SEQUENCE: 301

Leu Asn Leu Tyr Ile Leu Asn Met Ala Val Ala Asp Leu Gly Ile Ile
1               5                   10                  15

Leu Ser Leu Pro Val Trp Met Leu Glu Val Met Leu Glu Tyr Thr Trp
            20                  25                  30

Leu Trp Gly Ser Phe Ser Cys Arg Phe Ile His
        35                  40

```
<210> SEQ ID NO 302
<211> LENGTH: 42
<212> TYPE: PRT
<213> ORGANISM: Artificial Sequence
<220> FEATURE:
<223> OTHER INFORMATION: RDC1 GPCR TM2

<400> SEQUENCE: 302

His Cys Tyr Ile Leu Asn Leu Ala Ile Ala Asp Leu Trp Val Val Leu
 1               5                  10                  15

Thr Ile Pro Val Trp Val Val Ser Leu Val Gln His Asn Gln Trp Pro
            20                  25                  30

Met Gly Glu Leu Thr Cys Lys Val Thr His
        35                  40

<210> SEQ ID NO 303
<211> LENGTH: 39
<212> TYPE: PRT
<213> ORGANISM: Artificial Sequence
<220> FEATURE:
<223> OTHER INFORMATION: BLR1 GPCR TM2

<400> SEQUENCE: 303

Thr Phe Leu Phe His Leu Ala Val Ala Asp Leu Leu Leu Val Phe Ile
 1               5                  10                  15

Leu Pro Phe Ala Val Ala Glu Gly Ser Val Gly Trp Val Leu Gly Thr
            20                  25                  30

Phe Leu Cys Lys Thr Val Ile
        35

<210> SEQ ID NO 304
<211> LENGTH: 36
<212> TYPE: PRT
<213> ORGANISM: Artificial Sequence
<220> FEATURE:
<223> OTHER INFORMATION: CL5 and LCR1GPCR TM2

<400> SEQUENCE: 304

Leu His Leu Ser Val Ala Asp Leu Leu Phe Val Ile Thr Leu Pro Phe
 1               5                  10                  15

Trp Ala Val Asp Ala Val Ala Asn Trp Tyr Phe Gly Asn Phe Leu Cys
            20                  25                  30

Lys Ala Val His
        35

<210> SEQ ID NO 305
<211> LENGTH: 37
<212> TYPE: PRT
<213> ORGANISM: Artificial Sequence
<220> FEATURE:
<223> OTHER INFORMATION: EBI1 GPCR TM2

<400> SEQUENCE: 305

Leu Leu Asn Leu Ala Val Ala Asp Ile Leu Phe Leu Leu Thr Leu Pro
 1               5                  10                  15

Phe Trp Ala Tyr Ser Ala Ala Lys Ser Trp Val Phe Gly Val His Phe
            20                  25                  30

Cys Lys Leu Ile Phe
        35
```

-continued

<210> SEQ ID NO 306
<211> LENGTH: 37
<212> TYPE: PRT
<213> ORGANISM: Artificial Sequence
<220> FEATURE:
<223> OTHER INFORMATION: RBS1rat GPCR TM2

<400> SEQUENCE: 306

Leu Leu Asn Leu Ala Leu Ser Asp Leu Leu Phe Val Ala Thr Leu Pro
1               5                   10                  15

Phe Trp Thr His Tyr Leu Ile Ser His Glu Gly Leu His Asn Ala Met
            20                  25                  30

Cys Lys Leu Thr Thr
        35

<210> SEQ ID NO 307
<211> LENGTH: 39
<212> TYPE: PRT
<213> ORGANISM: Artificial Sequence
<220> FEATURE:
<223> OTHER INFORMATION: EBI2 GPCR TM2

<400> SEQUENCE: 307

Ser Thr Asn Leu Val Ile Ser Asp Ile Leu Phe Thr Thr Ala Leu Pro
1               5                   10                  15

Thr Arg Ile Ala Tyr Tyr Ala Met Gly Phe Asp Trp Arg Ile Gly Asp
            20                  25                  30

Ala Leu Cys Arg Ile Thr Ala
        35

<210> SEQ ID NO 308
<211> LENGTH: 38
<212> TYPE: PRT
<213> ORGANISM: Artificial Sequence
<220> FEATURE:
<223> OTHER INFORMATION: GCRTchick GPCR TM2

<400> SEQUENCE: 308

Met Leu Asn Leu Ala Ile Ser Asp Leu Leu Phe Val Phe Thr Leu Pro
1               5                   10                  15

Phe Arg Ile Tyr Tyr Phe Val Val Arg Asn Trp Pro Phe Gly Asp Val
            20                  25                  30

Leu Cys Lys Ile Ser Val
        35

<210> SEQ ID NO 309
<211> LENGTH: 41
<212> TYPE: PRT
<213> ORGANISM: Artificial Sequence
<220> FEATURE:
<223> OTHER INFORMATION: APJ GPCR TM2

<400> SEQUENCE: 309

Ile Phe Ile Ala Ser Leu Ala Val Ala Asp Leu Thr Phe Val Val Thr
1               5                   10                  15

Leu Pro Leu Trp Ala Thr Tyr Thr Tyr Arg Asp Tyr Asp Trp Pro Phe
            20                  25                  30

Gly Thr Phe Phe Cys Lys Leu Ser Ser
        35                  40

<210> SEQ ID NO 310
<211> LENGTH: 43
<212> TYPE: PRT
<213> ORGANISM: Artificial Sequence
<220> FEATURE:
<223> OTHER INFORMATION: RTArat GPCR TM2

<400> SEQUENCE: 310

Phe Ser Ile Tyr Phe Leu His Leu Ala Ser Ala Asp Gly Ile Tyr Leu
1               5                   10                  15

Phe Ser Lys Ala Val Ile Ala Leu Leu Asn Met Gly Thr Phe Leu Gly
            20                  25                  30

Ser Phe Pro Asp Tyr Val Arg Arg Val Ser Arg
        35                  40

<210> SEQ ID NO 311
<211> LENGTH: 44
<212> TYPE: PRT
<213> ORGANISM: Artificial Sequence
<220> FEATURE:
<223> OTHER INFORMATION: UHRrat GPCR TM2

<400> SEQUENCE: 311

Thr Asn Phe Leu Ile Gly Asn Leu Ala Leu Ser Asp Val Leu Met Cys
1               5                   10                  15

Ala Ala Cys Val Pro Leu Thr Leu Ala Tyr Ala Phe Glu Pro Arg Gly
            20                  25                  30

Trp Val Phe Gly Gly Leu Cys His Leu Val Phe
        35                  40

<210> SEQ ID NO 312
<211> LENGTH: 43
<212> TYPE: PRT
<213> ORGANISM: Artificial Sequence
<220> FEATURE:
<223> OTHER INFORMATION: FMRL1 GPCR TM2

<400> SEQUENCE: 312

Asn Thr Ile Cys Tyr Leu Asn Leu Ala Leu Ala Asp Phe Ser Phe Ser
1               5                   10                  15

Ala Ile Leu Pro Phe Arg Met Val Ser Val Ala Met Arg Glu Lys Trp
            20                  25                  30

Pro Phe Ala Ser Phe Leu Cys Lys Leu Val His
        35                  40

<210> SEQ ID NO 313
<211> LENGTH: 43
<212> TYPE: PRT
<213> ORGANISM: Artificial Sequence
<220> FEATURE:
<223> OTHER INFORMATION: FMRL2 GPCR TM2

<400> SEQUENCE: 313

Thr Thr Ile Cys Tyr Leu Asn Leu Ala Leu Ala Asp Phe Ser Phe Thr
1               5                   10                  15

Ala Thr Leu Pro Phe Leu Ile Val Ser Met Ala Met Gly Glu Lys Trp
            20                  25                  30

Pro Phe Gly Trp Phe Leu Cys Lys Leu Ile His
        35                  40

<210> SEQ ID NO 314
<211> LENGTH: 43
<212> TYPE: PRT
<213> ORGANISM: Artificial Sequence
<220> FEATURE:
<223> OTHER INFORMATION: fMLP GPCR TM2

<400> SEQUENCE: 314

Thr Thr Ile Ser Tyr Leu Asn Leu Ala Val Ala Asp Phe Cys Phe Thr
1               5                   10                  15

Ser Thr Leu Pro Phe Phe Met Val Arg Lys Ala Met Gly Gly His Trp
            20                  25                  30

Pro Phe Gly Trp Phe Leu Cys Lys Phe Leu Phe
        35                  40

<210> SEQ ID NO 315
<211> LENGTH: 43
<212> TYPE: PRT
<213> ORGANISM: Artificial Sequence
<220> FEATURE:
<223> OTHER INFORMATION: OLF1catfish GPCR TM2

<400> SEQUENCE: 315

Lys Tyr Ile Thr Val Phe Asn Leu Ala Leu Ser Asp Leu Gly Gly Ser
1               5                   10                  15

Ser Ala Leu Ile Pro Lys Leu Ile Asp Thr Phe Leu Phe Glu Asn Gln
            20                  25                  30

Val Ile Ser Tyr Glu Ala Cys Leu Ala Asn Met
        35                  40

<210> SEQ ID NO 316
<211> LENGTH: 43
<212> TYPE: PRT
<213> ORGANISM: Artificial Sequence
<220> FEATURE:
<223> OTHER INFORMATION: OLF3catfish GPCR TM2

<400> SEQUENCE: 316

Lys Tyr Ile Ala Val Phe Asn Leu Ala Leu Ser Asp Leu Cys Gly Ser
1               5                   10                  15

Ser Ala Leu Ile Pro Lys Leu Leu Asp Met Leu Leu Phe Glu Asn Gln
            20                  25                  30

Ser Ile Ser Tyr Glu Ala Cys Leu Ser Asn Met
        35                  40

<210> SEQ ID NO 317
<211> LENGTH: 43
<212> TYPE: PRT
<213> ORGANISM: Artificial Sequence
<220> FEATURE:
<223> OTHER INFORMATION: OLF8catfish GPCR TM2

<400> SEQUENCE: 317

Met Cys Ile Leu Ile Gly Leu Met Ala Val Val Asp Leu Ser Met Pro
1               5                   10                  15

Ile Phe Cys Val Pro Asn Met Leu Leu Ser Phe Leu Phe Asn Trp Lys
            20                  25                  30

Gly Ile Ser Leu Val Gly Cys Leu Val Gln Met
        35                  40

<210> SEQ ID NO 318
<211> LENGTH: 43
<212> TYPE: PRT
<213> ORGANISM: Artificial Sequence
<220> FEATURE:
<223> OTHER INFORMATION: OLF32Acatfish GPCR TM2

<400> SEQUENCE: 318

Lys Tyr Met Gly Ile Phe Asn Leu Ala Leu Ser Asp Phe Gly Glu Thr
1               5                   10                  15

Asn Val Leu Ile Pro Ser Leu Val Lys Thr Leu Phe Phe Asp Ser Gln
            20                  25                  30

Tyr Ile Ser Tyr Asp Ala Cys Leu Ala Asn Met
        35                  40

<210> SEQ ID NO 319
<211> LENGTH: 43
<212> TYPE: PRT
<213> ORGANISM: Artificial Sequence
<220> FEATURE:
<223> OTHER INFORMATION: OLF32Bcatfish and OLF32Dcatfish GPCR TM2

<400> SEQUENCE: 319

Lys Tyr Met Gly Ile Phe Asn Leu Ala Leu Ser Asp Phe Gly Glu Thr
1               5                   10                  15

Asn Ala Leu Ile Pro Ser Leu Val Lys Thr Leu Phe Phe Asp Ser Gln
            20                  25                  30

Tyr Ile Ser Tyr Asp Ala Cys Leu Ala Asn Met
        35                  40

<210> SEQ ID NO 320
<211> LENGTH: 43
<212> TYPE: PRT
<213> ORGANISM: Artificial Sequence
<220> FEATURE:
<223> OTHER INFORMATION: OLF32Ccatfish GPCR TM2

<400> SEQUENCE: 320

Lys Tyr Met Gly Ile Phe Asn Leu Ala Leu Ser Asp Ile Gly Glu Thr
1               5                   10                  15

Asn Ala Leu Ile Pro Ser Leu Val Lys Thr Leu Phe Phe Asp Ser Gln
            20                  25                  30

Tyr Ile Ser Tyr Asp Ala Cys Leu Thr Asn Met
        35                  40

<210> SEQ ID NO 321
<211> LENGTH: 43
<212> TYPE: PRT
<213> ORGANISM: Artificial Sequence
<220> FEATURE:
<223> OTHER INFORMATION: OLF47catfish GPCR TM2

<400> SEQUENCE: 321

Lys Phe Leu Ala Val Phe Asn Leu Ala Val Val Asp Ile Ser Ile Asn
1               5                   10                  15

Ser Val Ile Ile Pro Gln Met Val Pro Val Phe Val Phe Asn Leu Asn
            20                  25                  30

His Ile Ser Phe Glu Ser Cys Phe Ser Gln Met
        35                  40

-continued

<210> SEQ ID NO 322
<211> LENGTH: 43
<212> TYPE: PRT
<213> ORGANISM: Artificial Sequence
<220> FEATURE:
<223> OTHER INFORMATION: OLF202catfish GPCR TM2

<400> SEQUENCE: 322

Met Tyr Tyr Ile Met Leu Asn Leu Ala Ala Ser Asp Val Leu Phe Ser
1               5                   10                  15

Thr Thr Thr Leu Pro Lys Ile Ile Ala Arg Tyr Trp Phe Gly Asp Gly
            20                  25                  30

Ser Ile Ser Phe Val Gly Cys Phe Ile Gln Met
        35                  40

<210> SEQ ID NO 323
<211> LENGTH: 43
<212> TYPE: PRT
<213> ORGANISM: Artificial Sequence
<220> FEATURE:
<223> OTHER INFORMATION: OLFCOR1chicken, OLFCOR3chicken AND
      OLFCOR4chicken GPCR TM2

<400> SEQUENCE: 323

Met Tyr Ile Phe Leu Gln Asn Leu Ser Phe Thr Asp Ala Ala Tyr Ser
1               5                   10                  15

Thr Val Ile Thr Pro Lys Met Leu Ala Thr Phe Leu Glu Glu Arg Lys
            20                  25                  30

Thr Ile Ser Tyr Val Gly Cys Ile Leu Gln Tyr
        35                  40

<210> SEQ ID NO 324
<211> LENGTH: 43
<212> TYPE: PRT
<213> ORGANISM: Artificial Sequence
<220> FEATURE:
<223> OTHER INFORMATION: OLFCOR2chicken and OLFCOR5chicken GPCR TM2

<400> SEQUENCE: 324

Met Tyr Ile Phe Leu Gln Asn Leu Ser Phe Thr Asp Ala Ala Tyr Ser
1               5                   10                  15

Thr Val Ile Thr Pro Lys Met Leu Ala Thr Phe Leu Glu Glu Arg Arg
            20                  25                  30

Thr Ile Ser Tyr Val Gly Cys Ile Leu Gln Tyr
        35                  40

<210> SEQ ID NO 325
<211> LENGTH: 43
<212> TYPE: PRT
<213> ORGANISM: Artificial Sequence
<220> FEATURE:
<223> OTHER INFORMATION: OLFCOR6chicken GPCR TM2

<400> SEQUENCE: 325

Met Tyr Ile Phe Leu Gln Asn Leu Ser Phe Thr Asp Ala Val Tyr Ser
1               5                   10                  15

Thr Val Ile Thr Pro Lys Met Leu Ala Thr Phe Leu Glu Glu Thr Lys
            20                  25                  30

Thr Ile Ser Tyr Val Gly Cys Ile Leu Gln Tyr
        35                  40

<210> SEQ ID NO 326
<211> LENGTH: 43
<212> TYPE: PRT
<213> ORGANISM: Artificial Sequence
<220> FEATURE:
<223> OTHER INFORMATION: OLFdog GPCR TM2

<400> SEQUENCE: 326

Met Tyr Leu Phe Leu Ser Asn Leu Ser Phe Ser Asp Leu Cys Phe Ser
1               5                   10                  15

Ser Val Thr Met Pro Lys Leu Leu Gln Asn Met Gln Ser Gln Val Pro
            20                  25                  30

Ser Ile Pro Tyr Ala Gly Cys Leu Thr Gln Met
        35                  40

<210> SEQ ID NO 327
<211> LENGTH: 43
<212> TYPE: PRT
<213> ORGANISM: Artificial Sequence
<220> FEATURE:
<223> OTHER INFORMATION: OLF07E GPCR TM2

<400> SEQUENCE: 327

Val Tyr Phe Phe Leu Ala Asn Leu Ser Phe Thr Asp Leu Phe Phe Val
1               5                   10                  15

Thr Asn Thr Ile Pro Lys Met Leu Val Asn Leu Gln Ser His Asn Lys
            20                  25                  30

Ala Ile Ser Tyr Ala Gly Cys Leu Thr Gln Leu
        35                  40

<210> SEQ ID NO 328
<211> LENGTH: 43
<212> TYPE: PRT
<213> ORGANISM: Artificial Sequence
<220> FEATURE:
<223> OTHER INFORMATION: OLF07I GPCR TM2

<400> SEQUENCE: 328

Met Tyr Leu Phe Leu Ser Asn Leu Ser Phe Ser Asp Leu Cys Phe Ser
1               5                   10                  15

Ser Val Thr Ile Pro Lys Leu Leu Gln Asn Met Gln Asn Gln Asp Pro
            20                  25                  30

Ser Ile Pro Tyr Ala Asp Cys Leu Thr Gln Met
        35                  40

<210> SEQ ID NO 329
<211> LENGTH: 43
<212> TYPE: PRT
<213> ORGANISM: Artificial Sequence
<220> FEATURE:
<223> OTHER INFORMATION: OLF07J GPCR TM2

<400> SEQUENCE: 329

Met Tyr Phe Phe Leu Ser Met Leu Ser Thr Ser Glu Thr Val Tyr Thr
1               5                   10                  15

Leu Val Ile Leu Pro Arg Met Leu Ser Ser Leu Val Gly Met Ser Gln
            20                  25                  30

Pro Met Ser Leu Ala Gly Cys Ala Thr Gln Met
        35                  40

```
<210> SEQ ID NO 330
<211> LENGTH: 43
<212> TYPE: PRT
<213> ORGANISM: Artificial Sequence
<220> FEATURE:
<223> OTHER INFORMATION: OLFOR3mouse GPCR TM2

<400> SEQUENCE: 330

Met Tyr Phe Phe Leu Ser Asn Leu Ser Ser Leu Asp Leu Ala Phe Thr
 1               5                  10                  15

Thr Ser Ser Val Pro Gln Met Leu Lys Asn Leu Trp Gly Pro Asp Lys
            20                  25                  30

Thr Ile Ser Tyr Gly Gly Cys Val Thr Gln Leu
        35                  40

<210> SEQ ID NO 331
<211> LENGTH: 43
<212> TYPE: PRT
<213> ORGANISM: Artificial Sequence
<220> FEATURE:
<223> OTHER INFORMATION: OLFrat GPCR TM2

<400> SEQUENCE: 331

Met Tyr Tyr Phe Leu Ser Ser Leu Ser Phe Val Asp Leu Cys Tyr Ser
 1               5                  10                  15

Thr Val Ile Thr Pro Lys Met Leu Val Asn Phe Leu Gly Lys Lys Asn
            20                  25                  30

Phe Ile Thr Tyr Ser Glu Cys Met Ala Gln Phe
        35                  40

<210> SEQ ID NO 332
<211> LENGTH: 43
<212> TYPE: PRT
<213> ORGANISM: Artificial Sequence
<220> FEATURE:
<223> OTHER INFORMATION: OLFF3rat GPCR TM2

<400> SEQUENCE: 332

Met Tyr Phe Phe Leu Ser Asn Leu Ser Phe Val Asp Ile Cys Phe Ile
 1               5                  10                  15

Ser Thr Thr Val Pro Lys Met Leu Val Asn Ile Gln Thr Gln Asn Asn
            20                  25                  30

Val Ile Thr Tyr Ala Gly Cys Ile Thr Gln Ile
        35                  40

<210> SEQ ID NO 333
<211> LENGTH: 43
<212> TYPE: PRT
<213> ORGANISM: Artificial Sequence
<220> FEATURE:
<223> OTHER INFORMATION: OLFF5rat GPCR TM2

<400> SEQUENCE: 333

Met Tyr Phe Phe Leu Ser Asn Leu Ser Phe Val Asp Val Cys Phe Ser
 1               5                  10                  15

Ser Thr Thr Val Pro Lys Val Leu Ala Asn His Ile Leu Gly Ser Gln
            20                  25                  30

Ala Ile Ser Phe Ser Gly Cys Leu Thr Gln Leu
        35                  40
```

```
<210> SEQ ID NO 334
<211> LENGTH: 43
<212> TYPE: PRT
<213> ORGANISM: Artificial Sequence
<220> FEATURE:
<223> OTHER INFORMATION: OLFF6rat GPCR TM2

<400> SEQUENCE: 334
```

Met Tyr Phe Phe Leu Cys Asn Leu Ser Phe Leu Glu Ile Trp Phe Thr
 1               5                  10                  15

Thr Ala Cys Val Pro Lys Thr Leu Ala Thr Phe Ala Pro Arg Gly Gly
            20                  25                  30

Val Ile Ser Leu Ala Gly Cys Ala Thr Gln Met
        35                  40

```
<210> SEQ ID NO 335
<211> LENGTH: 43
<212> TYPE: PRT
<213> ORGANISM: Artificial Sequence
<220> FEATURE:
<223> OTHER INFORMATION: OLFF12rat GPCR TM2

<400> SEQUENCE: 335
```

Met Tyr Phe Phe Leu Ala Asn Leu Ser Phe Val Asp Ile Cys Phe Thr
 1               5                  10                  15

Ser Thr Thr Ile Pro Lys Met Leu Val Asn Ile Tyr Thr Gln Ser Lys
            20                  25                  30

Ser Ile Thr Tyr Glu Asp Cys Ile Ser Gln Met
        35                  40

```
<210> SEQ ID NO 336
<211> LENGTH: 43
<212> TYPE: PRT
<213> ORGANISM: Artificial Sequence
<220> FEATURE:
<223> OTHER INFORMATION: OLFI3rat GPCR TM2

<400> SEQUENCE: 336
```

Met Tyr Leu Phe Leu Ser Asn Leu Ser Phe Ser Asp Leu Cys Phe Ser
 1               5                  10                  15

Ser Val Thr Met Pro Lys Leu Leu Gln Asn Met Arg Ser Gln Asp Thr
            20                  25                  30

Ser Ile Pro Tyr Gly Gly Cys Leu Ala Gln Thr
        35                  40

```
<210> SEQ ID NO 337
<211> LENGTH: 47
<212> TYPE: PRT
<213> ORGANISM: Artificial Sequence
<220> FEATURE:
<223> OTHER INFORMATION: OLFI7rat GPCR TM2

<400> SEQUENCE: 337
```

Met Tyr Phe Phe Leu Ala Asn Met Ser Phe Leu Glu Ile Trp Tyr Val
 1               5                  10                  15

Thr Val Thr Ile Pro Lys Met Leu Ala Gly Phe Ile Gly Ser Lys Glu
            20                  25                  30

Asn His Gly Gln Leu Ile Ser Phe Glu Ala Cys Met Thr Gln Leu
        35                  40                  45

```
<210> SEQ ID NO 338
<211> LENGTH: 43
<212> TYPE: PRT
<213> ORGANISM: Artificial Sequence
<220> FEATURE:
<223> OTHER INFORMATION: OLFI8rat GPCR TM2

<400> SEQUENCE: 338

Met Tyr Leu Phe Leu Ser Asn Leu Ser Phe Ser Asp Leu Cys Phe Ser
 1               5                  10                  15

Ser Val Thr Met Leu Lys Leu Leu Gln Asn Ile Gln Ser Gln Val Pro
            20                  25                  30

Ser Ile Ser Tyr Ala Gly Cys Leu Thr Gln Ile
        35                  40

<210> SEQ ID NO 339
<211> LENGTH: 43
<212> TYPE: PRT
<213> ORGANISM: Artificial Sequence
<220> FEATURE:
<223> OTHER INFORMATION: OLFI9rat GPCR TM2

<400> SEQUENCE: 339

Met Tyr Leu Phe Leu Ser Asn Leu Ser Phe Ala Asp Leu Cys Phe Ser
 1               5                  10                  15

Ser Val Thr Met Pro Lys Leu Leu Gln Asn Met Gln Ser Gln Val Pro
            20                  25                  30

Ser Ile Pro Tyr Ala Gly Cys Leu Ala Gln Ile
        35                  40

<210> SEQ ID NO 340
<211> LENGTH: 43
<212> TYPE: PRT
<213> ORGANISM: Artificial Sequence
<220> FEATURE:
<223> OTHER INFORMATION: OLFI14rat GPCR TM2

<400> SEQUENCE: 340

Met Tyr Leu Phe Leu Ser Asn Leu Ser Phe Ser Asp Leu Cys Phe Ser
 1               5                  10                  15

Ser Val Thr Met Pro Lys Leu Leu Gln Asn Met Gln Ser Gln Val Pro
            20                  25                  30

Ser Ile Ser Tyr Thr Gly Cys Leu Thr Gln Leu
        35                  40

<210> SEQ ID NO 341
<211> LENGTH: 43
<212> TYPE: PRT
<213> ORGANISM: Artificial Sequence
<220> FEATURE:
<223> OTHER INFORMATION: OLFI15rat GPCR TM2

<400> SEQUENCE: 341

Met Tyr Leu Phe Leu Ser Asn Leu Ser Phe Ser Asp Leu Cys Phe Ser
 1               5                  10                  15

Ser Val Thr Met Pro Lys Leu Leu Gln Asn Met Gln Ser Gln Val Pro
            20                  25                  30

Ser Ile Pro Phe Ala Gly Cys Leu Thr Gln Leu
        35                  40
```

<210> SEQ ID NO 342
<211> LENGTH: 43
<212> TYPE: PRT
<213> ORGANISM: Artificial Sequence
<220> FEATURE:
<223> OTHER INFORMATION: OLFOR17_40 GPCR TM2

<400> SEQUENCE: 342

Met Tyr Phe Phe Leu Gly Asn Leu Ser Val Leu Asp Val Gly Cys Ile
1               5                   10                  15

Ser Val Thr Val Pro Ser Met Leu Ser Arg Leu Leu Ser Arg Lys Arg
            20                  25                  30

Ala Val Pro Cys Gly Ala Cys Leu Thr Gln Leu
        35                  40

<210> SEQ ID NO 343
<211> LENGTH: 43
<212> TYPE: PRT
<213> ORGANISM: Artificial Sequence
<220> FEATURE:
<223> OTHER INFORMATION: GUST27rat GPCR TM2

<400> SEQUENCE: 343

Met Tyr Phe Phe Leu Ser Asn Leu Ser Phe Val Asp Ile Cys Phe Ile
1               5                   10                  15

Ser Thr Thr Ile Pro Lys Met Leu Val Asn Ile His Ser Gln Thr Lys
            20                  25                  30

Asp Ile Ser Tyr Ile Glu Cys Leu Ser Gln Val
        35                  40

<210> SEQ ID NO 344
<211> LENGTH: 42
<212> TYPE: PRT
<213> ORGANISM: Artificial Sequence
<220> FEATURE:
<223> OTHER INFORMATION: RPE GPCR TM2

<400> SEQUENCE: 344

Cys His Leu Leu Val Leu Ser Leu Ala Leu Ala Asp Ser Gly Ile Ser
1               5                   10                  15

Leu Asn Ala Leu Val Ala Ala Thr Ser Ser Leu Leu Arg Arg Trp Pro
            20                  25                  30

Tyr Gly Ser Asp Gly Cys Gln Ala His Gly
        35                  40

<210> SEQ ID NO 345
<211> LENGTH: 41
<212> TYPE: PRT
<213> ORGANISM: Artificial Sequence
<220> FEATURE:
<223> OTHER INFORMATION: HHRF1 GPCR TM2

<400> SEQUENCE: 345

Gly Asp Val Tyr Phe Ile Asn Leu Ala Ala Ala Asp Leu Leu Phe Val
1               5                   10                  15

Cys Thr Leu Pro Leu Trp Met Gln Tyr Leu Leu Asp His Asn Ser Leu
            20                  25                  30

Ala Ser Val Pro Cys Thr Leu Leu Thr
        35                  40

```
<210> SEQ ID NO 346
<211> LENGTH: 42
<212> TYPE: PRT
<213> ORGANISM: Artificial Sequence
<220> FEATURE:
<223> OTHER INFORMATION: HHRF2 GPCR TM2

<400> SEQUENCE: 346

Ser Asp Thr Tyr Ile Cys Asn Leu Ala Val Ala Asp Leu Leu Ile Val
1               5                   10                  15

Val Gly Leu Pro Phe Phe Leu Glu Tyr Ala Lys His His Pro Lys Leu
            20                  25                  30

Ser Arg Glu Val Val Cys Ser Gly Leu Asn
        35                  40

<210> SEQ ID NO 347
<211> LENGTH: 41
<212> TYPE: PRT
<213> ORGANISM: Artificial Sequence
<220> FEATURE:
<223> OTHER INFORMATION: HHRF3 GPCR TM2

<400> SEQUENCE: 347

Pro Thr Ile Tyr Met Thr Asn Leu Tyr Ser Thr Asn Phe Leu Thr Leu
1               5                   10                  15

Thr Val Leu Pro Phe Ile Val Leu Ser Asn Gln Trp Leu Leu Pro Ala
            20                  25                  30

Gly Val Ala Ser Cys Lys Phe Leu Ser
        35                  40

<210> SEQ ID NO 348
<211> LENGTH: 41
<212> TYPE: PRT
<213> ORGANISM: Artificial Sequence
<220> FEATURE:
<223> OTHER INFORMATION: MCP-1A and MCP-1B GPCR TM2

<400> SEQUENCE: 348

Thr Asp Ile Tyr Leu Leu Asn Leu Ala Ile Ser Asp Leu Leu Phe Leu
1               5                   10                  15

Ile Thr Leu Pro Leu Trp Ala His Ser Ala Ala Asn Glu Trp Val Phe
            20                  25                  30

Gly Asn Ala Met Cys Lys Leu Phe Thr
        35                  40

<210> SEQ ID NO 349
<211> LENGTH: 41
<212> TYPE: PRT
<213> ORGANISM: Artificial Sequence
<220> FEATURE:
<223> OTHER INFORMATION: PPR1bovine GPCR TM2

<400> SEQUENCE: 349

Thr Asp Val Tyr Ile Leu Asn Leu Ala Val Ala Asp Leu Phe Leu Leu
1               5                   10                  15

Phe Thr Leu Pro Phe Trp Ala Val Asn Ala Val His Gly Trp Val Leu
            20                  25                  30

Gly Lys Ile Met Cys Lys Val Thr Ser
        35                  40
```

```
<210> SEQ ID NO 350
<211> LENGTH: 18
<212> TYPE: PRT
<213> ORGANISM: Artificial Sequence
<220> FEATURE:
<223> OTHER INFORMATION: F-1-5 GPCR CXCR4
<221> NAME/KEY: MOD_RES
<222> LOCATION: (18)...(18)
<223> OTHER INFORMATION: Xaa = valinamide

<400> SEQUENCE: 350

Asp Asp Ile Phe Leu Pro Thr Ile Tyr Ser Ile Ile Phe Leu Thr Gly
 1               5                   10                  15

Ile Xaa

<210> SEQ ID NO 351
<211> LENGTH: 22
<212> TYPE: PRT
<213> ORGANISM: Artificial Sequence
<220> FEATURE:
<223> OTHER INFORMATION: F-2-1 GPCR CXCR4

<400> SEQUENCE: 351

Leu Leu Phe Val Ile Thr Leu Pro Phe Trp Ala Val Asp Ala Val Ala
 1               5                   10                  15

Asn Trp Tyr Phe Gly Asn
             20

<210> SEQ ID NO 352
<211> LENGTH: 23
<212> TYPE: PRT
<213> ORGANISM: Artificial Sequence
<220> FEATURE:
<223> OTHER INFORMATION: F-3-1 GPCR CXCR4
<221> NAME/KEY: MOD_RES
<222> LOCATION: (23)...(23)
<223> OTHER INFORMATION: Xaa = leucinamide

<400> SEQUENCE: 352

Lys Ala Val His Val Ile Tyr Thr Val Asn Leu Tyr Ser Ser Val Leu
 1               5                   10                  15

Ile Leu Ala Phe Ile Ser Xaa
             20

<210> SEQ ID NO 353
<211> LENGTH: 20
<212> TYPE: PRT
<213> ORGANISM: Artificial Sequence
<220> FEATURE:
<223> OTHER INFORMATION: F-4-1 GPCR CXCR4

<400> SEQUENCE: 353

Lys Val Tyr Val Gly Val Trp Ile Pro Ala Leu Leu Leu Thr Ile Pro
 1               5                   10                  15

Asp Phe Ile Phe
             20

<210> SEQ ID NO 354
<211> LENGTH: 21
<212> TYPE: PRT
<213> ORGANISM: Artificial Sequence
<220> FEATURE:
<223> OTHER INFORMATION: F-5-1 GPCR CXCR4
<221> NAME/KEY: MOD_RES
<222> LOCATION: (21)...(21)
<223> OTHER INFORMATION: Xaa = isoleucinamide
```

```
<400> SEQUENCE: 354

His Ile Met Val Gly Leu Ile Leu Pro Gly Ile Val Ile Leu Ser Cys
1               5                   10                  15

Tyr Cys Ile Ile Xaa
            20

<210> SEQ ID NO 355
<211> LENGTH: 20
<212> TYPE: PRT
<213> ORGANISM: Artificial Sequence
<220> FEATURE:
<223> OTHER INFORMATION: F-7-1 GPCR CXCR4
<221> NAME/KEY: MOD_RES
<222> LOCATION: (20)...(20)
<223> OTHER INFORMATION: Xaa = lysinamide

<400> SEQUENCE: 355

Ala Leu Ala Phe Phe His Cys Cys Leu Asn Pro Ile Leu Tyr Ala Phe
1               5                   10                  15

Leu Gly Ala Xaa
            20

<210> SEQ ID NO 356
<211> LENGTH: 32
<212> TYPE: PRT
<213> ORGANISM: Artificial Sequence
<220> FEATURE:
<223> OTHER INFORMATION: second transmembrane domain of CXCR4

<400> SEQUENCE: 356

His Leu Ser Val Ala Asp Leu Leu Phe Val Ile Thr Leu Pro Phe Trp
1               5                   10                  15

Ala Val Asp Ala Val Ala Asn Trp Tyr Phe Gly Asn Phe Leu Cys Lys
            20                  25                  30

<210> SEQ ID NO 357
<211> LENGTH: 24
<212> TYPE: PRT
<213> ORGANISM: Artificial Sequence
<220> FEATURE:
<223> OTHER INFORMATION: F-2-8 GPCR CXCR4

<400> SEQUENCE: 357

Leu Leu Phe Val Ile Thr Leu Pro Phe Trp Ala Val Asp Ala Val Ala
1               5                   10                  15

Asn Trp Tyr Phe Gly Asn Lys Lys
            20

<210> SEQ ID NO 358
<211> LENGTH: 21
<212> TYPE: PRT
<213> ORGANISM: Artificial Sequence
<220> FEATURE:
<223> OTHER INFORMATION: F-2-4 GPCR CXCR4

<400> SEQUENCE: 358

Val Ile Thr Leu Pro Phe Trp Ala Val Asp Ala Val Ala Asn Trp Tyr
1               5                   10                  15

Phe Gly Asn Lys Lys
            20
```

-continued

```
<210> SEQ ID NO 359
<211> LENGTH: 19
<212> TYPE: PRT
<213> ORGANISM: Artificial Sequence
<220> FEATURE:
<223> OTHER INFORMATION: AcF-2-5 GPCR CXCR4
<221> NAME/KEY: MOD_RES
<222> LOCATION: (1)...(1)
<223> OTHER INFORMATION: Xaa = acetylated Leu

<400> SEQUENCE: 359

Xaa Leu Phe Val Ile Thr Leu Pro Phe Trp Ala Val Asp Ala Val Ala
 1               5                  10                  15

Asn Asp Asp

<210> SEQ ID NO 360
<211> LENGTH: 24
<212> TYPE: PRT
<213> ORGANISM: Artificial Sequence
<220> FEATURE:
<223> OTHER INFORMATION: F-2-6 GPCR CXCR4

<400> SEQUENCE: 360

Leu Ser Val Ala Asp Leu Leu Phe Val Ile Thr Leu Pro Phe Trp Ala
 1               5                  10                  15

Val Asp Ala Val Ala Asn Asp Asp
            20

<210> SEQ ID NO 361
<211> LENGTH: 27
<212> TYPE: PRT
<213> ORGANISM: Artificial Sequence
<220> FEATURE:
<223> OTHER INFORMATION: Rhod-AcF-2-2 GPCR CXCR4
<221> NAME/KEY: MOD_RES
<222> LOCATION: (1)...(1)
<223> OTHER INFORMATION: Xaa = acetylated Leu
<221> NAME/KEY: MOD_RES
<222> LOCATION: (26)...(26)
<223> OTHER INFORMATION: Xaa = rhodamine linked to Lys

<400> SEQUENCE: 361

Xaa Leu Leu Phe Val Ile Thr Leu Pro Phe Trp Ala Val Asp Ala Val
 1               5                  10                  15

Ala Asn Trp Tyr Phe Gly Asn Asp Asp Xaa Asp
            20                  25

<210> SEQ ID NO 362
<211> LENGTH: 28
<212> TYPE: PRT
<213> ORGANISM: Artificial Sequence
<220> FEATURE:
<223> OTHER INFORMATION: CCKAR-TM-4-2 (#71) GPCR CCKAR

<400> SEQUENCE: 362

Val Ile Ala Ala Thr Trp Cys Leu Ser Phe Thr Ile Met Thr Pro Tyr
 1               5                  10                  15

Pro Ile Tyr Ser Asn Leu Val Pro Phe Thr Asp Asp
            20                  25

<210> SEQ ID NO 363
<211> LENGTH: 24
<212> TYPE: PRT
<213> ORGANISM: Artificial Sequence
<220> FEATURE:
<223> OTHER INFORMATION: CCKAR-TM-5-3 (#45) GPCR CCKAR
```

```
<400> SEQUENCE: 363

Asp Asp Gln Thr Phe Leu Leu Leu Ile Leu Phe Leu Leu Pro Gly Ile
1               5                   10                  15

Val Met Val Val Ala Tyr Gly Leu
            20
```

G PROTEIN-COUPLED RECEPTOR ANTAGONISTS

CROSS-REFERENCE TO RELATED APPLICATIONS

This application claims the benefit of U.S. Provisional Application No. 60/076,105 filed Feb. 27, 1998, the disclosure of which is incorporated by reference.

FIELD OF THE INVENTION

The present invention relates to modulating, especially inhibiting, biological activities of G protein coupled receptors (GPCRs) by exposing GPCRs to molecules which interfere with correct receptor assembly. In particular, the invention relates to synthetic, isolated and/or recombinant peptides, fragments and/or consensus peptides of the transmembrane domain of GPCRs that inhibit GPCR-mediated signal transduction.

BACKGROUND OF THE INVENTION

Many physiologically important events are mediated by the binding of guanine nucleotide-binding regulatory proteins (G proteins) to G protein-coupled receptors (GPCRs). These events include vasodilation, stimulation or decrease in heart rate, bronchodilation, stimulation of endocrine secretions and enhancement of gut peristalsis, development, mitogenesis, cell proliferation and oncogenesis.

G proteins are a diverse superfamily of guanine nucleotide-binding proteins that play a central role in signal transduction and regulation of cellular metabolism. They are generally comprised of three subunits: a guanyl-nucleotide binding alpha subunit; a beta subunit; and a gamma subunit. (For a review, see Conklin et al. *Cell* 73, 631–641, (1993)). G proteins commonly cycle between two forms, depending on whether GDP or GTP is bound to the alpha subunit. When GDP is bound, the G protein exists as a heterotrimer, the G alpha-beta-gamma complex. When an alpha-beta-gamma complex operatively associates with a ligand-activated GPCR in a cell membrane, the rate of exchange of GTP for bound GDP is increased and the G alpha subunit dissociates from the G beta-gamma complex. The free G alpha subunit and G beta-gamma complex are capable of transmitting a signal to downstream elements of a variety of signal transduction pathways, for example by binding to and activating adenyl cyclase. This fundamental scheme of events forms the basis for a multiplicity of different cell signaling phenomena.

Recent studies have suggested that all members of the GPCR superfamily have a conserved structure. Comparisons of avian and mammalian beta-adrenergic receptor cDNA's (Yarden et al., *Proc. Natl. Acad. Sci. USA* 83: 6795–6799, 1986; Dixon et al., *Nature* 321:75–79, 1986; and Kobilka et al., *Proc. Natl. Acad. Sci. USA* 84:46–50, 1987), a bovine rhodopsin cDNA (Nathans and Hogness, *Cell* 34:807–814, 1983), an alpha 2-adrenergic receptor (Kobilka et al., *Science* 238:650–656, 1987), an angiotensin receptor cDNA (Young et al., *Cell* 45:711–719, 1986; Jackson et al., *Nature* 335:437439, 1988), a bovine substance K receptor (Masu et al., *Nature* 329:836–838, 1987), and a muscarinic acetylcholine receptor cDNA (Kubo et al., *Nature* 323:411416, 1986) predict that all GPCR share a highly conserved presence of seven hydrophobic transmembrane domains that are suggested to be transmembrane helices of 20–30 amino acids connected by extracellular or cytoplasmic loops. Kobilka et al., *Science* 240: 1310 (1988); Maggio et al., *FEBS Lett.* 319: 195 (1993); Maggio et al., *Proc. Natl. Acad. Sci USA* 90: 3103 (1993); Ridge et al., *Proc. Natl. Sci USA* 91, 3204 (1995); Schonenberg et al., *J. Biol. Chem.* 270: 18000 (1995); Huang et al., *J. Biol. Chem.* 256: 3802 (1981); Popot et al., *J. Mol. Biol.* 198: 655 (1987); Kahn and Engelman, *Biochemistry* 31: 6144 (1992); Schoneberg et al. *EMBO J.* 15: 1283 (1996); Wong et al., *J. Biol. Chem.* 265: 6219 (1990); Monnot et al., *J. Biol. Chem.* 271: 1507 (1996); Gudermann et al., *Annu. Rev. Neurosci.* 20: 399 (1997); Osuga et al., *J. Biol. Chem.* 272: 25006 (1997); Lefkowitz et al., *J. Biol. Chem.* 263:4993–4996, 1988; Panayotou and Waterfield, *Curr. Opinion Cell Biol.* 1:167–176, 1989. These transmembrane domains of G-protein coupled receptors are designated TM1, TM2, TM3, TM4, TMS, TM6 and TM7. TM4, TM5, TM6 and TM7 are the most highly conserved and are postulated to provide sequences which impart biological activity to GPCRs. TM3 is also implicated in signal transduction.

The coupling of GPCRs to intracellular signaling molecules such as adenylate cyclase (Anand-Srivastava et al., *J. Biol. Chem.* 271: 19324–19329 (1996)) and G-proteins (Merkouris et al., *Mol. Pharmacol.* 50: 985–993 (1996)) is reportedly inhibited by peptides corresponding to the intracellular loops of the receptors. Those studies were conducted primarily to provide an understanding of molecular mechanisms of receptor function and could not be applied directly for drug design, because of the difficulties in intracellular delivery of the inhibitors.

WO 94/05695 and U.S. Pat. No. 5,508,384 set forth sequences of transmembrane regions for 74 GPCRs. The WO 94/05695 patent publication describes and claims polypeptides corresponding to fragments or homologous sequences of GPCRs which can bind a GPCR ligand or which can modulate ligand binding. Both references disclose that a membrane spanning fragment of the third TM domain of the dopamine $D_2$ receptor specifically bound a ligand of the intact receptor in a simple, small unilamellar vesicle model. The fragment used was terminated with a lysine (which is positively charged at physiological pH) at one end and with an aspartic acid (which is negatively charged at physiological pH) at the other. This peptide would not be expected to insert readily into a biological membrane.

SUMMARY OF THE INVENTION

The invention generally comprises peptide or peptidomimetic compounds that modulate, and preferably inhibit the biological properties and activities of GPCRs, by targeting the transmembrane portions of these receptors. The present invention specifically comprises methods for disrupting GPCR function by using these GPCR antagonists.

The present invention provides for the use of chemical or recombinant DNA technology to obtain GPCR polypeptides, which preferably are as small as possible while still retaining sufficiently high affinity for binding to, or association with, GPCRs. Non-limiting examples of GPCR polypeptides include fragments of 10 to 50 amino acids corresponding to at least one transmembrane domain of domains 1–7. The following are nonlimiting examples of GPCR peptides with antagonist properties.

```
From the GPCR CXCR4
F-2-2:  LLFVITLPFWAVDAVANWYFGNDD        (SEQ ID NO:1)

F-2-5:  LLFVITLPFWAVDAVANDD             (SEQ ID NO:2)

F-4-2:  VYVGVWIPALLLTIPDFIFANDD         (SEQ ID NO:3)

F-6-1:  VILILAFFACWLPYYIGISID           (SEQ ID NO:4)

F-7-3:  DDEALAFFHCCLNPILYAFL-NH2        (SEQ ID NO:5)

F-7-4:  DDSITEALAFFHCCLNPILYAFL-NH2     (SEQ ID NO:6)

From the GPCR CCR5
CCR5-TM-2-2:  LFFL LTVPFWAHYAAAQWDFGDD      (SEQ ID NO:7)

CCR5-TM-4-1:  FGVVTSVITWVVAVFASLPGIIFTSSDD  (SEQ ID NO:8)

CCR5-TM-6-1:  LIFTIMIVYFLFWAPYNIVLLLNTFQED  (SEQ ID NO:9)

CCR5-TM-7-1:  DDQAMQVTETLGMTHCCINPIIYAFV    (SEQ ID NO:10)

From the GPCR CCR2
CCR2-TM-2-1:  IYLLNLAISDLLFLITLPLWADD       (SEQ ID NO:11)

CCR2-TM-2-2:  LLFLITLPLWAH SAANEWVFGNDD     (SEQ ID NO:12)

CCR2-TM-4-1:  FGVVTSVITWLVAVF ASVPGIIFTDD   (SEQ ID NO:13)

CCR2-TM-6-1:  VIFTIMIVYFLFWTPYN IVILLNTFQED (SEQ ID NO:14)

CCR2-TM-7-1:  DDATQVT ETLGMTHCCINPIIYAFV    (SEQ ID NO:15)

From the GPCR CCR3
CCR3-TM-2-1:  LLFLVTLPFW IHYVRGHNWVFGDDD    (SEQ ID NO:16)

CCR3-TM-4-1:  FGVITSIVTWGLAVLAALPEFI FYETED (SEQ ID NO:17)

CCR3-TM-6-1:  IFVIMAVFFI FWTPYNVAILLSSYQSDD (SEQ ID NO:18)

CCR3-TM-7-1:  DDLVMLVTEVIAYSHCCMNPVIYAFV    (SEQ ID NO:19)

From the GPCR CCKAR
CCKAR-TM-1-6:  DDEWQSALQILLYSIIFLLSV-       (SEQ ID NO:20)
LGNTLVITV

CCKAR-TM-2-1:  FLLSLAVSDLMLCLFCMPFNLP       (SEQ ID NO:21)

CCKAR-TM-2-2:  FLLSLAVSDLMLCLFCM PFNLIDD    (SEQ ID NO:22)

CCKAR-TM-6-4:  IVVLFFLCWMPIFSANAWRAYDTVDD   (SEQ ID NO:23)
```

One embodiment of the invention is an isolated G protein-coupled receptor (GPCR)-modulating molecule comprising a peptide or peptidomimetic that is a structural analog of a portion of a transmembrane domain of a GPCR, wherein said molecule has a first end and a second end and said molecule has at said first end a negatively charged group and at said second end a neutral charge under physiological conditions; said molecule spontaneously inserts into a membrane in the same orientation as the transmembrane domain from which it is derived; and said molecule modulates a biological property or activity of said GPCR.

In a particular embodiment, the molecules contain a hydrophilic, negatively charged non-peptidic head group and an uncharged tail, which assures correct orientation of the molecule in the cell membrane. In another embodiment, the negatively charged head group is one or more acidic amino acids.

Another embodiment is an isolated GPCR-modulating molecule comprising a peptide or peptidomimetic that is a structural analog of a portion of a transmembrane domain of CXCR4, wherein said portion of said transmembrane domain has a sequence selected from the group of sequences consisting of:

```
LLFVITLPFWAVDAVANWYFGNDD        (SEQ ID NO:1),
LLFVITLPFWAVDAVANDD             (SEQ ID NO:2),
VYVGVWIPALLLTIPDFIFANDD         (SEQ ID NO:3),
VILILAFFACWLPYYIGISID           (SEQ ID NO:4),
DDEALAFFHCCLNPILYAFL-NH2        (SEQ ID NO:5),
DDSITEALAFFHCCLNPILYAFL-NH2     (SEQ ID NO:6),
``` wherein said molecule modulates a biological activity of said CXCR4. The CXCR4 activity modulated by said peptide includes inhibition of CXCR4-mediated intracellular $Ca^{2+}$ release and inhibition of CXCR4-mediated HIV infection.

The invention also comprises methods of modulating the biological activity of a target GPCR by contacting a cell that expresses said GPCR with a molecule of the invention. In one method, the target GPCR is CXCR4, CCR5 or CCR2, and the modulated biological activity is inhibition of GPCR-mediated HIV infection. In another method, the target GPCR is CXCR4 and the modulated biological activity is inhibition of CXCR4-mediated intracellular $Ca^{2+}$ release.

Another embodiment is a method of inhibiting HIV-1 infection, comprising contacting a cell that expresses a GPCR that binds HIV-1 with a molecule that comprises a peptide or peptidomimetic that is a structural analog of a portion of a transmembrane domain of said GPCR, wherein contacting the cell with said molecule inhibits HIV-1 infection. The peptide or peptidomimetic may be a structural analog of a portion of a transmembrane domain of CXCR4 or CCR5. Peptides corresponding to TM regions of CXCR4, a GPCR that functions as a co-receptor during the cell entry of HIV, were designed and tested in cells, and yielded potent inhibition of HIV entry without apparent toxicity to the cells.

The usefulness of the method is demonstrated by specifically targeting the CXCR4 that functions as a co-receptor during the cell entry of T-cell tropic strains of HIV-1. Peptides containing 20–25 amino acid residues inhibited receptor signaling and HIV-1 infection in vitro at concentration as low as 0.2 micromolar.

In one embodiment, the molecules of the present invention mimic a transmembrane domain of the chosen receptor and block self-assembly of that receptor, possibly by competitive inhibition with the native TM domain. They thereby block or inhibit signal transduction in the affected cell.

The invention also includes peptide analogs and peptidomimetics which possess beneficial properties such as increased half-life, lack of immunogenicity, and the ability to cross the blood-brain barrier.

The peptide analogs of the invention mediate the chemical and/or biological effects of hormone agonists/antagonists or other peptides. They are believed to be useful for the development of pharmaceutical, therapeutic, and diagnostic techniques. Accordingly, the invention also provides methods for producing a prophylactic or therapeutic response in a mammal by administering to the mammal a pharmaceutically effective amount of one or more peptide analogs of the invention. In preferred embodiments, the present invention provides methods for producing such responses by modulating the activity of at least one mammalian G-protein-linked receptor by administering an effective amount of one or more peptide analogs of the invention.

In another embodiment, a peptide of the invention may modulate the biological activity of more than one GPCR. In another embodiment, more than one peptide of the invention are administered as a cocktail to modulate the biological activity of more than one GPCR.

DEFINITIONS

Figure 1:
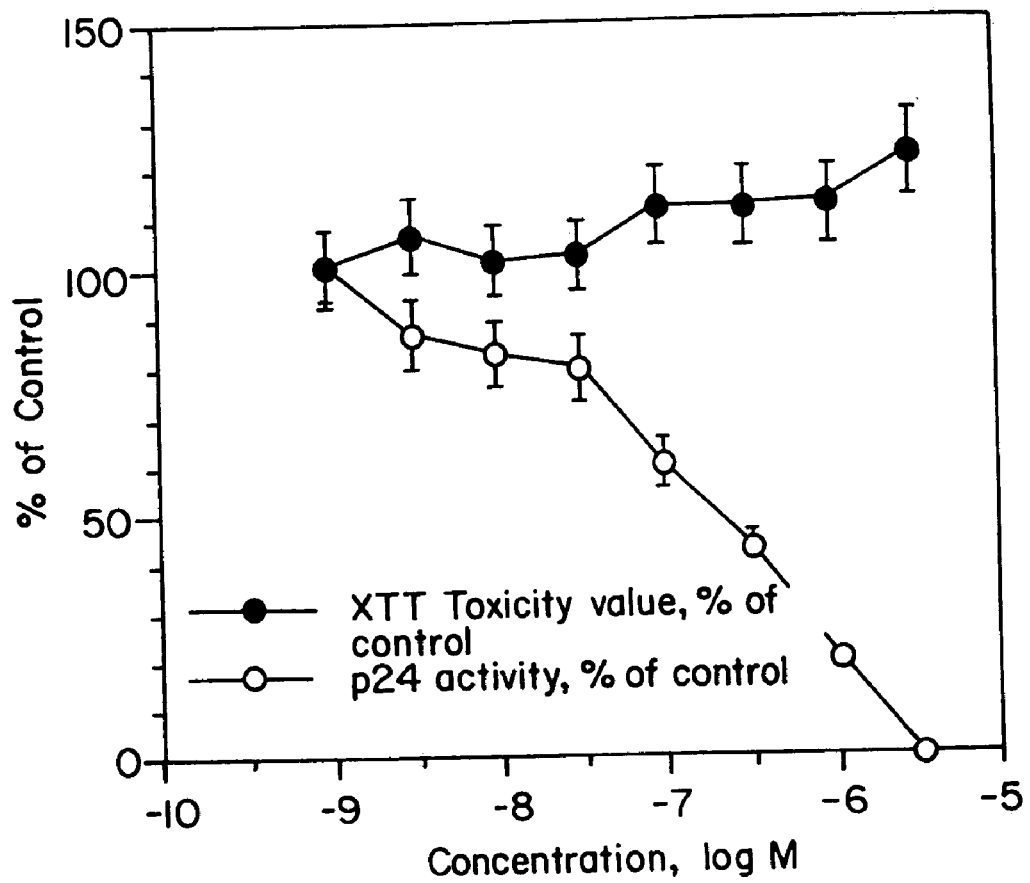
FIG. 1. Anti-HIV efficacy and toxicity of F-2-2 assay. CEM-SS cells were infected with the LAV strain of HIV-1.

A "G-protein" is any member of the superfamily of signal transducing guanine nucleotide binding proteins.

A "G-protein-coupled receptor" is any member of a superfamily of receptors that mediates signal transduction by coupling with a G protein. Examples of such receptors include, but are not limited to: CC chemokine receptor 5 (CCR5), CXC chemokine receptor (CXCR4) cholecystokinin type A receptor (CCKAR), adenosine receptors, somatostatin receptors, dopamine receptors, muscarinic cholinergic receptors, alpha-adrenergic receptors, beta-adrenergic receptors, opiate receptors, cannabinoid receptors, growth hormone releasing factor, glucagon, cAMP receptors, serotonin receptors (5-HT), histamine H2 receptors, thrombin receptors, kinin receptors, follicle stimulating hormone receptors, opsins and rhodopsins, odorant receptors, cytomegalovirus GPCRs, histamine H2 receptors, octopanmine receptors, N-formyl receptors, anaphylatoxin receptors, thromboxane receptors, IL-8 receptors, platelet activating factor receptors, endothelin receptors, bombesin gastrin releasing peptide receptor, neuromedin B preferring bombesin receptors, vasoactive intestinal peptide receptors, neurotensin receptors, bradykinin receptors, thyrotropin-releasing hormone receptors, substance P receptors, neuromedin K receptors, renal angiotensin II type I receptors, mas oncogene (angiotensin) receptors lutropin-choriogonadotropin receptors, thyrotropin receptors, follicle stimulating hormone receptors, cannabinoid receptors, glucocorticoid-induced receptors, endothelial cell GPCRs, testis GPCRs, and thoracic aorta GPCRs, and homologs thereof having a homology of at least 80% with at least one of transmembrane domains 1–7, as described herein. See, e.g., Probst et al, *DNA and Cell Biology* 11: 1–20 (1992), which is entirely incorporated herein by reference. The term further encompasses subtypes of the named receptors, and mutants and homologs thereof, along with the DNA sequences encoding the same.

The term "membrane" refers generally to a lipid bilayer. Preferably, the lipid bilayer is the plasma membrane that delimits a cell, but may be any cellular membrane. The term membrane also encompasses bilayer structures, such as artificial liposomes.

The term "GPCR polypeptide" includes polypeptides having an amino acid sequence which substantially corresponds to at least one 10 to 50 (e.g., 10, 20, 25 30 residues) amino acid fragment and/or homologous sequence of a known GPCR or group of GPCRs, wherein the GPCR polypeptide has homology of at least 80%, such as 81, 82, 83, 84, 85, 86, 87, 88, 89, 90, 91, 92 93, 94, 95, 96, 97, 98, 99 or 100% homology, while maintaining GPCR modulating activity, wherein a GPCR polypeptide of the present invention is not naturally occurring or is naturally occurring but is in a purified or isolated form which does not occur in nature.

Preferably, a GPCR polypeptide of the present invention substantially corresponds to a transmembrane domain of a GPCRs. Also preferred are GPCR polypeptides wherein the GPCR amino acid sequence is 4–10 to 50 amino acids in length, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, or any range therein.

The term "spontaneously inserts into a membrane" means that a peptide that is brought into contact with a membrane will, under physiological conditions, arrange itself within the lipid bilayer such that the hydrophobic portion of the peptide is within the membrane, and any charged end is exposed to either surface of a membrane. Preferably, molecules of the present invention that have a net negative charge at one end will orient themselves so that the charged end faces the extracellular surface of the cell.

The term "tumor cell" or "cancer cell" or "neoplastic cell" denotes a cell that demonstrates inappropriate, unregulated proliferation. A cell line is said to be "malignant" if, when the cell line is injected into a host animal, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal if cells from such tumors have human chromosomes.

The terms "treating cancer", "cancer therapy", and the like mean generally a treatment that causes any improvement in a mammal having a cancer wherein the improvement is due to treatment with a peptide of the invention. The improvement can be either subjective or objective. For example, if the mammal is human, the patient may note improved vigor or vitality or decreased pain as subjective symptoms of improvement or response to therapy. Alternatively, the clinician may notice a decrease in tumor size or tumor burden based on physical exam, laboratory parameters, tumor markers, or radiographic findings.

The phrase "inhibiting tumor [or cell] growth" generally means that the rate of increase in mass, size, number and/or the metabolism of treated cells and/or tumors is slower as a result of treatment than that of nontreated cells and/or tumors. The growth of a cell line or tumor is said to be "inhibited" by a treatment if, when assayed by means such as radioisotope incorporation into the cells, the treated cells increase in number at a rate that is less than the proliferation rate of untreated control cells, and preferably less than about 50% of the untreated cell proliferation rate. More preferably, the growth rate is inhibited by at least 80%. If growth is assayed by a means such as plating in methylcellulose, the growth of a cell line is said to be "inhibited" if the treated cells give rise to less than the number of colonies that grow from a like number of untreated cells. Preferably, the number of colonies from treated cells is less than about 70% of the number from untreated cells. More preferably, the number of colonies is decreased by at least 50%. "Inhibition of cell growth" also encompasses zero growth and, most importantly, consequent death of the tumor cells and eradication of the tumor. When measured in vivo, "inhibition of tumor growth" encompasses fewer or smaller tumors (for example, smaller diameter) as compared to control animals or untreated patients. Progression of a tumor refers to events other than growth, such as morphological and physiological changes, and changes in gene and protein expression.

Inhibition can be evaluated by any accepted method of measuring whether growth or size of the tumor and/or increase in the number of cancerous or tumor cells has been slowed, stopped, or reversed. This includes direct observation and indirect evaluation such as subjective symptoms or objective signs. The clinician may notice a decrease in tumor size or tumor burden (number of tumors) based on physical exam, laboratory parameters, tumor markers, or radiographic findings. Alternatively, if the mammal is human, the patient may note improved vigor or vitality or decreased pain as subjective symptoms of improvement or response to therapy. Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonograms, computerized axial tomography scans, nuclear magnetic resonance scans and positron emission testing.

The term "GPCR transmembrane peptide" can include a GPCR transmembrane domain fragment and/or a homologous peptide thereof, of at least 4–50, and preferably 4–30, and preferably at least 10–30 amino acids in length, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids, or any range therein, or any corresponding sequences having conservative amino acid substitutions. Sample transmembrane peptides of the invention include, but are not limited to, the peptides listed in Table I of the present disclosure. A preferred transmembrane peptide of the present invention, when contacted with a cell or membrane structure (e.g., liposome) that contains a biologically active GPCR, modulates the biological activity of said GPCR in vitro, in vivo or in situ. The concentration of the peptide in a solution that contacts the cell in vivo (e.g, blood plasma or interstitial fluid) or in vitro (e.g., culture medium) is between 1 nanomolar and 50 micromolar, preferably between 1 nanomolar and 1 micromolar, and most preferably less than 5 micromolar.

The term "residue" refers to an amino acid or amino acid mimetic incorporated in a oligopeptide by an amide bond or amide bond mimetic.

"Negatively charged" refers to those amino acids, amino acid derivatives, amino acid mimetics and chemical moieties that are negatively charged at physiological pH. Negatively charged amino acids include, for example Asp and Glu. An "acidic" residue is a residue that is negatively charged at physiological pH.

"Positively charged" refers to those amino acids, amino acid derivatives, amino acid mimetics and chemical moieties that are positively charged at physiological pH. Positively charged amino acids include, for example, Lys and Arg. A "basic residue" is a residue that is positively charged at physiological pH.

"Neutral" refers to those amino acids, amino acid derivatives, amino acid mimetics and chemical moieties that are neither positively nor negatively charged at physiological pH.

"Consensus" sequence refers to peptides which are distinct from known GPCR sequences in critical structural features, but which are derived from consensus sequences of homologous GPCR transmembrane domains 1–7. Such consensus peptides may be derived by molecular modeling, optionally combined with hydrophobicity analysis and/or fitting to model helices, as non-limiting examples. Such modeling can be accomplished according to known method steps using known modeling algorithms, such as, but not limited to, ECEPP, INSIGHT, DISCOVER, CHEM-DRAW, AMBER, FRODO and CHEM-X. Such algorithms compare transmembrane domains between related G-protein coupled receptors, determine probable energy-minimized structures and define alternative consensus polypeptide fragments.

An amino acid or nucleic acid sequence of a GPCR polypeptide of the present invention is said to "substantially correspond" to another amino acid or nucleic acid sequence, respectively, if the sequence of amino acids or nucleic acid in both molecules provides polypeptides having biological activity that is substantially similar, qualitatively or quantitatively, to the corresponding fragment of at least one GPCR transmembrane domain, or which may be synergistic when two or more transmembrane domains, consensus sequences or homologs thereof are present.

Additionally or alternatively, such "substantially corresponding" sequences of GPCR polypeptides include conservative amino acid or nucleotide substitutions, or degenerate nucleotide codon substitutions wherein individual amino acid or nucleotide substitutions are well known in the art.

The term "modulates a biological property or activity" means that in the presence of a test transmembrane peptide a measurable biological parameter or event is increased or decreased relative to a control in the absence of said peptide. Examples of biological property or activity include: the conformation of the GPCR, association of the GPCR with other molecules, signal transduction, extracellular secretion of cellular proteins, conformational changes in proteins, changes in enzymatic activity, changes in metabolic activity, changes in affinity for a ligand, changes in levels of viral infection, changes in vasodilation, modulation of heart rate, modulation of bronchodilation, modulation of endocrine secretions and modulation of gut peristalsis. Note that the GPCR biological activity need not be one that is limited to the precise in vivo role performed by the GPCR. The term also covers GPCR properties, such as viral protein binding, that are not part of the in vivo biological role of the GPCR. It further covers intrinsic properties of GPCRs that are only disclosed by experimental manipulation in the laboratory, such as the ability of GPCRs in artificial bilayers (e.g., liposomes) to interact with GPCR ligands.

"Signal transduction" is the process by which binding of a ligand to a receptor is translated into physiological change. In general, binding of a ligand to a receptor causes a change in a physical property of the receptor, for example a change in its conformation, or its orientation, or in its ability to bind other ligands. This change in a physical property can result, directly or indirectly, in increased or decreased ion fluxes, increased or decreased enzymatic activity, increased or decreased phosphorylation, increased or decreased translocation of the receptor or of any molecule (e.g., an inositol moiety or a G protein subunit) from one cellular compartment to another.

"GPCR ligands" refers to biological molecules that bind GPCRs in vitro, in situ or in vivo, and may include hormones, neurotransmitters, viruses or receptor binding domains thereof, G proteins, opsins, rhodopsins, nucleosides, nucleotides, coagulation cascade factors, odorants or pheromones, toxins, colony stimulating factors, platelet activating factors, neuroactive peptides, neurohumor, or any biologically active compounds, such as drugs or synthetic or naturally occurring compounds.

The phrase "inhibits HIV infection" means that a peptide of the invention inhibits binding of an HIV to a GPCR or inhibits a GPCR biological activity that mediates the entry and successful reproduction of an HIV virus into a GPCR-expressing cell.

The term "effective amount" means a dosage sufficient to produce a desired result. The desired result can be subjective or objective changes in the biological activity of a GPCR, especially signal transduction. Effective amounts of the GPCR polypeptide or composition, which may also include a functional derivative thereof, are from about 0.01 micrograms to about 100 mg/kg body weight, and preferably from about 10 micrograms to about 50 mg/kg body weight, such 0.05, 0.07, 0.09, 0.1, 0.5, 0.7, 0.9, 1, 2, 5, 10, 20, 25, 30, 40, 45, or 50 mg/kg.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. Such substitutions preferably are made in accordance with the following list, which substitutions may be determined by routine experimentation provide modified structural and functional properties of a synthesized polypeptide molecule, while maintaining the receptor binding, or inhibiting or mimicking biological activity, as determined by known GPCR receptor activity assays.

| Original Residue | Exemplary Substitution |
|---|---|
| Ala | Gly; Ser |
| Arg | Lys |
| Asn | Gln; His |
| Asp | Glu |
| Cys | Se |
| Gln | Asn |
| Glu | Asp |
| Gay | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Se | Thr |
| Thr | Se |
| Trp | Tyr |
| Tyr | Trp; Phe |
| Val | Ile; Leu |

Put differently, the following six groups each contain amino acids that are conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W).

See also, Creighton (1984) PROTEINS, W.H. Freeman and Company. In addition, individual substitutions, deletions or additions which alter, add or delete a single amino acid or a small percentage of amino acids in an encoded sequence are also "conservatively modified variations".

The term "substantial identity" or "substantial similarity" in the context of a polypeptide indicates that a polypeptides comprises a sequence which can have 40% sequence identity to a reference sequence, or preferably 70%, or more preferably 85% sequence identity to the reference sequence, or most preferably 90% identity over a comparison window of about 10–20 amino acid residues. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. Because the substituted amino acids have similar properties, the substitutions do not change the functional properties of the polypeptides. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution. An indication that two nucleic acid sequences are substantially identical is that the polypeptide which the first nucleic acid encodes is immunologically cross reactive with the polypeptide encoded by the second nucleic acid. Another indication that two nucleic acid sequences are substantially identical is that the two molecules hybridize to each other under stringent conditions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35: 351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, $M=5$, $N=-4$, and a comparison of both strands.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8: 91–98 (1994)). The term nucleic acid is used interchangeably with gene, cDNA, and mRNA encoded by a gene.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) ANTIBODIES, A LABORATORY MANUAL, Cold Spring Harbor Publications, New York, for a description of immunoassay formats and conditions that can be used to determine specific immunoreactivity.

DETAILED DESCRIPTION

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

The present invention is based partly on evidence that transmembrane domains (TM) of GPCRs interact in a specific way in the assembly of receptor molecules. These interactions do not lead to a rigid structure, because some flexibility is required to allow for conformational changes to be made following ligand binding in order to provide the ability of the molecule to signal from the cell surface to the intracellular parts. It was also demonstrated for several GPCRs that the transmembrane domains are involved in ligand binding and thus contain openings that allow penetration of the ligands. Reports that expression of missing transmembrane domains rescues inactive truncated V2 vasopressin, beta-adrenergic and muscarinic M3 receptors (Schoneberg et al. EMBO J. 15: 1283 (1996); Wong et al., *J. Biol. Chem.* 265: 6219 (1990); Monnot et al., *J. Biol. Chem.* 271: 1507 (1996); Gudermann et al., *Annu. Rev. Neurosci.* 20: 399 (1997); Osuga et al., *J. Biol. Chem.* 272: 25006 (1997)) suggested peptide derived from the sixth transmembrane domain of P2-adrenergic receptor was found to inhibit receptor activation and dimerization (Hebert et al., *J. Biol. Chem.*, 271(27):16384–92 (1996)). All these observations suggested to us that targeting intramembrane interactions of GPCRs can specifically regulate GPCR function.

The hydrophobic nature of the transmembrane peptides makes their penetrations into the bilayer highly probable. Orientation inside the membrane can be controlled by addition of charged residues to the terminus that is supposed to be extracellular.

1. GPCR Peptides

GPCR polypeptides of the present invention, or nucleic acids encoding therefor, include a finite set of substantially corresponding sequences as substitution peptides or polynucleotide which can be routinely obtained by one of ordinary skill in the art, without undue experimentation, based on the teachings and guidance presented herein. For a detailed description of protein chemistry and structure, see Schulz et al., PRINCIPLES OF PROTEIN STRUCTURE, Springer-Verlag, New York, 1978, and Creighton, T. E., PROTEINS: STRUCTURE AND MOLECULAR PROPERTIES, W. H. Freeman & Co., San Francisco, 1983, which are hereby incorporated by reference. For a presentation of nucleotide sequence substitutions, such as codon preferences, see Ausubel et al, supra, at sections A.1.1–A.1.24, and Sambrook et al., supra, at Appendices C and D.

GPCR polypeptides include homologous sequences and/or fragments of at least one of transmembrane domain 1–7 of one or more GPCRs or homologs thereof, which GPCR polypeptides do not occur naturally, and/or which are provided in an isolated and/or purified form not found in nature.

However, in the context of the present invention, GPCR polypeptides of greater than 15–20 amino acids are preferred such that the GPCR polypeptides are able to span the lipid bilayer.

It is particularly preferred that peptides of the invention be selected or modified so that one end is charged and the other is neutral under physiological conditions. This is so that the peptide spontaneously inserts into a membrane. It is of particular importance that the peptide insert in the same orientation as the transmembrane GPCR domain from which it is derived.

Peptides of the invention can be derived from any of the 7 TM domains. Non-limiting, illustrative examples of GPCR TM1 and TM2 transmembrane domains that are used to generate molecules of the present invention include the following:

| | | TM1 | | | SEQ ID NO: |
|---:|---|---|---|---|---:|
| | 101 | | | 150 | |
| GPCRAelegans | HPCEDIMGYV | WLTVVSFMVG | AVALVANLVV | ALVLLTSQ.. | ......RRLNV | 24 |
| GRH | NLPTLTLSGK | IRVTVTFFLF | LLSATFNASF | LLKLQKWTQK | KEKGKKLSRM | 25 |
| TRH | RAVVALEYQV | VTILLVLIIC | GLGIVGNIMV | VLVVMR.... | ...TKHMRTP | 26 |
| FSHprec | NPCEDIMGYN | ILRVLIWFIS | ILAITGNIIV | LVILTTSQYK | .......LTV | 27 |
| TSHprec | NPCEDIMGYK | FLRIVVWFVS | LLALLGNVFV | LLILLTSHYK | .......LNV | 28 |
| LH_CGprec | NPCEDIMGYD | FLRVLIWLIN | ILAIMGNMTV | LFVLLTSRY. | .......KLTV | 29 |
| PGE_EP1 | PNTSAVPPSG | ASPALPIFSM | TLGAVSNLLA | LALLAQAA.G | RLRRRRSATT | 30 |
| PGE_EP2 | SASLSPDRLN | SPVTIPAVMF | IFGVVGNLVA | IVVLCKS... | ..RKEQKETT | 31 |
| PGE_EP3 | QWLPPGE... | .SPAISSVMF | SAGVLGNLIA | LALLARRW.R | SAGRRSSLSL | 32 |
| PGF | SNTTCQTENR | LSVFFSVIFM | TVGILSNSLA | IAILMKAY.Q | RFRQKSKA.S | 33 |
| PGI | CRNLTYVRGS | VGPATSTLMF | VAGVVGNGLA | LGILSARRPA | RP......SA | 34 |
| TXA2 | NITLEERRLI | ASPWFAASFC | VVGLASNLLA | LSVLAGA... | RQGGSHTRSS | 35 |
| PAF | HMDSEFRYTL | F.PIVYSIIF | VLGVIANGYV | LWVFARLY.P | CKKFNEIK.. | 36 |
| M2 | ...YKTFEVV | FIVLVAGSLS | LVTIIGNILV | MVSI.KVN.R | HLQT.....V | 37 |
| M4 | HNRYETVEMV | FIATVTGSLS | LVTVVGNILV | MLSI.KVN.R | QLQT.....V | 38 |
| M1 | ..GKGPWQVA | FIGITTGLLS | LATVTGNLLV | LISF.KVN.T | ELKT.....V | 39 |
| M3 | LGGHTVWQVV | FIAFLTGILA | LVTIIGNILV | IVSF.KVN.K | QLKT.....V | 40 |
| M5 | LERHRLWEVI | TIAAVTAVVS | LITIVGNVLV | MISF.KVN.S | QLKT.....V | 41 |
| H1 | KTTMASPQLM | PLVVVLSTIC | LVTVGLNLLV | LYAVRSER.. | KLHT.....V | 42 |
| H2 | FCLDSTACKI | TITVVLAVLI | LITVAGNVVV | CLAVGLNR.. | RLRN.....L | 43 |
| 5HT1A | ISDVTVSYQV | ITSLLLGTLI | FCAVLGNACV | VAAIALER.. | SLQN.....V | 44 |
| 5HT1B | QDSISLPWKV | LLVMLLALIT | LATTLSNAFV | IATVYRTR.. | KLHT.....P | 45 |
| 5HT1D | DPRTLQALKI | SLAVVLSVIT | LATVLSNAFV | LTTILLTR.. | KLHT.....P | 46 |
| 5HT1E | IRPKTITEKM | LICMTLVVIT | TLTTLLNLAV | IMAIGTTK.. | KLHQ.....P | 47 |
| 5HT1F | ELLNRMPSKI | LVSLTLSGLA | LMTTTINSLV | IAAIIVTR.. | KLHH.....P | 48 |
| 5HT2A | QEKN...... | WSALLTAVVI | ILTIAGNILV | IMAVSLEK.. | KLQN.....A | 49 |
| 5HT2B | IVEEQGNKLH | WAALLILMVI | IPTIGGNTLV | ILAVSLEK.. | KLQY.....A | 50 |
| 5HT2C | ..QN...... | WPALSIVIII | IMTIGGNILV | IMAVSMEK.. | KLHN.....A | 51 |
| 5HT5A | SSPLLSVFGV | LILTLLGFLV | AATFAWNLLV | LATILRVR.. | TFHR.....V | 52 |
| 5HT5Brat | REPPFSAFTV | LVVTLLVLLI | AATFLWNLLV | LVTILRVR.. | AFHR.....V | 53 |
| 5HT6rat | GPPPAPGGSG | WVAAALCVVI | VLTAAANSLL | IVLICTQP.. | AVRN.....T | 54 |
| 5HT7 | QINYGRVEKV | VIGSILTLIT | LLTIAGNCLV | VISVCFVK.. | KLRQ.....P | 55 |
| alpha1A | GGLVVSAQGV | GVGVFLAAFI | LMAVAGNLLV | ILSVACNR.. | HLQT.....V | 56 |
| alpha1B | ..QLDITRAI | SVGLVLGAFI | LFAIVGNILV | ILSVACNR.. | HLRT.....P | 57 |
| alpha1C | PAPVNISKAI | LLGVILGGLI | LFGVLCNILV | ILSVACHR.. | HLHS.....V | 58 |
| alpha2A | ...YSLQVTL | TLVCLAGLLM | LLTVFGNVLV | IIAVFTSR.. | ALKA.....P | 59 |
| alpha2B | QDPYSVQATA | AIAAAITFLI | LFTIFGNALV | ILAVLTSR.. | SLRA.....P | 60 |

-continued

```
     alpha2C1  RGQYSAGAVA GLAAVVGFLI VFTVVGNVLV VIAVLTSR.. ALRA.....P 61
     alpha2C2  RGQYSAGAVA GLAAVVGFLI VFTVVGNVLV VIAVLTSR.. ALRA.....P 61
        beta1  EPLSQQWTAG M.GLLMALIV LLIVAGNVLV IVAIAKTP.. RLQT.....L 62
        beta2  QQRDEVWVVG M.GIVMSLIV LAIVFGNVLV ITAIAKFE.. RLQT.....V 63
        beta3  GLPGVPWEAA LAGALLALAV LATVGGNLLV IVAIAWTP.. RLQT.....M 64
   beta4turkey SWAAVLSRQW AVGAALSITI LVIVAGNLLV IVAIAKTP.. RLQT.....M 65
          D1A  VVERDFSVRI LTACFLSLLI LSTLLGNTLV CAAVIRFR.. HLRSK....V 66
           D2  DGKADRPHYN YYATLLTLLI AVIVFGNVLV CMAVSREK.. ALQT.....T 67
           D3  TGASQARPHA YYALSYCALI LAIVFGNGLV CMAVLKER.. ALQT.....T 68
           D4  ASAGLAGQGA AALVGGVLLI GAVLAGNSLV CVSVATER.. ALQT.....P 69
           D5  GAPPLGPSQV VTACLLTLLI IWTLLGNVLV CAAIVRSR.. HLRAN....M 70
           A1  MPPSISAFQA AYIGIEVLIA LVSVPGNVLV IWAVKVNQ.. ALRD.....A 71
          A2a  ...MPIMGSS VYITVELAIA VLAILGNVLV CWAVWLNS.. NLQN.....V 72
          A2b  ..MLLETQDA LYVALELVIA ALSVAGNVLV CAAVGTAN.. TLQT.....P 73
           A3  NSTTLSLANV TYITMEIFIG LCAIVGNVLV ICVVKLNP.. SLSQT....T 74
       OCdrome  LAVPE.WEAL LTALVLSVII VLTIIGNILV ILSVFTYK.. PLRI.....V 75
         ACTH  RNNSDCPRVV LPEEIFFTIS IVGVLENLIV LLAVFKNK.. NLQA.....P 76
          MSH  QTGARCLEVS ISDGLFLSLG LVSLVENALV VATIAKNR.. NLHS.....P 77
          MC3  SSSAFCEQVF IKPEIFLSLG IVSLLENILV ILAVVRNG.. NLHS.....P 78
          MC4  SDGGCYEQLF VSPEVFVTLG VISLLENILV IVAIAKNK.. NLHS.....P 79
          MC5  NKSSPCEDMG IAVEVFLTLG VISLLENILV IGAIVKNK.. NLHS.....P 80
     melatonin DGARPSWLAS ALACVLIFTI VVDILGNLLV ILSVYRNKKL .......RNA 81
      oxytocin R..RNEALAR VEVAVLCLIL LLALSGNACV LLALRTTRQK .......HSR 82
  conopressinLs FHGVDEDLLK IEIAVQATIL YMTLFGNGIV LLVLRLRRQK .......LRT 83
          V1A  RDVRNEELAK LEIAVLAVTF AVAVLGNSSV LLAL....... .HRTPRKTSR 84
          V1B  WLGRDEELAK VEIGVLATVL VLATGGNLAV LLTLGQLGRK .......RSR 85
           V2  LDTRDPLLAR AELALLSIVF VAVALSNGLV LAALA..... RRGRRGHWAP 86
        CCK_A  PRPSKEWQPA VQILLYSLIF LLSVLGNTLV ITVLI..... RNKRM..RTV 87
        CCK_B  GAGTRELELA IRITLYAVIF LMSVGGNMLI IVVLGLS... ..RRL..RTV 88
         NPY1  DCHLPLAMIF TLALAYGAVI ILGVSGNLAL IIIIL..... KQKEM..RNV 89
          NTR  DVNTDIYSKV LVTAVYLALF VVGTVGNTVT AFTLAR.... KKSLQSLQST 90
          NK1  QFVQPAWQIV LWAAAYTVIV VTSVVGNVVV MWIILA.... .HKRM..RTV 91
          NK2  AFSMPSWQLA LWAPAYLALV LVAVTGNAIV IWIILA.... .HRRM..RTV 92
          NK3  QFVQPSWRIA LWSLAYGVVV AVAVLGNLIV IWIILA.... .HKRM..RTV 93
       blueops YHIAPVWAFY LQAAFMGTVF LIGFPLNANV LVATL..... RYKKL..RQP 94
      greenops YHIAPRWVYH LTSVWMIFVV IASVFTNGLV LAATM..... KFKKL..RHP 95
        redops YHIAPRWVYH LTSVWMIFVV TASVFTNGLV LAATM..... KFKKL..RHP 96
      rhodopsin YYLAEPWQFS MLAAYMFLLI VLGFPINFLT LYVTVQ.... .HKKL..RTP 97
    violetopsGg YHIAPPWAFY LQTAFMGIVF AVGTPLNAVV LWVTVRYKRL .......RQP 98
     opsin_crab FPPMNPLWYS ILGVAMIILG IICVLGNGMV IYLMMTTKSL .......RTP 99
```

```
     ET_Aprec QTKITSAFKY INTVISCTIF IVGMVGNATL LRIIYQ.... .NKCM..RNG 100
     ET_Bprec PIEIKETFKY INTVVSCLVF VLGIIGNSTL LRIIYKNK.. ...CM..RNG 101
     ET_Cfrog RAKIRHAFKY VTTILSCVIF LVGIVGNSTL LRIIYKNK.. ...CM..RNG 102
      galanin PLFGIGVENF VTLVVFGLIF ALGVLGNSLV ITVLARSK.. ...PGKPRST 103
          NMB GTTTELVIRC VIPSLYLLII TVGLLGNIML VKIFITNS.. ...AM..RSV 104
          GRP DDWSHPGILY VIPAVYGVII LIGLIGNITL IKIFCTVK.. ...SM..RNV 105
         BRS3 DNSPGIEALC AIYITYAVII SVGILGNAIL IKVFFKTK.. ...SM..QTV 106
      deltaOP GSASSLALAI AITALYSAVC AVGLLGNVLV MFGIVRYT.. ...KM..KTA 107
      kappaOP PAHISPAIPV IITAVYSVVF VVGLVGNSLV MFVIIRYT.. ...KM..KTA 108
         muOP GSP.SMITAI TIMALYSIVC VVGLFGNFLV MYVIVRYT.. ...KM..KTA 109
         OPRX GAFLPLGLKV TIVGLYLAVC VGGLLGNCLV MYVILRHT.. ...KM..KTA 110
          CB1 FMVLNPSQQL AIAVLSLTLG TFTVLENLLV LCVILHSR.. SLRCR....P 111
          CB2 YMILSGPQKT AVAVLCTLLG LLSALENVAV LYLILSSH.. QLRRK....P 112
        SSTR1 TLSEGQGSAI LISFIYSVVC LVGLCGNSMV IYVILRYA.. ...KM..KTA 113
        SSTR2 EPYYDLTSNA VLTFIYFVVC IIGLCGNTLV IYVILRYA.. ...KM..KTI 114
        SSTR3 SPAGLAVSGV LIPLVYLVVC VVGLLGNSLV IYVVLRHT.. ...AS..PSV 115
        SSTR4 GDARAAG.MV AIQCIYALVC LVGLVGNALV IFVILRYA.. ...KM..KTA 116
        SSTR5 PAPSAGARAV LVPVLYLLVC AAGLGGNTLV IYVVLRFA.. ...KM..KTV 117
         IL8A MLETETLNKY VVIIAYALVF LLSLLGNSLV MLVILYSR.. ...VG..RSV 118
         IL8B EPESLEINKY FVVIIYALVF LLSLLGNSLV MLVILYSR.. ...VG..RSV 119
         AT1a KAGRHNYIFV MIPTLYSIIF VVGIFGNSLV VIVIYFYM.. ...KL..KTV 120
      AT1brat KAGRHNYIFV MIPTLYSIIF VVGIFGNSLV VIVIYFYM.. ...KL..KTV 120
          AT2 QKPSDKH.LD AIPILYYIIF VIGFLVNIVV VTLFCCQK.. ...GP..KKV 121
          BK1 APEAWDLLHR VLPTFIISIC FFGLLGNLFV LLVFLLPR.. ......RQLNV 122
          BK2 QVEWLGWLNT IQPPFLWVLF VLATLENIFV LSVFCLHK.. ......SSCTV 123
         P2Y7 PSLGVEFISL LAIILLSVAL AVGLPGNSFV VWSILKRMQ. ......KRSV 124
         P2Y6 CVYREFDKRL LLPPVYSVVL VVGLPLNVCV IAQICASRR. ......TLTR 125
         P2Y5 CSTEDSFKYT LYGCVFSMVF VLGLIANCVA IYIFTFTLK. ......VRNE 126
         P2Y4 CWFDEDFKFI LLPVSYAVVF VLGLGLNAPT LWLFIFRLR. ......PWDA 127
     P2Y3chick CTFHEEFKQV LLQLVYSVVF LLGLPLNAVV IGQIWLARK. ......ALTR 128
         P2Y2 CFFNEDFKYV LLPVSYGVVC VLGLCLNAVG LYIFLCRLK. ......TWNA 129
         P2Y1 ALTKTGFQFY YLPAVYILVF IIGFLGNSVA IWMFVFHMK. ......PWSG 130
      THRprec GYLTSSWLTL FVPSVYTGVF VVSLPLNIMA IVVFILKM.. ...KV..KKP 131
          C5a TSNTLRVPDI LALVIFAVVF LVGVLGNALV VWVTAFEA.. ...K...RTI 132
     GP01mouse AESEPELVVN PWDIVLCSSG TLICCENAVV VLIIF.HSPS LR......AP 133
      R334rat VESEPELVVN PWDIVLCSSG TLICCENAVV VLIIF.HSPS LR......AP 134
     GP21mouse GPATLLPSPR AWDVVLCISG TLVSCENALV VAIIV.GTPA FR......AP 135
     GCRCmouse AESQNPTVKA LLIVAYSFTI VFSLFGNVLV CHVIFK.NQR ......MHSA 136
         TXKR ...QPPWAVA LWSLAYGAVV AVAVLGNLVV IWIVLA.HKR MR......TV 137
       G10Drat MELNENTKQV VLFVFYLAIF VVGLVENVLV IC.VNCRRSG R......VGM 138
```

-continued

```
        RDC1 NMPNKSVLLY TLSFIYIFIF VIGMIANSVV VW.VNIQAKT TGYDT..... 139
        BLR1 ...MASFKAV FVPVAYSLIF LLGVIGNVLV LV.ILERHRQ TRSSTE.... 140
         CL5 REENANFNKI FLPTIYSIIF LTGIVGNGLV IL.VMGYQKK LRSMTDKYR. 141
         LCR1 REENANFNKI FLPTIYSIIF LTGIVGNGLV IL.VMGYQKK LRSMTDKYR. 141
         EBI1 KKDVRNFKAW FLPIMYSIIC FVGLLGNGLV VL.TYIYFKR LKTMTDTY.. 142
      RBS1rat LGDIVAFGTI FLSIFYSLVF TFGLVGNLLV VL.ALTNSRK SKSITDIY.. 143
         EBI2 LYAHHSTARI VMPLHYSLVF IIGLVGNLLA LV.VIVQNRK KINSTTLY.. 144
    GCRTchick CSTEDSFKYT LYGCVFSMVF VLGLIANCVA IY.IFTFTLK VRNETTTY.. 145
          APJ EYTDWKSSGA LIPAIYMLVF LLGTTGNGLV LWTVFRSSRE KRRSAD.... 146
       RTArat EQIATLPPPA VTNYIFLLLC LCGLVGNGLV LWFFGFSIK. .RT......P 147
        UHRrat SLQLVHQLKG LIVMLYSIVV VVGLVGNCLL VLVIARVR.. .....RLHNV 148
        FMRL1 EPAGHTVLWI FSLLVHGVTF VFGVLGNGLV IWVA.GFR.. .....MTRTV 149
        FMRL2 ESAGYTVLRI LPLVVLGVTF VLGVLGNGLV IWVA.GFR.. .....MTRTV 150
         fMLP VSAGYLFLDI ITYLVFAVTF VLGVLGNGLV IWVA.GFR.. .....MTHTV 151
   OLF1catfish NGFYNIPHTK YYYAFLCIAY AVTVLGNSFI MCTIYLAR.. .....SLHTA 152
   OLF3catfish TGLYNIPHAK YYYLFLCFVY TVTFLGNSFI MGTIYLAR.. .....SLHTA 153
   OLF8catfish GFHDLGEWGP ILSIPYLLMF LSSTSNLTL IYLIISQR.. .....ALHSP 154
  OLF32Acatfish SGFSGIPFSQ YYFAFLIFIY IISLCGNSIV LFMILVDR.. .....TLHIP 155
  OLF32Bcatfish SGFSGIPFSQ YYFVFLIFIY IISLCGNSIV LFMILVDR.. .....TLHIP 156
  OLF32Ccatfish SGFSGIPFSQ YYFVFLIFIY IISLCGNSIV LFMILVDR.. .....TLHIP 156
  OLF32Dcatfish SGFSGIPFSQ YYFVFLIFIY IISLCGNSIV LFMILVDR.. .....TLHIP 156
  OLF47catfish IAYNSLGNKN YLILALGIIY LITLLCNFTL LAIILMNS.. .....SLQNP 157
 OLF202catfish FPGLPPNYYG LVSVVMFFVY VCTLIGNCTF FTLFLREK.. .....SLQKP 158
OLFCOR1chicken LTD.NPGLQM PLFMVFLAIY TITLLTNLGL IALISVDL.. .....HLQTP 159
OLFCOR2chicken LTD.NPRLQM PLFMVFLVIY TTTLLTNLGL IALIGMDL.. .....HLQTP 160
OLFCOR3chicken LTD.NPGLQM PLFMVFLAIY TITLLTNLGL IRLISVDL.. .....HLQTP 161
OLFCOR4chicken LTD.NPGLQM PLFMVFLAIY TITLLTNLGL IRLISVDL.. .....HLQTP 161
OLFCOR5chicken LTD.NPRLQM PLFMVFLAIY TITLLANLGL IALISVDF.. .....HLQTP 162
OLFCOR6chicken LTD.NPGLQM PLFMVFLAIY TITLLTNLGL IALIRIDL.. .....QLQTP 163
       OLFdog LPI.DPDQRD LFYALFLAMY VTTILGNLLI IVLIQLDS.. .....HLHTP 164
       OLF07E MSE.SPEQQQ ILFWMFLSMY LVTVVGNVLI ILAISSDS.. .....RLHTP 165
       OLF07I LPI.QPEQQN LCYALFLAMY LTTLLGNLLI IVLIRLDS.. .....HLHTP 166
       OLF07J FSS.FHEQQI TLFGVFLALY ILTLAGNIII VTIIRIDL.. .....HLHTP 167
    OLFOR3mouse VSD.HPHLEI IFFAVILASY LLTLVGNLTI ILLSRLDA.. .....RLHTP 168
       OLFrat LTK.QPELLL PLFFLFLVIY VLTVVGNLGM ILLIIVSP.. .....LLHTP 169
      OLFF3rat FVE.NKDLQP LIYGLFLSMY LVTVIGNISI IVAIISDP.. .....CLHTP 170
      OLFF5rat LSR.QPQQQQ LLFLLFLIMY LATVLGNLLI ILAIGTDS.. .....RLHTP 171
      OLFF6rat FPG.PRSMRI GLFLLFLVMY LLTVVGNLAI ISLVGAHR.. .....CLQTP 172
     OLFF12rat FTE.NPQLHF LIFALFLSMY LVTVLGNLLI IMAIITQS.. .....HLHTP 173
      OLFI3rat LPI.PEEHQH LFYALFLVMY LTTILGNLLI IVLVQLDS.. .....QLHTP 174
```

```
    OLFI7rat   FPA.PAPLRV LLFFLSLLXY VLVLTENMLI IIAIRNHP.. .....TLHKP 175
    OLFI8rat   LPI.PPEHQQ LFFALFLIMY LTTFLGNLLI VVLVQLDS.. .....HLHTP 176
    OLFI9rat   LPF.PPEYQH LFYALFLAMY LTTLLGNLII IILILLDS.. .....HLHTP 177
   OLFI14rat   LPI.PSEYHL LFYALFLAMY LTIILGNLLI IVLVRLDS.. .....HLHMP 178
   OLFI15rat   LPI.PSEHQH VFYALFLSMY LTTVLGNLII IILIHLDS.. .....HLHTP 179
  OLFOR17_40   LLE.APGLQP VVFVLFLFAY LVTVRGNLSI LAAVLVEP.. .....KLHTP 180
    GUST27rat  ....MILNCN PFSGLFLSMY LVTVLGNLLI ILAVSSNSHL .......HNL 181
          RPE  PTGFGELEVL AVGMVLLVEA LSGLSLNTLT IFSFCKTPEL .......RTP 182
         HHRF1 FTDVLNQSKP VTLFLYGVVF LFGSIGNFLV IFTITWRRRI .......QCS 183
         HHRF2 NSTEIYQLFE YTRLGVWLMC IVGTFLNVLV ITTILYYRRK K......KSP 184
         HHRF3 MTGPLFAIRT TEAVLNTFII FVGGPLNAIV LITQLLTNRV LG.....YST 185
        MCP-1A ..DVKQIGAQ LLPPLYSLVF IFGFVGNMLV VLILINCKKL .......KCL 186
        MCP-1B ..DVKQIGAQ LLPPLYSLVF IFGFVGNMLV VLILINCKKL .......KCL 186
    PPR1bovine ..EVRKFAKV FLPAFFTIAF IIGLAGNSTV VAIYAYYKKR .......RTK 187

TM2
                                                                SEQ
                                                                 ID
                 151                                    200     NO:

GPCRAelegans  TRFLMCNLAF ADFILGLYIF ILTSVSAVTR GDYHNYVQQW QNGAGCKILG 188
          GRH .KLLLKHLTL ANLLETLIVM PLDGMWNITV QWYA...... .GELLCKVLS 189
          TRH TNCYLVSLAV ADLMVLVAAG LPNITDSIYG SWVYGYV... ....GCLCIT 190
       FSHprec PRFLMCNLAF ADLCIGIYLL LIASVDIHTK SQYHNYAIDW QTGAGCDAAG 191
       TSHprec PRFLMCNLAF ADFCMGMYLL LIASVDLYTH SEYYNHAIDW QTGPGCNTAG 192
    LH_CGprec PRFLMCNLSF ADFCMGLYLL LIASVDSQTK GQYYNHAIDW QTGSGCSTAG 193
       PGE_EP1 FLLFVASLLA TDLAGHVIPG ALVLRLYTA. .......GRA PAGGACHFLG 194
       PGE_EP2 FYTLVCGLAV TDLLGTLLVS PVTIATYMKG ......QWPG GQP.LCEYST 195
       PGE_EP3 FHVLVTELVF TDLLGTCLIS PVVLASYARN QT..LVALAP ESR.ACTYFA 196
           PGF FLLLASGLVI TDFFGHLING AIAVFVYASD KE..WIRFDQ .SNVLCSIFG 197
           PGI FAVLVTGLAA TDLLGTSFLS PAVFVAYARN SS..LLGLAR GGPALCDAFA 198
          TXA2 FLTFLCGLVL TDFLGLLVTG TIVVSQHAAL FE..WHAVDP GCR.LCRFMG 199
           PAF ..IFMVNLTM ADMLFLITLP LWIVYYQ.NQ GNWIL..... PK.FLCNVAG 200
            M2 NNYFLFSLAC ADLIIGVFSM NLYTLYTVIG ......YWPL .GPVVCDLWL 201
            M4 NNYFLFSLAC ADLIIGAFSM NLYTVYIIKG ......YWPL .GAVVCDLWL 202
            M1 NNYFLLSLAC ADLIIGTFSM NLYTTYLLMG ......HWAL .GTLACDLWL 203
            M3 NNYFLLSLAC ADLIIGVISM NLFTTYIIMN ......RWAL .GNLACDLWL 204
            M5 NNYYLLSLAC ADLIIGIFSM NLYTTYILMG ......RWAL .GSLACDLWL 205
            H1 GNLYIVSLSV ADLIVGAVVM PMNILYLLMS ......KWSL .GRPLCLFWL 206
            H2 TNCFIVSLAI TDLLLGLLVL PFSAIYQLSC ......KWSF G.KVFCNIYT 207
         5HT1A ANYLIGSLAV TDLMVSVLVL PMAALYQVLN ......KWTL .GQVTCDLFI 208
         5HT1B ANYLIASLAV TDLLVSILVM PISTMYTVTG ......RWTL .GQVVCDFWL 209
         5HT1D ANYLIGSLAT TDLLVSILVM PISIAYTITH ......TWNF .GQILCDIWL 210
```

```
        5HT1E  ANYLICSLAV  TDLLVAVLVM  PLSIIYIVMD  ......RWKL  .GYFLCEVWL  211
        5HT1F  ANYLICSLAV  TDFLVAVLVM  PFSIVYIVRE  ......SWIM  .GQVVCDIWL  212
        5HT2A  TNYFLMSLAI  ADMLLGFLVM  PVSMLTILYG  .....YRWPL  P.SKLCAVWI  213
        5HT2B  TNYFLMSLAV  ADLLVGLFVM  PIALLTIMFE  .....AMWPL  P.LVLCPAWL  214
        5HT2C  TNYFLMSLAI  ADMLVGLLVM  PLSLLAILYD  .....YVWPL  P.RYLCPVWI  215
        5HT5A  PHNLVASMAV  SDVLVAALVM  PLSLVHELS.  ....GRRWQL  .GRRLCQLWI  216
     5HT5Brat  PHNLVASTAV  SDVLVAALVM  PLSLVSELSA  ....GRRWQL  .GRSLCHVWI  217
      5HT6rat  SNFFLVSLFT  SDLMVGLVVM  PPAMLNALYG  ......RWVL  A.RGLCLLWT  218
         5HT7  SNYLIVSLAL  ADLSVAVAVM  PFVSVTDLIG  G.....KWIF  .GHFFCNVFI  219
       alpha1A  TNYFIVNLAV  ADLLLSATVL  PFSATMEVLG  ......FWAF  G.RAFCDVWA  220
       alpha1B  TNYFIVNLAM  ADLLLSFTVL  PFSAALEVLG  ......YWVL  G.RIFCDIWA  221
       alpha1C  THYYIVNLAV  ADLLLTSTVL  PFSAIFEVLG  ......YWAF  G.RVFCNIWA  222
       alpha2A  QNLFLVSLAS  ADILVATLVI  PFSLANEVMG  .Y.....WYF  .GKAWCEIYL  223
       alpha2B  QNLFLVSLAA  ADILVATLII  PFSLANELLG  .Y.....WYF  R.RTWCEVYL  224
      alpha2C1  QNLFLVSLAS  ADILVATLVM  PFSLANELMA  .Y.....WYF  .GQVWCGVYL  225
      alpha2C2  QNLFLVSLAS  ADILVATLVM  PFSLANELMA  .Y.....WYF  .GQVWCGVYL  225
         beta1  TNLFIMSLAS  ADLVMGLLVV  PFGATIVVWG  ......RWEY  GS.FFCELWT  226
         beta2  TNYFITSLAC  ADLVMGLAVV  PFGAAHILMK  ......MWTF  GN.FWCEFWT  227
         beta3  TNVFVTSLAA  ADLVMGLLVV  PPAATLALTG  ......HWPL  GA.TGCELWT  228
   beta4turkey  TNVFVTSLAC  ADLVMGLLVV  PPGATILLSG  ......HWPY  GT.VVCELWT  229
           D1A  TNFFVISLAV  SDLLVAVLVM  PWKAVAEIAG  ......FWPF  GS..FCNIWV  230
            D2  TNYLIVSLAV  ADLLVATLVM  PWVVYLEVVG  E......WKF  S.RIHCDIFV  231
            D3  TNYLVVSLAV  ADLLVATLVM  PWVVYLEVTG  GV.....WNF  S.RICCDVFV  232
            D4  TNSFIVSLAA  ADLLLALLVL  PLFVYSEVQG  GA.....WLL  SPRLC.DALM  233
            D5  TNVFIVSLAV  SDLFVALLVM  PWKAVAEVAG  ......YWPF  GA..FCDVWV  234
            A1  TFCFIVSLAV  ADVAVGALVI  PLAILINIGP  QTYFHTCL..  .......MVA  235
           A2a  TNYFVVSLAA  ADIAVGVLAI  PFAITISTGF  CAACHGCL..  .......FIA  236
           A2b  TNYFLVSLAA  ADVAVGLFAI  PFAITISLGF  CTDFYGCL..  .......FLA  237
            A3  TFYFIVSLAL  ADIAVGVLVM  PLAIVVSLGI  TIHFYSCL..  .......FMT  238
       OCdrome  QNFFIVSLAV  ADLTVALLVL  PFNVAYSILG  R......WEF  GI.HLCKLWL  239
          ACTH  MYFFICSLAI  SDMLGSLYKI  LENILIILRN  MGYLKPRGSF  ET.TADDIID  240
           MSH  MYCFICCLAL  SDLLVSGTNV  LETAVILLLE  AGALVARAAV  LQ.QLDNVID  241
           MC3  MYFFLCSLAV  ADMLVSVSNA  LETIMIAIVH  SDDYTFEDQF  IQ.HMDNIFD  242
           MC4  MYFFICSLAV  ADMLVSVSNG  SETIIITLLN  STD.TDAQSF  TV.NIDNVID  243
           MC5  MYFFVCSLAV  ADMLVSMSSA  WETITIYLLN  NKHLVIADAF  V.RHIDVNFD  244
      melatonin GNIFVVSLAV  ADLVVAIYPY  PLVLMSIFNN  GWNLGYLH..  ......CQVSG  245
      oxytocin  LFFFMKHLSI  ADLVVAVFQV  LPQLLWDITF  RFYGP.....  ..DLLCRLVK  246
   conopressinLs MQWFIAHLAF ADIFVGFFNI  LPQLISDVTI  VFHGDD....  ...FTCRFIK  247
           V1A  MHLFIRHLSL  ADLAVAFFQV  LPQMCWDITY  RFRGPD....  ...WLCRVVK  248
           V1B  MHLFVLHLAL  TDLAVALFQV  LPQLLWDITY  RFQGP.....  ..DLLCRAVK  249
```

-continued

```
          V2 IHVFIGHLCL ADLAVALFQV LPQLAWKATD RFRGPD.... ...ALCRAVK 250
       CCK_A TNIFLLSLAV SDLMLCLFCM PFNLIPNLLK DFIFGS.... ...AVCKTTT 251
       CCK_B TNAFLLSLAV SDLLLAVACM PFTLLPNLMG TFIFGT.... ...VICKAVS 252
        NPY1 TNILIVNLSF SDLLVAIMCL PFTFVYTLMD HWVFGE.... ...AMCKLNP 253
         NTR VHYHLGSLAL SDLLTLLLAM PVELYNFIWV HHPWAF.... .GDAGCRGYY 254
         NK1 TNYFLVNLAF AEASMAAFNT VVNFTYAVHN EWYYGL.... ...FYCKFHN 255
         NK2 TNYFIVNLAL ADLCMAAFNA AFNFVYASHN IWYFGR.... ...AFCYFQN 256
         NK3 TNYFLVNLAF SDASMAAFNT LVNFIYALHS EWYFGA.... ...NYCRFQN 257
     blueops LNYILVNVSF GGFLLCIFSV FPVFVASCNG YFVFGR.... ...HVCALEG 258
    greenops LNWILVNLAV ADLAETVIAS TISVVNQVYG YFVLGH.... ...PMCVLEG 259
      redops LNWILVNLAV ADLAETVIAS TISIVNQVSG YFVLGH.... ...PMCVLEG 260
    rhodopsin LNYILLNLAV ADLFMVLGGF TSTLYTSLHG YFVFGP.... ...TGCNLEG 261
 violetopsGg LNYILVNISA SGFVSCVLSV FVVFVASARG YFVFG..... ..KRVCELEA 262
  opsin_crab TNLLVVNLAF SDFCMMAFMM PTMTSNCFAE TWILG..... ..PFMCEVYG 263
    ETA_prec PNALIASLAL GDLIYVVIDL PINVFKLLAG RWPFDH.NDF GV.FLCKLFP 264
    ETB_prec PNILIASLAL GDLLHIVIDI PINVYKLLAE DWPFGAE... ....MCKLVP 265
     ET_Cfrog PNVLIASLAL GDLFYILIAI PIISISFWLS TGH....... ....SEYIYQ 266
     galanin TNLFILNLSI ADLAYLLFCI PFQATVYALP TWVLGA.... ...FICKFIH 267
         NMB PNIFISNLAA GDLLLLLTCV PVDASRYFFD EWMFGKVG.. ......CKLIP 268
         GRP PNLFISSLAL GDLLLLITCA PVDASRYLAD RWLFGRIG.. ......CKLIP 269
        BRS3 PNIFITSLAF GDLLLLLTCV PVDATHYLAE GWLFGRIG.. ......CKVLS 270
      deltaOP TNIYIFNLAL ADALATSTLP FQSAKYLMET .WPFGE.... ...LLCKAVL 271
      kappaOP TNIYIFNLAL ADALVTTTMP FQSTVYLMNS .WPFGD.... ...VLCKIVI 272
         muOP TNIYIFNLAL ADALATSTLP FQSVNYLMGT .WPFGT.... ...ILCKIVI 273
         OPRX TNIYIFNLAL ADTLVLLTLP FQGTDILLGF .WPFGN.... ...ALCKTVI 274
         CB1 SYHFIGSLAV ADLLGSVIFV YSFIDFHVFH RKD....... .SRNVFLFKL 275
         CB2 SYLFIGSLAG ADFLASVVFA CSFVNFHVFH GVD....... .SKAVFLLKI 276
       SSTR1 TNIYILNLAI ADELLMLSVP FLVTSTLLRH .WPFGA.... ...LLCRLVL 277
       SSTR2 TNIYILNLAI ADELFMLGLP FLAMQVALVH .WPFGK.... ...AICRVVM 278
       SSTR3 TNVYILNLAL ADELFMLGLP FLAAQNALSY .WPFGS.... ...LMCRLVM 279
       SSTR4 TNIYLLNLAV ADELFMLSVP FVASSAALRH .WPFGS.... ...VLCRAVL 280
       SSTR5 TNIYILNLAV ADVLYMLGLP FLATQNAASF .WPFGP.... ...VLCRLVM 281
        IL8A TDVYLLNLAL ADLLFALTLP IWAA..SKVN GWIFGT.... ...FLCKVVS 282
        IL8B TDVYLLNLAL ADLLFALTLP IWAA..SKVN GWIFGT.... ...FLCKVVS 282
        AT1a ASVFLLNLAL ADLCFLLTLP LWAVYTAMEY RWPFGN.... ...YLCKIAS 283
      AT1brat ASVFLLNLAL ADLCFLLTLP LWAVYTAMEY RWPFGN.... ...HLCKIAS 284
         AT2 SSIYIFNLAV ADLLLLATLP LWATYYSYRY DWLFGP.... ...VMCKVFG 285
         BK1 AEIYLANLAA SDLVFVLGLP FWAENIWNQF NWPFGA.... ...LLCRVIN 286
         BK2 AEIYLGNLAA ADLILACGLP FWAITISNNF DWLFGE.... ...TLCRVVN 287
        P2Y7 TALMVLNLAL ADLAVLLTAP FFLHFLAQGT WSFGLA.... ....GCRLCH 288
```

```
         P2Y6 SAVYTLNLAL ADLLYACSLP LLIYNYARGD HWPFGD.... ...LACRLVR 289

P2Y5 TTTYMLNLAI SDLLFVFTLP FRIYYFVVRN .WPFGD.... ...VLCKISV 290

P2Y4 TATYMFHLAL SDTLYVVSLP TLIYYYAAHN HWPFGT.... ...EICKFVR 291

P2Y3chick TTIYMLNLAM ADLLYVCSLP LLIYNYTQKD YWPFGD.... ...FTCKFVR 292

P2Y2 STTYMFHLAV SDALYAASLP LLVYYYARGD HWPFST.... ...VLCKLVR 293

P2Y1 ISVYMFNLAL ADFLYVLTLP ADIFYYFNKT DWIFGD.... ...AWCKLQR 294

THRprec AVVYMLHLAT ADVLFVSVLP FKISYYFSGS DWQFGS.... ...ELCRFVT 295

C5a NAIWFLNLAV ADFLSCLALP ILFTSIVQHH WPFGGA.... ... ACSILP 296

GP01mouse MFLLIGSLAL ADLLAGLGLI INFVFAYLLQ ....SE.... ...ATKLVTI 297

R334rat MFLLIGSLAL ADLLAGLGLI INFVFAYLLQ ....SE.... ...ATKLVTI 297

GP21mouse MFLLVGSLAV ADLLAGLGLV LHFAADFCIG ....SP.... ...EMSLMLV 298

GCRCmouse TSLFIVNLAV ADIMITLLNT PFTLVRFVNS TWVFGK.... ...GMCHVSR 299

TXKR TNSFLVNLAF ADAAMAALNA LVNFIYALHG EWYFGA.... ...NYCRFQN 300

G10Drat LNLYILNMAV ADLGIILSLP VWMLEVMLEY TWLWGS.... ...FSCRFIH 301

RDC1 .HCYILNLAI ADLWVVLTIP VWVVSLVQHN QWPMGE.... ...LTCKVTH 302

BLR1 ..TFLFHLAV ADLLLVFILP FAVAEGSV.. GWVLGT.... ...FLCKTVI 303

CL5 .....LHLSV ADLLFVITLP FWAVDAVA.. NWYFGN.... ...FLCKAVH 304

LCR1 .....LHLSV ADLLFVITLP FWAVDAVA.. NWYFGN.... ...FLCKAVH 304

EBI1 ....LLNLAV ADILFLLTLP FWAYSAAK.. SWVFGV.... ...HFCKLIF 305

RBS1rat ....LLNLAL SDLLFVATLP FWTHYLIS.. HEGLHN.... ...AMCKLTT 306

EBI2 ....STNLVI SDILFTTALP TRIAYYAMGF DWRIGD.... ...ALCRITA 307

GCRTchick ....MLNLAI SDLLFVFTLP FRIYYFVVR. NWPFGD.... ...VLCKISV 308

APJ ..IFIASLAV ADLTFVVTLP LWATYTYRDY DWPFGT.... ...FFCKLSS 309

RTArat FSIYFLHLAS ADGIYLFSKA VIALLNMGTF LGSFPD.... ...YVRRVSR 310

UHRrat TNFLIGNLAL SDVLMCAACV PLTLAYAFEP RGWVFG.... ..GGLCHLVF 311

FMRL1 NTICYLNLAL ADFSFSAILP FRMVSVAMRE KWPFAS.... ...FLCKLVH 312

FMRL2 TTICYLNLAL ADFSFTATLP FLIVSMAMGE KWPFGW.... ...FLCKLIH 313 fMLP TTISYLNLAV ADFCFTSTLP FFMVRKAMGG HWPFGW.... ...FLCKFLF 314

OLF1catfish KYITVFNLAL SDLGGSSALI PKLIDTFLF. ......ENQV ISYEACLANM 315

OLF3catfish KYIAVFNLAL SDLCGSSALI PKLLDMLLF. ......ENQS ISYEACLSNM 316

OLF8catfish MCILIGLMAV VDLSMPIFCV PNMLLSFLF. ......NWKG ISLVGCLVQM 317

OLF32Acatfish KYMGIFNLAL SDFGETNVLI PSLVKTLFF. ......DSQY ISYDACLANM 318

OLF32Bcatfish KYMGIFNLAL SDFGETNALI PSLVKTLFF. ......DSQY ISYDACLANM 319

OLF32Ccatfish KYMGIFNLAL SDIGETNALI PSLVKTLFF. ......DSQY ISYDACLTNM 320

OLF32Dcatfish KYMGIFNLAL SDFGETNALI PSLVKTLFF. ......DSQY ISYDACLANM 319

OLF47catfish KFLAVFNLAV VDISINSVII PQMVPVFVF. ......NLNH ISFESCFSQM 321

OLF202catfish MYYIMLNLAA SDVLFSTTTL PKIIARYWF. ......GDGS ISFVGCFIQM 322

OLFCOR1chicken MYIFLQNLSF TDAAYSTVIT PKMLATFL.. ......EERKT ISYVGCILQY 323

OLFCOR2chicken MYIFLQNLSF TDAAYSTVIT PKMLATFL.. ......EERRT ISYVGCILQY 324

OLFCOR3chicken MYIFLQNLSF TDAAYSTVIT PKMLATFL.. ......EERKT ISYVGCILQY 323
```

```
-continued

OLFCOR4chicken  MYIFLQNLSF  TDAAYSTVIT  PKMLATFL..  .....EERKT  ISYVGCILQY  323

OLFCOR5chicken  MYIFLQNLSF  TDAAYSTVIT  PKMLATFL..  .....EERRT  ISYVGCILQY  324

OLFCOR6chicken  MYIFLQNLSF  TDAVYSTVIT  PKMLATFL..  .....EETKT  ISYVGCILQY  325

OLFdog   MYLFLSNLSF  SDLCFSSVTM  PKLLQNMQ..  .....SQVPS  IPYAGCLTQM  326

OLF07E    VYFFLANLSF  TDLFFVTNTI  PKMLVNLQ..  .....SHNKA  ISYAGCLTQL  327

OLF07I    MYLFLSNLSF  SDLCFSSVTI  PKLLQNMQ..  .....NQDPS  IPYADCLTQM  328

OLF07J    MYFFLSMLST  SETVYTLVIL  PRMLSSLV..  .....GMSQP  MSLAGCATQM  329

OLFOR3mouse   MYFFLSNLSS  LDLAFTTSSV  PQMLKNLW..  .....GPDKT  ISYGGCVTQL  330

OLFrat   MYYFLSSLSF  VDLCYSTVIT  PKMLVNFL..  .....GKKNF  ITYSECMAQF  331

OLFF3rat   MYFFLSNLSF  VDICFISTTV  PKMLVNIQ..  .....TQNNV  ITYAGCITQI  332

OLFF5rat   MYFFLSNLSF  VDVCFSSTTV  PKVLANHI..  .....LGSQA  ISFSGCLTQL  333

OLFF6rat   MYFFLCNLSF  LEIWFTTACV  PKTLATF...  ....APRGGV  ISLAGCATQM  334

OLFF12rat   MYFFLANLSF  VDTCFTSTTI  PKMLVNIY..  .....TQSKS  ITYEDCISQM  335

OLFI3rat   MYLFLSNLSF  SDLCFSSVTM  PKLLQNMR..  .....SQDTS  IPYGGCLAQT  336

QLFI7rat   MYFFLANMSF  LEIWYVTVTI  PKMLAGFIG.  ..SKENHGQL  ISFEACMTQL  337

OLFI8rat   MYLFLSNLSF  SDLCFSSVTM  LKLLQNIQ..  .....SQVPS  ISYAGCLTQI  338

OLFI9rat   MYLFLSNLSF  ADLCFSSVTM  PKLLQNMQ..  .....SQVPS  IPYAGCLAQI  339

OLFI14rat   MYLFLSNLSF  SDLCFSSVTM  PKLLQNMQ..  .....SQVPS  ISYTGCLTQL  340

OLFI15rat   MYLFLSNLSF  SDLCFSSVTM  PKLLQNMQ..  .....SQVPS  IPFAGCLTQL  341

OLFOR17_40   MYFFLGNLSV  LDVGCISVTV  PSMLSRLL..  .....SRKRA  VPCGACLTQL  342

GUST27rat   MYFFLSNLSF  VDICFISTTI  PKMLVNIH..  .....SQTKD  ISYIECLSQV  343

RPE    CHLLVLSLAL  ADSGISLNAL  VAATSSLLRR  WPYG......  ..SDGCQAHG  344

HHRF1   GDVYFINLAA  ADLLFVCTLP  LWMQYLLDHN  SLA.......  ..SVPCTLLT  345

HHRF2   SDTYICNLAV  ADLLIVVGLP  FFLEYAKHHP  KLSR......  ..EVVCSGLN  346

HHRF3   PTIYMTNLYS  TNFLTLTVLP  FIVLSNQWLL  PAG.......  ..VASCKFLS  347

MCP-1A   TDIYLLNLAI  SDLLFLITLP  LWAHSAANEW  VFG.......  ..NAMCKLFT  348

MCP-1B   TDIYLLNLAI  SDLLFLITLP  LWAHSAANEW  VFG.......  ..NAMCKLFT  348

PPR1bovine  TDVYILNLAV  ADLFLLFTLP  FWAVNAVHGW  VLG.......  ..KIMCKVTS  349
```

The above sequences were obtained from a public database. Examples of TM3 and TM5 transmembrane domain sequences are included in WO 94/05695, and are incorporated by reference. Examples of TM4, TM6, and TM7 transmembrane domain sequences can similarly be obtained from public sources.

2. Synthesis of Peptides

The peptides or fragments of GPCRs may be isolated from a natural source, chemically synthesized or produced recombinantly, in order to provide GPCR polypeptides which mimic, modulate or inhibit binding of ligands to G-protein coupled receptors.

a. Chemical Synthesis of GPCR Transmembrane Peptides

Transmembrane peptides of the present invention are be made using well known peptide synthesis procedures, as described in e.g., Merrifield, Science 232: 341–347 (1986), Barany and Merrifield, THE PEPTIDES, Gross and Meienhofer, eds. (N.Y., Academic Press), pp. 1–284 (1979); and Stewart and Young, SOLID PHASE PEPTIDE SYNTHESIS (Rockford, Ill., Pierce), 2d Ed. (1984), incorporated by reference herein.

The peptides were synthesized by a flow-through solid phase peptide synthesis on 432A Applied Biosystems Peptide Synthesizer utilizing Fmoc amino acid derivatives. To overcome aggregation that frequently occurs during the synthesis of hydrophobic peptides and leads to the blockage of the growing peptide chain, FmocHmb derivatives of Ala, Val and Leu were introduced into the different sequences, but not more than two derivatives of that type per peptide to prevent sterical hindrance during the synthesis. Coupling on the step after FmocHmb amino acid was prolonged to 90 min, since this protection group causes slowing of the next coupling step due to steric hindrance (T. Johnson, M. Quibell, Tetrahedron Lett. 35:463 (1994). The purity of the peptides was assessed by reverse phase HPLC and the structures were confirmed by matrix-assisted laser-desorption mass spectrometry.

b. Recombinant Production of GPCR Transmembrane Peptides

Nucleic acids that encode GPCR transmembrane peptides may be obtained by synthesizing, isolating or obtaining a nucleic acid sequence that encodes a GPCR protein, and subcloning a region of the sequence that encodes a desired transmembrane peptide.

i. Chemical Synthesis of Oligonucleotides

Oligonucleotides used in the present invention, including sequences that encode transmembrane peptides, are optionally chemically synthesized using the solid phase phosphoramidite triester method of Beaucage and Carruthers, *Tetrahedron Lett.*, 22(20): 1859–1862 (1981) using an automated synthesizer as described in Needham-VanDevanter et al., *Nucleic Acids Res.*, 12: 6159–6168 (1984). The chemically synthesized oligonucleotides are then purified by native acrylamide gel electrophoresis or by anion-exchange HPLC as described in Pearson and Regnier, *J. Chrom.*, 255: 137–149 (1983). The sequence of the synthetic oligonucleotide is verified, for example by using the chemical degradation method of Maxam and Gilbert in Grossman, L. and Moldave, D., eds. Academic Press, New York, *Methods in Enzymology*, 65:499–560 (1980).

The DNA sequences of the present invention coding for GPCR transmembrane peptides protein can be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These modified DNA sequences may be prepared, for example, by mutating known sequences so that the mutation results in the deletion, substitution, insertion, inversion or addition of one or more amino acids in the encoded polypeptide using various methods known in the art. For example, the methods of site-directed mutagenesis described in Taylor et al., Nucl. Acids Res. 13, 8749–8764 (1985) and Kunkel, *Proc. Natl. Acad. Sci. USA* 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). Both degenerate and non-degenerate mutations may be advantageous in producing or using the polypeptides of the present invention. For example, these mutations may permit higher levels of production, easier purification, or provide additional restriction endonuclease-recognition sites. All such modified DNAs (and the encoded polypeptide molecules) are included within the scope of the present invention.

ii. Recombinant Isolation of GPCR Transmembrane Peptide-Encoding Nucleic Acids

Nucleic acids that encode GPCR can be isolated from genomic or cDNA libraries, subcloning the library into expression vectors, labelling probes, DNA hybridization, and the like, as described in Sambrook, et al., MOLECULAR CLONING—A LABORATORY MANUAL (2nd Ed.), Vol. 1–3, Cold Spring Harbor Laboratory, Cold Spring Harbor, N.Y., 1989. This manual is hereinafter referred to as "Sambrook, et al.", and is incorporated herein by reference.

Various methods of amplifying target sequences, such as the polymerase chain reaction (PCR), can also be used to prepare DNA encoding GPCR transmembrane peptides or a peptide fragment thereof. In PCR techniques, oligonucleotide primers complementary to the two 3' borders of the DNA region to be amplified are synthesized. The polymerase chain reaction is then carried out using the two primers. See PCR PROTOCOLS: A GUIDE TO METHODS AND APPLICATIONS. (Innis, M, Gelfand, D., Sninsky, J. and White, T., eds.), Academic Press, San Diego (1990). Primers can be selected to amplify the entire regions encoding a full-length GPCR transmembrane peptides or to amplify smaller DNA segments as desired. Once selected sequences are PCR-amplified, oligonucleotide probes can be prepared from sequence obtained. These probes can then be used to isolate DNA's encoding GPCR transmembrane peptides or a peptide fragment thereof.

iii. Recombinant Expression of Transmembrane Peptide-encoding Nucleic Acids

Once a nucleic acid encoding a GPCR transmembrane peptides or a peptide fragment thereof is isolated and cloned, the nucleic acid is expressed in a variety of recombinantly engineered cells to ascertain that the isolated nucleic acid indeed encodes the desired GPCR transmembrane peptides or a peptide fragment thereof. The expression of natural or synthetic nucleic acids is typically achieved by operably linking a nucleic acid of interest to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith (1979), *Gene,* 8: 81–97; Roberts et al. (1987), *Nature,* 328:731–734; Berger and Kimmel, Guide to Molecular Cloning Techniques, *Methods in Enzymology* 152, Academic Press, Inc., San Diego, Calif. (Berger); Sambrook et al. (1989), MOLECULAR CLONING—A LABORATORY MANUAL (2nd ed.) Vol. 1–3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem. Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acids (e.g., coding sequences, promoters and vectors) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458, 066 and 4,500,707; Beaucage, et al., (1981) *Tetrahedron Lett.,* 22:1859–1862; Matteucci, (1981) et al., *J. Am. Chem.*

*Soc.*, 103:3185–3191; Caruthers, et al., (1982) *Genetic Engineering*, 4:1–17; Jones, chapter 2, Atkinson, et al., chapter 3, and Sproat, et al., chapter 4, in OLIGONUCLEOTIDE SYNTHESIS: A PRACTICAL APPROACH, Gait (ed.), IRL Press, Washington D.C. (1984); Froehler, et al., (1986) *Tetrahedron Lett.*, 27:469–472; Froehler, et al., (1986) *Nucleic Acids Res.*, 14:5399–5407; Sinha, et al. (1983) *Tetrahedron Lett.*, 24:5843–5846; and Sinha, et al., (1984) *Nucl. Acids Res.*, 12:4539–4557, which are incorporated herein by reference.

3. Derivatized Peptides and Peptidomimetics

The design of chemically modified peptides and peptide mimics which are resistant to degradation by proteolytic enzymes or have improved solubility or binding properties is well known.

Modified amino acids or chemical derivatives of GPCRs peptides according to the present invention may contain additional chemical moieties or modified amino acids not normally a part of the protein. Covalent modifications of the peptide are thus included within the scope of the present invention. Such modifications may be introduced into a GPCR polypeptide by reacting targeted amino acid residues of the polypeptide with an organic derivatizing agent that is capable of reacting with selected side chains or terminal residues. The following examples of chemical derivatives are provided by way of illustration and not by way of limitation.

The design of peptide mimics which are resistant to degradation by proteolytic enzymes is well known, both for hormone agonist/antagonist and for enzyme inhibitor design. See e.g., Sawyer, in STRUCTURE-BASED DRUG DESIGN, P. Verapandia, Ed., NY 1997; U.S. Pat. No. 5,552,534; and U.S. Pat. No. 5,550,251, all of which are incorporated by reference.

Historically, the major focus of peptidomimetic design has evolved from receptor-targeted drug discovery research and has not been directly impacted by an experimentally-determined three-dimensional structure of the target protein. Nevertheless, a hierarchical approach of peptide→peptidomimetic molecular design and chemical modification has evolved over the past two decades, based on systematic transformation of a peptide ligand and iterative analysis of the structure-activity and structure-conformation relationships of "second generation" analogs. Such work has typically integrated biophysical techniques (x-ray crystallography and/or NMR spectroscopy) and computer-assisted molecular modeling with biological testing to advance peptidomimetic drug design.

The three-dimensional structural properties of peptides are defined in terms of torsion angles ($\Psi$, $\phi$, $\omega$, $\chi$) between the backbone amine nitrogen ($N^\alpha$), backbone carbonyl carbon ($C^1$), backbone methionine carbon ($C^\alpha$), and side chain hydrocarbon functionalization (e.g., $C^\beta$, $C^\lambda$, $C^\delta$, $C^\epsilon$ of Lys) derived from the amino acid sequence. A Ramachandran plot ($\Psi$ versus $\phi$) may define the preferred combinations of torsion angles for ordered secondary structures (conformations), such as $\alpha$ helix, $\beta$ turn, $\gamma$ turn, or $\beta$ sheet. Molecular flexibility is directly related to covalent and/or noncovalent bonding interactions within a particular peptide. Even modest chemical modifications by $N^\alpha$-methyl, $C^\alpha$-methyl or $C^\beta$-methyl can have significant consequences on the resultant conformation.

The $N^\alpha$—$C^\alpha$—$C'$ scaffold may be transformed by introduction of olefin substitution (e.g., $C^\alpha$—$C^\beta$→C═C or dehydroamino acid or insertion (e.g., $C^\alpha$—$C'$→$C^\alpha$—$C$═$C$—$C'$ or vinylogous amino acid. Also the $C^\beta$ carbon may be substituted to advance the design of so-called "chimeric" amino acids Finally, with respect to N-substituted amides it is also noteworthy to mention the intriguing approach of replacing the traditional peptide scaffold by achiral N-substituted glycine building blocks. Overall, such $N^\alpha$—$C^\alpha$—$C$ scaffold or $C^\alpha$—$C^\beta$ side chain modifications expand peptide-based molecular diversity (i.e., so-called "peptoid" libraries) as well as extend our 3-D structural knowledge of traditional $\phi$-$\Psi$-$\chi$ space.

In one approach, such as disclosed by Sherman and Spatola, *J. Am. Chem. Soc.* 112: 433 (1990), one or more amide bonds are replaced in an essentially isosteric manner by a variety of chemical functional groups. For example, any amide linkage in any of the GPCR polypeptides can be replaced by a ketomethylene moiety, e.g. (—C(═O)—$CH_2$—) for (—(C═O)—NH—). A few of the known amide bond replacements include: aminomethylene or $\Psi[CH_2NH]$; ketomethylene or $\Psi[COCH_2]$; ethylene or $\Psi[CH_2CH_2]$; olefin or $\Psi[CH$═$CH]$; ether or $\Psi[CH_2O]$; thioether or $\Psi[CH_2S]$; tetrazole or $\Psi[CN_4]$; thiazole or $\Psi[thz]$; retroamide or $\Psi[NHCO]$; thioamide or $\Psi[CSNH]$; and ester or $\Psi[CO_2]$. These amide bond surrogates alter conformational and H-bonding properties that may be requisite for peptide molecular recognition and/or biological activity at receptor targets. Furthermore, such backbone replacements can impart metabolic stability towards peptidase cleavage relative to the parent peptide. The discovery of yet other nonhydrolyzable amide bond isostere has particularly impacted the design of protease inhibitors, and these include: hydroxymethylene or $\Psi[CH(OH)]$; hydroxyethylene or $\Psi[CH(OH)CH_2]$ and $\Psi[CH_2CH(OH)]$; dihydroxyethylene or $\Psi[CH(OH)CH(OH)]$, hydroxyethylamine or $\Psi[CH(OH)CH_2N]$, dihydroxyethylene and $C_2$-symmetric hydroxymethylene. Such backbone modifications have been extremely effective, as they may represent transition state mimics or bioisosteres of the hypothetical tetrahedral intermediate (e.g., $\Psi[C(OH)_2NH]$) for this class of proteolytic enzymes. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Both peptide backbone and side chain modifications may provide prototypic leads for the design of secondary structure mimicry, as typically suggested by the fact that substitution of D-amino acids, $N^\alpha$-Me-amino acids, $C_\alpha$-Me amino acids, and/or dehydroamino acids within a peptide lead may induce or stabilize regiospecific $\beta$-turn, $\gamma$-turn, $\beta$-sheet, or $\alpha$-helix conformations. To date, a variety of secondary structure mimetics have been designed and incorporated in peptides or peptidomimetics. The $\beta$-turn has been of particular interest to the area of receptor-targeted peptidomimetic drug discovery. This secondary structural motif exists within a tetrapeptide sequence in which the first and fourth C$\alpha$ atoms are <7 Å separated, and they are further characterized as to occur in a nonhelical region of the peptide sequence and to possess a ten-membered intramolecular H-bond between the i and i→4 amino acid residues. One of the initial approaches of significance to the design of $\beta$-turn mimetics was the monocyclic dipeptide-based template which employs side chain to backbone constraint at the i+1 and i+2 sites. Over the past decade a variety of other monocyclic or bicyclic templates have been developed as $\beta$-turn mimetics. Monocyclic $\beta$-turn mimetic has been described that illustrate the potential opportunity to design scaffolds that may incorporate each of the side chains (i, i+1, i+2 and i+3 positions), as well as five of the eight NH or C═O functionalities, within the parent tetrapeptide sequence, tetrapeptide sequence modeled in type l-IV β-turn conformations. Similarly, a benzodiazepine template has shown utility as a β-turn mimetic scaffold which also may be multisubstituted to simulate side chain functionalization, particularly at the i and i+3 positions of the corresponding tetrapeptide sequence modeled in type I–VI β-turn conformations. A recently reported γ-turn mimetic, illustrates an innovative approach to incorporate a retroamide surrogate between the i and i→1 amino acid residues with an ethylene bridge between the $N^1$ (i.e., nitrogen replacing the carbonyl C') and N atoms of the i and i+2 positions, and this template allows the possibility for all three side chains of the parent tripeptide sequence. Finally, the design of a β-sheet mimetic provides an attractive template to constrain the backbone of a peptide to that simulating an extended conformation. The β-sheet is of particular interest to the area of protease-targeted peptidomimetic drug discovery.

Aromatic amino acids may be replaced with D- or L-napthylalanine, D- or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of $C_1$–$C_{20}$.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —$SO_3H$) threonine, serine, tyrosine.

Other substitutions may include unnatural hyroxylated amino acids made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amino acid of said peptides can be replaced by the same amino acid but of the opposite chirality. Thus, any amino acid naturally occurring in the L-configuration (which may also be referred to as the R or S, depending upon the chemical entity) may be replaced with an amino acid of the same chemical structural type, but of the opposite caroled, generally referred to as the D- amino acid but which can additionally be referred to as the R- or the S-, depending upon its composition and chemical configuration. Such derivatives have the property of greatly increased stability co degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of GPCR polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

Tyrosyl residues may be modified by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to certain chemical moieties. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of GPCR polypeptides of the present invention may include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecule Properties, W. H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps.

Such derivatized moieties may improve the solubility, absorption, permeability across the blood brain barrier biological half life, and the like. Such moieties or modifications of GPCR polypeptides may alternatively eliminate or attenuate any possible undesirable side effect of the protein and the like. Moleties capable of mediating such effects are disclosed, for example, in Remington's Pharmaceutical Sciences, 16th ed., Mack Publishing Co., Easton, Pa. (1980).

Such chemical derivatives of GPCR polypeptides also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased binding affinity or modulation for GPCRs, which is desired for therapeutic compositions comprising GPCR polypeptides, antibodies thereto or fragments thereof. Such peptide derivatives are well-known in the art, as well as method steps for making such derivatives using carbodiimides active esters of N-hydroxy succinimmide, or mixed anhydrides, as non-limiting examples.

Variation upon the sequences of GPCR polypeptides of the present invention may also include: the addition of one or more (e.g., two, three, four, or five) lysine, arginine or other basic residues or one, or more (e.g., two, three, four, or five) glutamate or aspartate or other acidic residues at one end of the peptide, where "acidic" and "basic" are as defined herein. Negative charges can also be introduced by the addition of carboxyl, phosphate, borate, sulfonate or sulfate groups. Such modifications may increase the alpha-helical content of the peptide by the "helix dipole effect". They also can provide enhanced aqueous solubility of the peptide, and allow the correct insertion of peptides into a membrane structure.

In another approach, a variety of uncoded or modified amino acids such as D-amino acids and N-methyl amino acids have been used to modify mammalian peptides. Alternatively, a presumed bioactive conformation has been stabilized by a covalent modification, such as cyclization or by incorporation of gamma-lactam or other types of bridges. See, e.g., Veber and Hirschmann, et al., *Proc. Natl. Acad. Sci. USA*, 1978 75 2636 and Thorsett, et al., Biochem Biophys. Res. Comm., 1983 111 166. The primary purpose of such manipulations has not been to avoid metabolism or to enhance oral bioavailability but rather to constrain a bioactive conformation to enhance potency or to induce greater specificity for a receptor subtype.

The above examples of peptide scaffold- or nonpeptide template-based peptidomimetic agonists or antagonists illustrate various strategies to elaborate bioactive conformation and/or pharmacophore models of peptide ligands at their receptors. In many cases, receptor subtype selectivity has also been achieved by systematic structural modifications of prototypic leads of peptidomimetics. Thus, although the 3D structures of GPCRs remains elusive (except for models constructed from homology-based low-resolution 3D structures of bacteriorhodopsin or rhodopsin, see below) the development of pharmacophore models using the hierarchial approach in peptide→peptidomimetic structure-based drug design is promising.

4. Purification of GPCR Transmembrane Peptides

The polypeptides of this invention may be purified to substantial purity by standard techniques, including selective precipitation with such substances as ammonium sulfate, column chromatography, immunopurification methods, and others. See, for instance, R. Scopes, *Protein Purification: Principles and Practice*, Springer-Verlag: New York (1982), incorporated by reference. For example, the GPCR transmembrane peptides proteins and polypeptides produced by recombinant DNA technology are purified by a combination of cell lysis (e.g., sonication) and affinity chromatography or immunoprecipitation with a specific antibody to GPCR transmembrane peptides or a peptide fragment thereof. For fusion products, subsequent digestion of the fusion protein with an appropriate proteolytic enzyme releases the desired polypeptide. The proteins may then be further purified by standard protein chemistry techniques. A purified protein preferably exhibits a single band on an electrophoretic gel. Those of skill are reminded that the methods should take into account the hydrophobic nature of the peptides.

5. Detection of GPCR Transmembrane Peptide Gene Products

GPCR transmembrane peptides or a peptide fragment thereof to may be detected or quantified by a variety of methods. Preferred methods involve the use of specific antibodies.

a. Detection of GPCR Transmembrane Peptides by Immunoassay i. Antibody Production Methods of producing polyclonal and monoclonal antibodies are known to those of skill in the art. See, e.g., Coligan (1991), CURRENT PROTOCOLS IN IMMUNOLOGY, Wiley/Greene, NY; and Harlow and Lane (1989), ANTIBODIES: A LABORATORY MANUAL, Cold Spring Harbor Press, NY; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), *Nature,* 256:495–497. Such techniques include antibody preparation by selection of antibodies from libraries of recombinant antibodies in phage or similar vectors. See, Huse et al. (1989), *Science,* 246: 1275–1281; and Ward et al. (1989) *Nature,* 341:544–546. For example, in order to produce antisera for use in an immunoassay, a polypeptide is isolated as described herein. For example, recombinant protein is produced in a transformed cell line. An inbred strain of mice or rabbits is immunized with the peptide using a standard adjuvant, such as Freund's adjuvant, and a standard immunization protocol. Alternatively, a synthetic peptide derived from the sequences disclosed herein and conjugated to a carrier protein can be used an immunogen.

A number of immunogens may be used to produce antibodies specifically reactive with GPCR transmembrane peptides or a peptide fragment thereof. Recombinant protein is the preferred immunogen for the production of monoclonal or polyclonal antibodies. Naturally occurring protein may also be used either in pure or impure form. Synthetic peptides made using the GPCR transmembrane peptides or a peptide fragment thereof sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein such as GPCR transmembrane peptides or a peptide fragment thereof is mixed with an adjuvant and injected into an animal of choice (e.g., a mouse, rat, rabbit, pig, goat, cow, horse, chicken, etc.) at intervals of 1–4 weeks. The immunogen may be conjugated to a carrier protein can be used an immunogen. The animal's immune response to the immunogen preparation is monitored by taking test bleeds and determining the titer of reactivity to the GPCR transmembrane peptides or a peptide fragment thereof. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-GPCR transmembrane peptides or even GPCR transmembrane peptides from other cell types or species or a peptide fragment thereof, using a competitive binding immunoassay (see, e.g., Harlow and Lane, supra, at pages 570–573). Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

ii. Immunoassays

A particular protein can be measured by a variety of immunoassay methods. For a review of immunological and immunoassay procedures in general, see BASIC AND CLINICAL IMMUNOLOGY, 7th Edition (D. Stites and A. Terr, eds.) 1991. Moreover, the immunoassays of the present invention can be performed in any of several configurations, which are reviewed extensively in ENZYME IMMUNOASSAY, E. T. Maggio, ed., CRC Press, Boca Raton, Fla. (1980); "Practice and Theory of Enzyme Immunoassays," P. Tijssen, in LABORATORY TECHNIQUES IN BIOCHEMISTRY AND MOLECULAR BIOLOGY, Elsevier Science Publishers B.V. Amsterdam (1985); and, Harlow and Lane, ANTIBODIES, A LABORATORY MANUAL, supra, each of which is incorporated herein by reference.

Immunoassays to GPCR transmembrane peptides, peptidomimetics or subfragments thereof may use a polyclonal antiserum raised against a peptide or peptidomimetic of the invention. This antiserum is selected to have low cross-reactivity against other (other non-GPCR transmembrane peptides or other GPCR transmembrane peptides) peptides and any such cross-reactivity is removed by immunoabsorption prior to use in the immunoassay.

Immunoassays in the competitive binding format can be used for the crossreactivity determinations. For example, a reference peptide antigen of the invention can be immobilized to a solid support. The ability of other molecules (other GPCR transmembrane peptides, or non-GPCR transmembrane peptides, or unknowns) to compete with the binding of antisera which recognize the immobilized reference peptide antigen is measured. The ability of such molecules to compete with the binding of an antiserum or antibody to the immobilized reference peptide is compared to a standard molecule, such as the reference peptide antigen itself. The percent crossreactivity is calculated, using standard calculations. Antisera with less than 10% crossreactivity to cross-reacting molecules are selected and pooled. Any cross-reacting antibodies are optionally removed from the pooled antisera by immunoabsorption with cross-reacting molecules.

The immunoabsorbed and pooled antisera are then used in a competitive binding immunoassay to compare the binding of a second protein to that of the reference peptide antigen. In order to make this comparison, the two molecules are each assayed at a wide range of concentrations and the amount of each molecule required to inhibit 50% of the binding of the antisera to the immobilized reference peptide antigen is determined. If the amount of the second protein required is less than 10 times the amount of the reference peptide used to make the antibody, then the second protein is said to specifically bind to an antibody generated to the reference peptide antigen.

The presence of a desired polypeptide (including peptide, translation product, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

6. Detection of GPCR Transmembrane Peptide Sequences, Peptides and Peptidomimetics that Optimally Inhibit GPCR Biological Properties and Functions Peptides or peptide variants of the invention that modulate biological activity of GPCRs are generally identified as follows. Peptide sequences are selected from the transmembrane domains of the GPCR to be targeted. The transmembrane domains are readily ascertained by the application of computer models to known sequences. Computer modeling and comparison with known transmembrane peptide sequences are also used to define the orientation of the peptide sequence in the membrane, thus allowing the determination of the end of the peptide sequence that is towards the extracelluar aspect of the plama membrane. The selection of a preferred transmembrane domain to be targeted is largely empirical. We have found that peptides derived from transmembrane domain 2 are particularly effective inhibitors of GPCR function. Alternatively, peptide sequences selected from transmembrane domain 4 have also been effective antagonists.

Upon selection of a peptide sequence, a reference transmembrane sequence is synthesized and systematically modified to identify variants (or analogs) that have improved properties. The modifications introduce a negative charge at the extracellular end of the peptide sequence. Negative charges may be added in the form of acidic amino acid residues such as Asp or Glu. The number of acidic residues that is added is typically from 1 to 3 depending upon the hydrophobicity of the peptide sequence and the subsequent necessity to increase the solubility of the peptide. Further, preferable peptides have a neutral charge at the end of the peptide that is oriented towards the intracellular aspect of the plasma membrane. Thus, the overall hydrophobic nature of such a transmembrane peptide will result in insertion into a membrane and the negative charge at the extracellular end will result in the peptide having the same orientation as the transmembrane GPCR domain from which it is derived. Insertion into the membrane may be tested by fluorescent microscopy of labeled peptide analogs using methodology known to those of skill in the art as illustrated in Example 3 herein.

The ability of the peptide or peptide variants to modulate activity of the targeted GPCR is generally determined by testing the ability of the peptide to inhibit activation that is induced by a natural ligand of the targeted GPCR. Activation of most GPCRs results in an increase in cAMP or the release of intracellular calcium.

Thus, if activation of the target GPCR increases cAMP, the inhibitory activity of the peptide is determined by measuring cAMP levels using methods known to those in the art (see e.g., C. Nordstedt and B. B. Fredholm *Anal. Chem.* 189: 231–234 (1990). Similarly, if activation of the target GPCR releases intracellular calcium, the inhibitory activity of the peptide is determined by measuring the intracellular calcium levels as illustrated in the examples below.

Peptides may be tested for other properties including the following:
  enhanced ability to modulate GPCR activity;
  increased resistance to proteolysis;
  improved solubility;
  longer or shorter half-life, particularly in culture medium or a biological fluid such as plasma or whole blood;
  improved ability to insert into a membrane compartment, especially in a particular orientation, by means known in the art.

Variant peptides may also be synthesized having any one or more of the following modifications:
  conservative or non-conservative substitution of any of the amino acid residues;
  deletion or addition of residues at any position;
  chemical modification at any residue;
  peptidomimetic analogs of the reference peptide.

Variant peptides can be rationally designed and/or screened for using high throughput screening methodologies applied to combinatorial libraries. Methods of generating combinatorial libraries and screening such libraries using high-throughput methods are well known to those of skill in the art (see, e.g., Baum, *C&EN* (Feb. 7, 1994): 20–26 and references cited therein).

These variant peptides are also tested for the any of the above-listed properties. In general, a variant peptide is considered to have improved properties relative to the reference peptide if a given measurable property or parameter associated with the peptide has a value that is at least 10%, preferably at least 30%, more preferably at least 75%, and most preferably at least 95% better than the value for the reference peptide.

The relative ability of the modified peptides (as compared to the reference peptide) to modulate a GPCR biological activity is tested as follows. A cell line that expresses a GPCR and exhibits a GPCR-mediated biological activity is exposed to either the reference or the modified peptide under identical conditions, and the biological property of the GPCR is measured in the absence or presence of either peptide. Examples of cell lines, GPCRs expressed by the cell line, and GPCR-regulated properties measured include the following:

any cell that stably expresses CXCR4, especially attached cells, including cells that are genetically engineered to express CXCR4, including HeLa cells; CXCR4; stroma cell derived factor I-induced calcium flux;

any cell that stably expresses CXCR4, especially attached cells, including cells that are genetically engineered to express CXCR4, including CM cells; CXCR4; HIV-1 infection;

any cell that stably expresses CCKAR, especially attached cells, including cells that are genetically engineered to express CCKAR, such as CHO cells; CCKAR; cholecystokinin-induced calcium release;

any cell that stably expresses human CCR5, especially attached cells, including cells that are genetically engineered to express CCR5, including HEK cells; CCR5; RANTES induced calcium release.

The inhibitory activity is measured by exposing GPCR-expressing cells to a range of concentrations of a test antagonist, and measuring a biological property or activity associated with that GPCR. The test concentrations can range from 1 nanomolar to 100 micromolar, depending on peptide solubility and affinity. Initial screening is performed using 10-fold dilutions, such as 50, 5, 0.5, 0.05 micromolar. Then, the lowest active concentration is lowered in decrements of 10% to determine the lowest effective concentration. The property measured can be binding to a ligand (for example, binding of cholecystokinin octapeptide to CCKAR), or production of a measurable metabolic response (e.g., altered ion flux or translocation, altered phosphorylation, altered protein synthesis or degradation, altered cellular morphology, altered secretion, altered production of particular components such as soluble inositol phosphates, binding of a virus and subsequent infection, tumor growth, chemotaxis, mitogenic response, cell growth activation, secretion, muscle contraction, vasopressing and vasodepressing activity, synaptic transmission, and release of intracellular calcium, etc.)

The following GPCRs have been reported to play a role in HIV infection:

| | |
|---|---|
| STRL33 | U.S. Provisional Application No. 60/042,880; |
| CCRR5 | U.S. Patent Application No. 60/042,880; |
| CCR8: | U.S. Provisional Application No. 60/054,094; |
| CCR2 | Proc. Natl. Acad. Sci. USA: 2752–2756 (1994) |
| | J. Biol. Chem. 270: 29671–29675 (1995) |
| CCR3: | J. Biol. Chem. 270: 16491–16494 (1995) |
| CX3CR1: | DNA Cell Biol. 14: 673–680 (1995) |

The following is a list of transmembrane peptides that have GPCR antagonist properties:

```
From the GPCR CXCR4
F-2-2: LLFVITLPFWAVDAVANWYFGNDD        (SEQ ID NO:1)

F-2-5: LLFVITLPFWAVDAVANDD             (SEQ ID NO:2)

F-4-2: VYVGVWIPALLLTIPDFIFANDD         (SEQ ID NO:3)

F-6-1: VILILAFFACWLPYYIGISID           (SEQ ID NO:4)

F-7-3: DDEALAFFHCCLNPILYAFL-NH2        (SEQ ID NO:5)

F-7-4: DDSITEALAFFHCCLNPILYAFL-NH2     (SEQ ID NO:6)

From the GPCR CCR5
CCR5-TM-2-2: LFFL LTVPFWAHYAAAQWDFGDD  (SEQ ID NO:7)

CCR5-TM-4-1: FGVVTSVITWVVAVFASLPGIIFTSSDD  (SEQ ID NO:8)

CCR5-TM-6-1: LIFTIMIVYFLFWAPYNIVLLLNTFQED  (SEQ ID NO:9)

CCR5-TM-7-1: DDQAMQVTETLGMTHCCINPIIYAFV   (SEQ ID NO:10)

From the GPCR CCR2
CCR2-TM-2-1: IYLLNLAISDLLFLITLPLWADD   (SEQ ID NO:11)

CCR2-TM-2-2: LLFLITLPLWAH SAANEWVFGNDD (SEQ ID NO:12)

CCR2-TM-4-1: FGVVTSVITWLVAVF ASVPGIIFTDD  (SEQ ID NO:13)

CCR2-TM-6-1: VIFTIMIVYFLFWTPYN IVILLNTFQED  (SEQ ID NO:14)

CCR2-TM-7-1: DDATQVT ETLGMTHCCINPIIYAFV   (SEQ ID NO:15)

From the GPCR CCR3
CCR3-TM-2-1: LLFLVTLPFW IHYVRGHNWVFGDDD (SEQ ID NO:16)

CCR3-TM-4-1: FGVITSIVTWGLAVLAALPEFI FYETED  (SEQ ID NO:17)

CCR3-TM-6-1: IFVTMAVFFI FWTPYNVAILLSSYQSDD  (SEQ ID NO:18)

CCR3-TM-7-1: DDLVMLVTEVIAYSHCCMNPVIYAFV   (SEQ ID NO:19)

From the GPCR CCKAR
CCKAR-TM-1-6: DDEWQSALQILLYSIIFLLSV-   (SEQ ID NO:20)
LGNTLVITV

CCKAR-TN-2-1: FLLSLAVSDLMLCLFCMPFNLP   (SEQ ID NO:21)

CCKAR-TM-2-2: FLLSLAVSDLMLCLFCM PFNLIDD (SEQ ID NO:22)

CCKAR-TM-6-4: IVVLFFLCWMPIFSANAWRAYDTVDD  (SEQ ID NO:23)
```

7. Treatment Embodiments

The compositions containing the present GPCR transmembrane peptides, or a cocktail thereof (i.e., with other molecules, including other peptides of the invention), can be administered for therapeutic treatments. The molecules of the present invention are used to protect a patient from pathologies associated with GPCR, by modulating the biological activities associated with the GPCR. "Protection" from infection or disease as used herein is intended to encompass "prevention" or "treatment." "Treatment" involves administration of the protective composition to a patient exhibiting symptoms of a GPCR-associated pathology (for example, HIV-1 infection), so as to reduce or suppress the symptoms of the pathology. Other examples of GPCR-associated conditions that may be treated with the peptides of the invention include:

cancer. For example, vasoactive intestinal peptide (VIP) receptor is known to be overexpressed in breast cancer and lung cancer, and VIP antagonists are known to inhibit cancer growth. Thus, a peptide of the invention is probably effective in inhibiting such cancers;

antagonists of chemokine receptors as anti-inflamatory and anti asthma drugs;

tissue rejection;

neuropeptide Y receptor antagonists as anti-obesity drugs;

dopamine receptor D4 antagonists as drugs for treatment of depression, attention deficit hyperactivity disorder and schizophrenia;

antagonists of Corticotropin-Releasing Factor Receptor for the treatment of depression and anxiety related disoders;

angiotensin receptor antagonists as a mean of blood pressure control;

antagonists of gastrin-releasing peptide receptor, somatostatin and gastrin receptors as anti-neoplastic agents that slow down growth of endocrine tumors;

antagonists of opiod receptors as pain killers.

a. Pharmaceutical Compositions

The compositions for administration may be in the form of a solution, suspension, tablets, pill, capsule, powder, gel, cream, lotion, ointment, aerosol or the like. In a preferred embodiment, the compositions for administration comprise a solution of the GPCR transmembrane peptides dissolved in a pharmaceutically acceptable carrier, preferably an aqueous carrier. A variety of aqueous carriers can be used, e.g., buffeted saline and the like. These solutions are sterile and generally free of undesirable matter. These compositions may be sterilized by conventional, well known sterilization techniques. In certain embodiments, the GPCR transmembrane peptides are provided in powder form.

The GPCR transmembrane peptides and analogs may be combined with conventional excipient, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the GPCR in these formulations can vary widely, and will be selected primarily based on fluid volumes, viscosities, body weight and the like in accordance with the particular mode of administration selected and the patient's needs.

b. Administration and Dosage

The pharmaceutical composition or medium that comprises a GPCR transmembrane peptide is administered orally, parenterally, enterically, gastrically, topically, subcutaneously, rectally, locally or systemically. For example, the compounds can be injected into the bloodstream using a cannula or catheter; the vein or artery is selected to maximize delivery of cells to the affected tissue(s). Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980). It is recognized that the GPCR transmembrane peptides polypeptides and related compounds described above, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

In therapeutic applications, compositions are administered to a patient suffering from a disease or condition that in an amount sufficient to cure or at least partially arrest symptoms of the disease or conditions and its complications. An amount adequate to accomplish this is defined as a "therapeutically effective dose." Amounts effective for this use will depend upon the severity of the condition to be treated and the general state of the patient's health.

Generally, the dosage to be administered is the amount necessary to modulate a GPCR biological activity. It is understood that the dosage of a GPCR polypeptide of the present invention will be dependent upon the age, sex, health, and weight of the recipient, kind of concurrent treatment, if any, frequency of treatment, and the nature of the effect desired. The ranges of effective doses provided herein are not intended to limit the inventors and represent preferred dose ranges. The most preferred dosage will be tailored to the individual subject, as is understood and determinable by one of skill in the art, without undue experimentation. It is contemplated that the compounds will be administered under the guidance of a physician, who will determine the exact dosages, monitor the progress of the treatment, and determine whether a given administration is successful and sufficient, or whether subsequent administrations are needed.

The concentration of compounds to be administered at a given time and to a given patient will vary from 0.1 µg–100 mg and preferably 0.1–10 mg per day per patient. The dosage and mode of administration may be chosen to achieve and optionally maintain a local concentration in fluids that contact the target cells of about 0.001–50 µg/ml, preferably 0.1–10 µg/ml. Dosages from 0.1 up to about 100 mg per patient per day may be used, particularly when the drug is administered to a secluded site and not into the blood stream, such as into a body cavity or into a lumen of an organ. Substantially higher dosages are possible in topical administration.

Single or multiple administrations of the compositions may be necessary depending on the dosage and frequency as required and tolerated by the patient. In any event, the composition should provide a sufficient quantity of the peptides of this invention to effectively treat the patient.

c. Gene Therapy

The present invention provides packageable GPCR transmembrane peptide-encoding nucleic acids for the transformation of cells in vitro and in vivo. These packageable nucleic acids can be inserted into any of a number of well known vectors for the transfection and transformation of target cells and organisms.

The nucleic acids are transfected into cells, ex vivo or in vivo, through the interaction of the vector and the target cell. The GPCR transmembrane peptide-encoding nucleic acid, under the control of a promoter, then expresses the GPCR transmembrane peptide, thereby modulating the biological activity of a target GPCR.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992)256:808–813; Nabel and Feigner (1993) *TIBTECH* 11: 211–217; Mitani and Caskey (1993) TIBTECH 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al., (1995) in CURRENT TOPICS IN MICROBIOLOGY AND IMMUNOLOGY Doerfler and Böhm (eds) Springer-Verlag, Heidelberg Germany; and Yu et al., GENE THERAPY (1994) 1:13–26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990)

*Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al.-(1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Y et al., GENE THERAPY (1994), supra).

AAV-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invest.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4:2072–2081; Hermonat and Muzyczka (1984) *Proc. Natl. Acad. Sci. USA,* 81:6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996.

i. In Vitro Gene Transfer

It is expected that those of skill in the art are knowledgeable in the numerous expression systems available for expression of DNA encoding GPCR transmembrane peptides or a peptide fragment thereof. No attempt to describe in detail the various methods known for the expression of proteins in prokaryotes or eukaryotes is made here.

There are several well-known methods of introducing nucleic acids into bacterial and animal cells, any of which may be used in the present invention. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation, micro-injection of the DNA directly into the cells, infection with viral vectors, etc.

For in vitro applications, the delivery of nucleic acids can be to any cell grown in culture, whether of bacterial, plant or animal origin, vertebrate or invertebrate, and of any tissue or type. Contact between the cells and the genetically engineered nucleic acid constructs, when carried out in vitro, takes place in a biologically compatible medium. The concentration of nucleic acid varies widely depending on the particular application, but is generally between about 1 µmol and about 10 mmol. Treatment of the cells with the nucleic acid is generally carried out at physiological temperatures (about 37° C.) for periods of time of from about 1 to 48 hours, preferably of from about 2 to 4 hours.

In one group of embodiments, a nucleic acid is added to 60–80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 µg/mL, more preferably about 0.1 µg/mL.

ii. In vivo Gene Transfer

Alternatively, the GPCR transmembrane peptide encoding nucleic acids can also be introduced into target cells in vivo, using recombinant methods which are known to those of skill in the art. The insertion of genes into cells for the purpose of medicinal therapy is a rapidly growing field in medicine which has enormous clinical potential. Research in gene therapy has been on-going for several years, and has entered human clinical trials. Zhu, et al., *Science,* 261: 209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature,* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.,* 298:278–281 (1989), incorporated herein by reference, describes the in vivo transfection of lungs of mice with a functioning prokaryotic gene encoding the intracellular enzyme chloramphenicol acetyltransferase (CAT).

Formulations suitable for administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials. Injection solutions and suspensions can be prepared from sterile powders, granules, and tablets of the kind previously described.

For in vivo administration, pharmaceutical compositions that comprise GPCR transmembrane peptide-encoding nucleic acids are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., *Methods in Enzymology,* Academic Press, New York. 101:512–527 (1983); Mannino, et al., *Biotechniques,* 6:682–690 (1988); Nicolau, et al., *Crit. Rev. Ther. Drug Carrier Syst.,* 6:239–271 (1989), and Behr, *Acc. Chem. Res.,* 26:274–278 (1993). Still other methods of administering therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In preferred embodiments, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the preparations may be administered through endoscopic devices.

The nucleic acid can also be administered in an aerosol inhaled into the lungs (see, Brigham, et al., *Am. J. Sci.*, 298(4):278–281 (1989)) or by direct injection at the site of disease (Culver, *Human Gene Therapy*, MaryAnn Liebert, Inc., Publishers, New York. pp. 70–71 (1994)).

Effective doses of the compositions of the present invention will vary depending upon many different factors, including means of administration, target site, physiological state of the patient, and other medicants administered. Thus, treatment dosages will need to be titrated to optimize safety and efficacy. In determining the effective amount of the vector to be administered, the physician evaluates the particular nucleic acid used, the disease state being diagnosed; the age, weight, and condition of the patient, circulating plasma levels, vector toxicities, progression of the disease, and the production of anti-vector antibodies. The size of the dose also will be determined by the existence, nature, and extent of any adverse side-effects that accompany the administration of a particular vector. Doses ranging from about 10 ng to 1 g, 100 ng to 100 mg, 1 μg to 10 mg, or 30–300 μg DNA per patient are typical. Doses generally range between about 0.01 and about 50 mg per kilogram of body weight; preferably between about 0.1 and about 5 mg/kg of body weight or about $10^8$–$10^{10}$ or $10^{12}$ particles per injection. In general, the dose equivalent of a naked nucleic acid from a vector is from about 1 μg to 100 μg for a typical 70 kilogram patient, and doses of vectors which include a retroviral particle are calculated to yield an equivalent amount of inhibitor nucleic acid.

Prior to infusion, blood samples are obtained and saved for analysis. Between $10^8$ and $1 \times 10^{12}$ vectors are infused intravenously over 60–200 minutes. Vital signs and oxygen saturation by pulse oximetry are closely monitored. Blood samples are obtained 5 minutes and 1 hour following infusion and saved for subsequent analysis. At the physician's discretion, reinfusion is repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Vector infusion is slowed or discontinued depending upon the severity of the reaction.

In vivo gene transfer may be practiced in a variety of hosts. Preferred hosts include mammalian species, such as humans, non-human primates, dogs, cats, cattle, horses, sheep, and the like.

EXAMPLES

The following examples are simply embodiments of the invention and are not intended to limit the invention. A person of ordinary skill in the art can modify and/or adapt the invention for various applications without undue experimentation, without departing from the generic concept of the present invention. Therefore, such adaptations and modifications are within the scope and range of the present invention.

Example 1

Example 1 illustrates that peptides derived from transmembrane regions of CXCR4 inhibit CXCR4-mediated calcium fluxes.

Peptides having the selected sequences were synthesized by a flow-through solid phase peptide synthesis on 432A Applied Biosystems Peptide Synthesizer utilizing Fmoc amino acid derivatives. To overcome the aggregation that frequently occurs during the synthesis of hydrophobic peptides and leads to the blockage of the growing peptide chain, FmocHmb derivatives of Ala, Val and Leu were introduced into the difficult sequences. Charged residues were added to the peptide termini to assure a proper orientation of the peptides during penetration into the cellular membrane, and to improve the solubility of the highly hydrophobic peptides.

The purity of the peptides was assessed by reverse phase HPLC and the structures were confirmed by matrix-assisted laser-desorption time-of-flight (MALDI-TOF) mass spectrometry (Tarasova et al. (1998), *Ad. Exp. Med. Biol.*, Plenum Press, NY, pp. 201–206.)

Peptides used in this example are listed in Tables 1, 2, and 3.

The effect of the peptides on CXCR4-mediated calcium fluxes in HeLa cells that naturally express the CXCR4 receptor and U87 cells stably expressing the CXCR4 receptor was tested as follows. Cells grown on Nunc cover glass chamber slides were incubated with 1 micromolar Fura-2/AM for 20 min in a $CO_2$-incubator, rinsed with PBS and mounted on the stage of a Zeiss Axiovert inverted microscope. $[Ca^{2+}]_i$ measurements were performed using an Attofluor digital imaging system (Atto Instruments, Rockville, Md.). Fluorescence of Fura was excited at alternating wavelength of 340 and 380 nm. Fluorescence was monitored by an intensified CCD camera using a 505 cut-off filter. Calibrations of $[Ca^{2+}]_i$ signals were performed using $Ca^{2+}$ standards containing 1 micromolar Fura. CXCR4 antagonists were tested on HeLa cells and U87 cells. Stromal cell-derived factor-1α (SDF-1α) was used as a specific CXCR4 agonist.

CCR5 antagonists, which were used in selectivity studies as described below, were tested on HEK (human kidney carcinoma) cells stably expressing the CCR5 receptor and RANTES was used as an agonist. The antagonist activity of the peptides was evaluated by measuring the inhibition of agonist-evoked intracellular $Ca^{2+}$i release. These measurements were carried out in Fura-2/AM-treated cells, utilizing an Attofluor digital imaging system as described above. The agonist was SDF-1 α.

In the preliminary screen, peptides corresponding to the second and sixth transmembrane domains were found to abolish SDF-1α-induced signaling through CXCR4 receptor (Table 1). Further optimization and structure-activity studies allowed to obtain antagonists derived from all but the third and fifth transmembrane domains (Table 2).

TABLE 1

Activity of synthetic peptides corresponding to predicted transmembrane domains of CXCR4 in inhibition of SDF-1α-induced intracellular calcium release.

| Peptide | Concentration, required for complete inhibition of [Ca$^{2+}$$_I$] release |
|---|---|
| F-1-5:<br>DDIFLPTIYSIIFLTGIV-HN$_2$<br>(SEQ ID NO:350) | >30 μM |
| F-2-1:<br>LLFVITLPFWAVDAVANWYFGN<br>(SEQ ID NO:351) | 5 μM |
| F-3-1:<br>KAVHVIYTVNLYSSVLILAFISL-NH$_2$<br>(SEQ ID NO:352) | >50 μM |
| F-4-1:<br>KVYVGVWIPALLLTLPDFIF<br>(SEQ ID NO:353) | >50 μM |
| F-5-1:<br>HIMVGLILPGIVILSCYCIII-NH$_2$<br>(SEQ ID NO:354) | >50 μM |
| F-6-1:<br>VILILAFFACWLPYYIGISID<br>(SEQ ID NO:4) | 10 μM |
| F-7-1:<br>ALAFFHCCLNPILYAFLGAK-NH$_2$<br>(SEQ ID NO:355) | >100 μM |

TABLE 2

Biological activity of CXCR4 antagonists derived from different transmembrane domains. Anti signaling activity was determined in inhibition of SDF-1α-induced intracellular calcium release. Anti-HIV-1 activity was assessed in cytoprotection assay utilizing CEM-SS cells infected with HIV-1$_{RF}$.

| Peptide | Concentration, required for inhibition of signal transduction (μM) | EC$_{50}$ in anti-HIV-1 assay (μM) |
|---|---|---|
| F-2-2<br>LLFVITLPFWAVDAVANWYFGNDD<br>(SEQ ID NO:1) | 0.2 | 2.27 |
| F-4-2<br>VYVGVWIPALLLTIPDFIFANDD<br>(SEQ ID NO:3) | 5 | 0.3 |
| F-6-1<br>VILILAFFACWLPYYIGISID<br>(SEQ ID NO:4) | 10 | >50 |
| F-7-3<br>DDEALAFFHCCLNPILYAFL-NH$_2$<br>(SEQ ID NO:5) | 25 | 3.27 |
| F-6-1 + F-7-3 | 1 | No data |

To further understand the structural requirements for a successful antagonist, structure-activity studies were conducted on the peptides derived from the second transmembrane domain of CXCR4 (Table 3). The most potent antagonist, a 24 amino acid residue peptide F-2-2, completely blocked signal transduction at 0.2 micromolar. Addition of negatively charged residues to the termini appeared to be important for the activity. Elimination of the added negative charges provided by two C-terminal Asp residues (F-2-1) decreased antagonist potency more than ten-fold. Consistent with those findings, the substitution of negatively charged aspartate residues with positively charged lysines (F-2-3) resulted in 100-fold dicrease in antagonist activity. Deletion of five residues preceding the C-terminal aspartates (F-2-4) reduced the potency 20-fold. Truncation of the transmembrane portion by three N-terminal residues Leu-Leu-Phe rendered the peptide inactive.

TABLE 3

Structure-activity relationships in peptides derived from the second transmembrane domain of CXCR4: ...HLSVADLLFVITLPFWAVDAVANWYFGNFLCK... (SEQ ID NO:356) (predicted intramembrane portion is underlined)

| Peptide | Concentration, required for complete inhibition of [Ca$^{2+}$$_I$] release |
|---|---|
| F-2-1:<br>LLFVITLPFWAVDAVANWYFGN | 5 μM<br>(SEQ ID NO:351) |
| F-2-2:<br>LLFVITLPFWAVDAVANWYFGNDD | 0.2 μM<br>(SEQ ID NO:1) |
| F-2-8:<br>LLFVITLPFWAVDAVANWYFGNKK | 20 μM<br>(SEQ ID NO:357) |
| F-2-4:<br>VITLPFWAVDAVANWYFGNKK | >50 μM<br>(SEQ ID NO:358) |
| F-2-5:<br>LLFVITLPFWAVDAVANDD | 10 μM<br>(SEQ ID NO:2) |
| AcF-2-5:<br>AcLLFVITLPFWAVDAVANDD | 10 μM<br>(SEQ ID NO:359) |
| F-2-6:<br>LSVADLLFVITLPFWAVDAVANDD | 20 μM<br>(SEQ ID NO:360) |
| Rhod - AcF-2-2:<br>AcLLFVITLPFWAVDAVANWYFGNDDK(Rhod)D | 8 μM<br>(SEQ ID NO:361) |

Similar results were also observed for peptides derived from additional transmembrane regions. For example, in the case of peptides corresponding to the fourth transmembrane domain, positioning of the charged residue at the intracellular end of the peptide (F4-1, Table 1) instead of the extracellular end (F-4-2, Table 2) abolished the antagonist activity. Further, substitution of extracellular aspartates with lysines also abolished the antagonist activity (data not shown).

The specificity of the transmembrane domain interaction was demonstrated by the fact that all peptides derived from CXCR4 showed selectivity for that receptor and had no influence on signaling of the other chemokine receptor involved in HIV-1 entry, CCR5. Similarly, a peptide derived from the second transmembrane domain of CCR5, LFFLLTVPFWAHYAAAQWDFGDD (SEQ ID NO:7), completely abolished agonist induced signaling of the receptor in U87 cells at 500 nM concentrations, but had no effect on signaling of CXCR4.

It was further noted that an equimolar mixture of two peptides, F-6-1 and F-7-3, was an order of magnitude more potent than the most active of the two peptides. This synergistic effect produced by the derivatives of the sixth and seventh transmembrane regions may be a general phenomenon. Thus, pairs of TM analogs in optimized combinations may act as very potent antagonists.

Example 2

Example 2 illustrates that synthetic peptides corresponding to transmembrane domains of CXCR4 inhibit CXCR4-mediated HIV infection.

CCR5 and CXCR4 are believed to be the main co-receptors for HIVI cell entry (Broder et al., (1997), *J. Leukoc. Biol.* 62:2029; Doranz et al. (1997) *Immunol. Res.* 16: 1528; Premack and Schall (1996), *Nat. Med.* 2:11741178.), although other chemokine receptors appear to mediate infection as well (Michael et al. (1997) *Nat. Med.* 3(10):11602).

The ability of synthetic CXCR4-derived peptides of Table 1 to inhibit HIV-1 infection of CEM-SS cells was tested using an LAV strain of the virus that is known to utilize CXCR4 as a co-receptor. Anti-HIV-1 assay. Buckheit et al. (1993) Antiviral Research 21: 247. The CEM-SS cells were maintained in RPMI 1640 medium containing 10% fetal bovine serum. The cells were placed in each well of a 96-well microtiter plate to a density of $5 \times 10^3$ cells per well. The cells were infected with HIV-1 virus at a multiplicity of infection (MOI) previously determined to produce maximal level of viral production at 6 days post infection (MOI of 0.01).

Serial half-log dilutions of test compound were added to appropriate wells in triplicate to evaluate their ability to inhibit HIV-1 infection. AZT was used in parallel as a positive control. Following 6 days of incubation at 37° C., the presence and relative abundance of viral p24 protein was determined by ELISA in cell-free supernatants derived from each well of the microtiter plate. The p24 ELISA kit was purchased from the AIDS Vaccine Program, NCI, FCRDC (Frederick, Md.) and the assay was performed according to the manufacturer's instructions.

Most of the peptides in Table 1 showed some antiviral activity (data not shown). However, the peptides corresponding to the second and sixth transmembrane domains were the most potent in inhibition of HIV entry. The F-2-2 compound completely inhibited infection at a 5 micromolar concentration (FIG. 1).

Peptides corresponding to transmembrane domains of the cholecystokinin type A receptor (CCKAR) were used as negative controls and did not effect CXCR4 function, thereby confirming the specificity of the effect.

The peptides showed no cell toxicity in concentrations up to 100 micromolar (higher concentrations could not be tested because of solubility problems).

Figure 2:
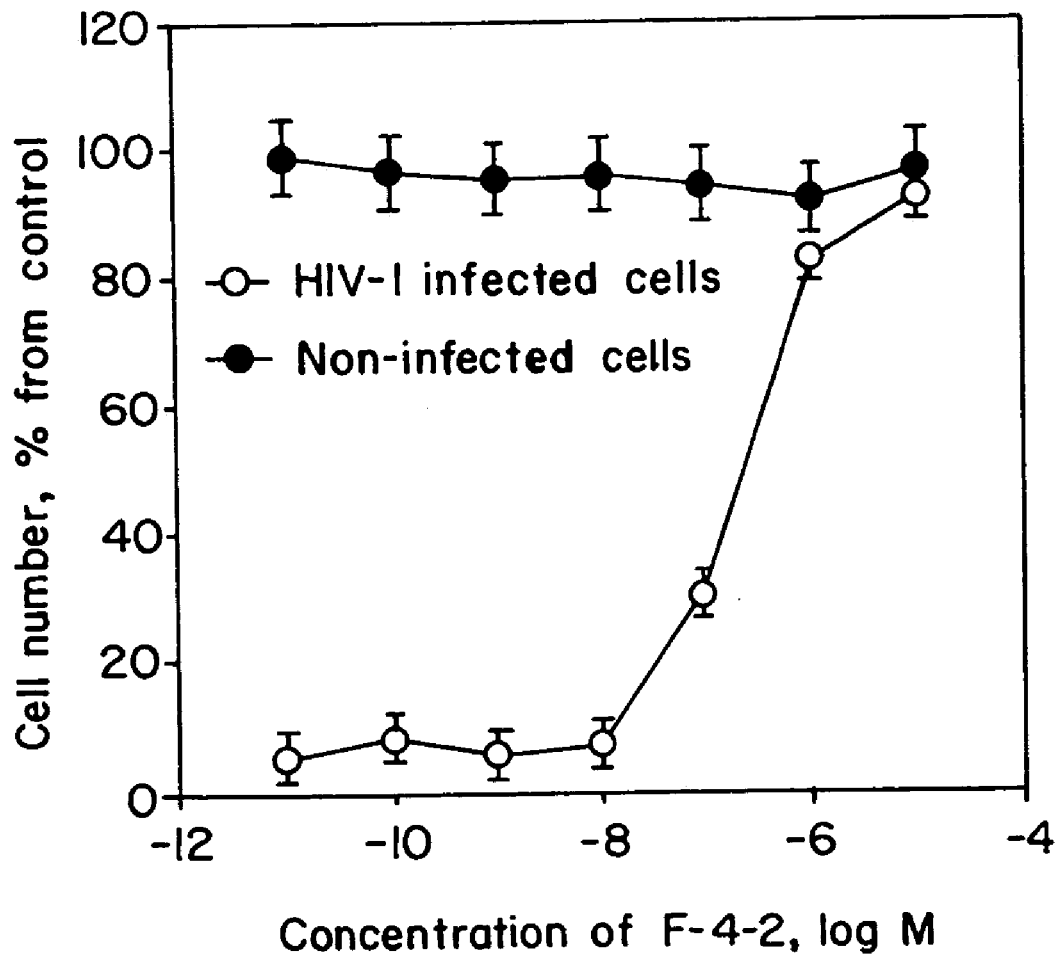
FIG. 2. Anti-HIV efficacy and toxicity of F-4-2 in cytoprotection. CEM-SS cells were infected with the RF strain of HIV-1, which causes cell death, if the inhibitor of infection is not present.

The ability of synthetic peptides to inhibit HIV-1 infection was additionally tested by cytoprotection assay using the highly cytopathic HIV-1 strain RF (Rice, et al. (1995) *Adv. Pharmacol.* 33:389,) (Table 2). The most potent peptide, F-4-2, completely inhibited infection at 1 micromolar concentration (FIG. 2). The peptides used as negative controls, which correspond to transmembrane domains of the cholecystokinin receptor type A, did not effect chemokine receptors functions.

Figure 3:
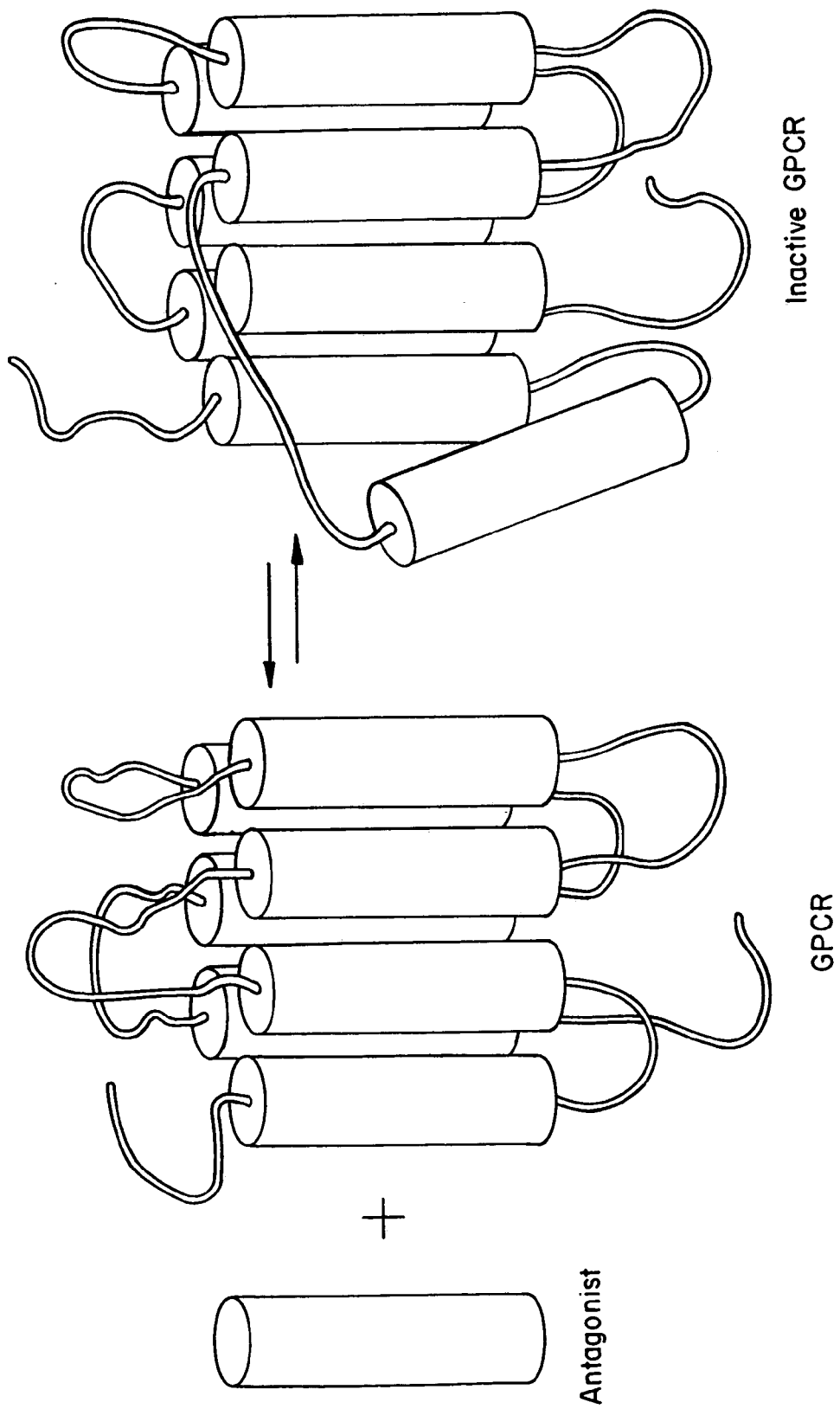
FIG. 3. The proposed model of transmembrane antagonists action.

The above results generally demonstrate the ability of externally added molecules to compete for interaction between transmembrane domains of GPCRs and thereby to disrupt receptor function (FIG. 3). In addition, it is important to note that the peptides of the invention inhibit HIV infection by targeting a cellular molecule and function rather than a viral molecule and function. Viral proteins have a relatively high mutation rate, which often allows viruses to become resistant to a given treatment. Because cellular proteins mutate at a far slower rate, the probability that a virus will be able to develop a resistance is greatly reduced.

Example 3

Example 3 shows that the peptides of the invention partition to the plasma membrane and other membrane compartments.

A fluorescent derivative of CXCR4 TM2, rhodamine-F-2, was synthesized by solid-phase synthesis on 432A Applied Biosystems Peptide Synthesizer utilizing Fmoc amino acid derivatives. Rhodamine B (Fluka) was loaded onto the amino acid column of the instrument. The purity of the peptide was assessed by reverse phase HPLC and the structures were confirmed by matrix-assisted laser desorption mass spectrometry.

A chimeric protein consisting of the CXCR4 and the green fluorescent protein (GFP) was used for studying receptor localization, internalization, and recycling in live cells in real time. This construct was made and stably expressed in HeLa cells as described in Tarasova et al. (1997), *J. Biol. Chem.* 272: 14817–14824. Fusion of the C terminus of the CXCR4 to the N terminus of the GFP did not appear to alter receptor ligand binding affinity, signal transduction, or the pattern of receptor surface expression and distribution.

Transfected CXCR4-GFP-expressing HeLa cells were grown in coated 50 mm cover glass bottom dishes (MatTek, MA) in medium without phenol red. The cells were then exposed to 1 micromolar peptide in DMEM medium for 30 min in a $CO_2$-incubator. The distribution of fluorescent label was determined by confocal laser scanning microscopy on a Zeiss inverted LSM 410 laser scanning confocal microscope. Fluorescence of GFP was excited using a 488 nm argon/krypton laser; emitted fluorescence was detected with 515–540 nm bandpass filter. For rhodamine red a 568 nm helium/neon laser was used for excitation and fluorescence was detected with a 590–640 nm bandpass filter.

The results demonstrated that the rhodaminated peptide co-localized with the CXCR4-GFP and was present at the cellular membrane within minutes after application and saturated endosomes and the endopolasmic reticulum after 15 minutes of incubation. This confirmed the ability of the peptides to concentrate in the cellular membranes and suggested that the peptides interacted with receptor molecules.

Example 4

Example 4 shows that peptides corresponding to transmembrane domains of the cholecystokinin type A receptor (CCKAR) inhibits agonist-evoked intracellular calcium release with a potency similar to CXCR4 compounds.

To further illustrate the present invention, we have synthesized peptides derived from the transmembrane domains of the rat cholecystokinin receptor type A (CCKAR). Although CCKAR belongs to the same rhodopsin family of GPCRs as CSCR4, its sequence is only 15% identical to that of CXCR4, when aligned using the Dialign 2 program (Morgenstern, et al,. (1996) *Proc. Natl. Acad. Sci. USA* 93:12098) and the degree of identify in transmembrane regions is only [27]%.

The activity of peptides from the CCKAR transmembrane domain were tested in transfected CHO cells that stably express rat CCKAR (Tarasova et al. (1997), *J. Biol. Chem.* 272: 14817–14824). Sulfated cholecystokinin octapeptide was the CCKAR agonist. Determination of intracellular calcium release was performed as described in example 1 above. The results are shown in Table 4.

None of CCKAR-derived peptides served as antagonists of chemokine receptors and none could inhibit HIV-1 infection. The activity of the antagonists in inhibiting signaling through the receptor was compared to the ability to prevent agonist binding (Table 4). Inhibition of signaling was assessed in CCK-8 evoked intracellular calcium release in FURA-2/AM treated CHO cells stably transfected with rat CCKAR (Tarasova, et al. (1997) *J. Biol. Chem.* 272:14817). Inhibition of ligand binding was measured with the use of a fluorescent agonist, rhodamine green CCK-8 (RG-CCK-8) and quantitative confocal laser scanning microscopy (Tarasova, et al. (1997) *J. Biol. Chem.* 272:14817). Peptides derived from the first, second, and sixth transmembrane domains inhibited CCK-induced signaling through the CCKAR receptor. Peptides derived from the first and the second transmembrane domains, CCKAR-1-1 and CCKAR-2-1, had comparable potencies with respect to the inhibition of ligand signaling and binding. A peptide derived from the sixth domain, CCKAR-6-1, was active in inhibition of signaling, but had very low activity in inhibition of RG-CCK-8 binding.

TABLE 4

The activity of CCKAR-derived TM peptides in inhibition of CCK-8-induced intracellular calcium release and RG-CCK-8 binding.

| Peptide | Concentration, required for inhibition of signaling | $IC_{50}$ in inhibition of RG-CCK-8 binding |
|---|---|---|
| CCKAR-TM-1-6:<br>DDEWQSALQILLYSIIFLLSVLGNTLVITV<br>(SEQ ID NO:20) | 50 μM | 20 μM |
| CCKAR-TM-2-1:<br>FLLSLAVSDLMLCLFCMIPFNLP<br>(SEQ ID NO:21) | 2 μM | 0.5 μM |
| CCKAR-TM-4-2 (#71)<br>VIAATWCLSFTLMTPYPIYSNLVPFTDD<br>(SEQ ID NO:362) | >50 μM | >50 μM |
| CCKAR-TM-5-3 (#45)<br>DDQTFLLLILFLLPGIVMVVAYGL<br>(SEQ ID NO:363) | >50 μM | >50 μM |
| CCKAR-TM-6-4 (#77)<br>IVVLFFLCWMPIFSANAWRAYDTVDD<br>SEQ ID NO:23 | 5 μM | >50 μM |

What is claimed is:

1. A method of inhibiting the biological activity of a target G protein-coupled receptor (GPCR) by contacting a cell that expresses said GPCR with an isolated GPCR-modulating molecule comprising a peptide that has at least five amino acids, an N-terminus and a C-terminus, said at least five amino acids being identical to the amino acid sequence of a portion of a transmembrane domain of said GPCR, wherein
  (a) said molecule has an extracellular end group that is negatively charged under physiological conditions, an intracellular end group with a neutral charge sufficient to allow insertion into a membrane under physiological conditions, and said molecule comprises the following modifications: when said intracellular end group is said C-terminus, said neutral charge includes a terminal carboxyamide group; or, when said intracellular end group is said N-terminus, said peptide or peptidomimetic includes at least four of the first five N-terminal amino acids having neutrally-charged amino acid side chains under physiologic conditions; and at least one of the end groups is a group that does not naturally occur at that position in the transmembrane sequence;
  (b) said molecule spontaneously inserts into a membrane in the same orientation as the transmembrane domain from which it is derived, wherein said molecule without the modifications in (a) does not spontaneously insert into the membrane in said orientation; and
  (c) said molecule inhibits a biological activity of said GPCR by disrupting the structure or assembly of said GPCR,
wherein the biological activity is selected from the group consisting of signal transduction, binding of a virus and subsequent infection, tumor growth, chemotaxis, mitogenic response, cell growth activation, secretion, muscle contraction, vasopressing and vasodepressing activity, synaptic transmission, and release of intracellular calcium.

2. A method of claim 1, wherein the concentration of the molecule is about 0.01 to about 100 micromolar.

3. A method of claim 1, wherein the molecule inhibits a signal transduction of the GPCR.

4. A method of claim 1, wherein the molecule comprises a peptide selected from the group consisting of:

```
From the GPCR CXCR4
F-2-2:  LLFVITLPFWAVDAVANWYFGNDD                        (SEQ ID NO:1)

F-2-5:  LLFVITLPFWAVDAVANDD-OH                          (SEQ ID NO:2)

F-4-2:  VYVGVWIPALLLTIPDFIFANDD-OH                      (SEQ ID NO:3)

F-6-1:  VILILAFFACWLPYYIGISID-OH                        (SEQ ID NO:4)

F-7-3:  DDEALAFFHCCLNPILYAFL-NH2                        (SEQ ID NO:5)

F-7-4:  DDSITEALAFFHCCLNPILYAFL-NH2                     (SEQ ID NO:6)

From the GPCR CCR5
CCR5-TM-2-2:  LFFL LTVPFWAHYAAAQWDFGDD                  (SEQ ID NO:7)

CCR5-TM-4-1:  FGVVTSVITWVVAVFASLPGIIFTSSDD              (SEQ ID NO:8)

CCR5-TM-6-1:  LIFTIMIVYFLFWAPYNIVLLLNTFQED              (SEQ ID NO:9)

From the GPCR CCR2
CCR2-TM-2-1:  IYLLNLAISDLLFLITLPLWADD-OH                (SEQ ID NO:11)

CCR2-TM-2-2:  LLFLITLPLWAH SAANEWVFGNDD-OH              (SEQ ID NO:12)

CCR2-TM-4-1:  FGVVTSVITWLVAVF ASVPGIIFTDD               (SEQ ID NO:13)

CCR2-TM-6-1:  VIFTIMIVYFLFWTPYN IVILLNTFQED             (SEQ ID NO:14)

From the GPCR CCR3
CCR3-TM-2-1:  LLFLVTLPFW IHYVRGHNWVFGDDD                (SEQ ID NO:16)

CCR3-TM-4-1:  FGVITSIVTWGLAVLAALPEFI FYETED             (SEQ ID NO:17)

CCR3-TM-6-1:  IFVIMAVFFI FWTPYNVAILLSSYQSDD             (SEQ ID NO:18)
```

```
From the GPCR CCKAR
CCKAR-TM-2-2:  FLLSLAVSDLMLCLFCM PFNLIDD       (SEQ ID NO:22)

CCKAR-TM-6-4:  IVVLFFLCWMPIFSANAWRAYDTVDD      (SEQ ID NO:23).
```

5. A method of claim 1, wherein the target GPCR is CCKAR and the inhibited biological activity is inhibition of CCKAR-mediated intracellular $Ca^{2+}$ release.

6. A method of inhibiting the biological activity of a target G protein-coupled receptor (GPCR) by contacting a cell that expresses said GPCR with an isolated GPCR-modulating molecule comprising a peptide that has at least five amino acids, an N-terminus and a C-terminus, said at least five amino acids being identical to the amino acid sequence of a portion of a transmembrane domain of said GPCR, wherein (a) said molecule has an extracellular end group that is negatively charged under physiological conditions, an intracellular end group with a neutral charge sufficient to allow insertion into a membrane under physiological conditions, and said molecule comprises the following modifications: said intracellular end group is said C-terminus and said neutral charge includes a terminal carboxylamide group; and at least one of the end groups is a group that does not naturally occur at that position in the transmembrane sequence;

(b) said molecule spontaneously inserts into a membrane in the same orientation as the transmembrane domain from which it is derived, wherein said molecule without the modifications in (a) does not spontaneously insert into the membrane in said orientation; and (c) said molecule inhibits a biological activity of said GPCR by disrupting the structure or assembly of said GPCR, wherein the biological activity is selected from the group consisting of signal transduction, binding of a virus and subsequent infection, tumor growth, chemotaxis, mitogenic response, cell growth activation, secretion, muscle contraction, vasopressing and vasodepressing activity, synaptic transmission, and release of intracellular calcium.

7. The method of claim 6, wherein the molecule comprises a peptide selected from the group consisting of:

```
From the GPCR CXCR4
F-7-3:  DDEALAFFHCCLNPILYAFL-NH2        (SEQ ID NO:5)

F-7-4:  DDSITEALAFFHCCLNPILYAFL-NH2     (SEQ ID NO:6).
```

* * * * *